(12) United States Patent
Li et al.

(10) Patent No.: US 12,391,754 B2
(45) Date of Patent: Aug. 19, 2025

(54) FUSION PROTEIN OF SINGLE DOMAIN ANTIBODY AND PROCOAGULANT

(71) Applicant: Beijing Neoletix Biological Technology Co., Ltd., Beijing (CN)

(72) Inventors: Qi Li, Lawrenceville, GA (US); Huafei Zou, Norcross, GA (US)

(73) Assignee: Beijing Neoletix Biological Technology Co., Ltd., Beijing (CN)

( * ) Notice: Subject to any disclaimer, the term of this patent is extended or adjusted under 35 U.S.C. 154(b) by 941 days.

(21) Appl. No.: 17/452,033

(22) Filed: Oct. 22, 2021

(65) Prior Publication Data

US 2022/0041716 A1 Feb. 10, 2022

Related U.S. Application Data

(63) Continuation of application No. PCT/US2020/029599, filed on Apr. 23, 2020.

(60) Provisional application No. 62/844,610, filed on May 7, 2019.

(51) Int. Cl.
*C07K 16/28* (2006.01)
*A61K 39/00* (2006.01)
*A61P 7/04* (2006.01)

(52) U.S. Cl.
CPC .......... *C07K 16/2803* (2013.01); *A61P 7/04* (2018.01); *A61K 2039/505* (2013.01); *C07K 2317/34* (2013.01); *C07K 2317/51* (2013.01); *C07K 2317/515* (2013.01); *C07K 2317/565* (2013.01); *C07K 2319/33* (2013.01)

(58) Field of Classification Search
None
See application file for complete search history.

(56) References Cited

U.S. PATENT DOCUMENTS

2008/0131423 A1 6/2008 Mori et al.
2019/0062429 A1 2/2019 Hilden et al.

FOREIGN PATENT DOCUMENTS

WO 2013063095 A1 5/2013

OTHER PUBLICATIONS

Henry, et. al, MAbs, 2018, 10, 815-826 (Year: 2018).*
Liu, et. al, Front Immunol, 2022, 13, 1-18 (Year: 2022).*
Gordon, et. al, Front Immunol, 2023, 14, 1-18 (Year: 2023).*
Asaadi, et. al, Biomarker Res, 2021, 9, 1-20 (Year: 2021).*
International Search Report for PCT Application No. PCT/US2020/029599. Mail Date: Sep. 28, 2020. 1 page.

\* cited by examiner

*Primary Examiner* — Misook Yu
*Assistant Examiner* — Samantha Lake Hopkins
(74) *Attorney, Agent, or Firm* — Perkins Coie LLP; Viola Kung

(57) ABSTRACT

The present invention relates to single domain antibodies (sdAbs) against TREM (triggering receptors expressed on myeloid cells) like transcript-1 (TLT-1) molecules that are present on activated platelets at the site of an injury, and especially on a subset of activated platelets, coated platelets. Furthermore, the present invention relates to fusion proteins comprising sdAbs against TLT-1 and an extracellular (soluble) domain of tissue factor (sTF), to direct targeting of such fusion proteins to activated platelets at the site of injury through binding of the sdAbs to TLT-1, a membrane protein receptor that is only present on activated platelets. Specific interaction of sdAbs with the TLT-1 receptor positions the sTF domain of the fusion to interact with, and activate, FVII. As a result, a targeted procoagulant effect is achieved at the site of injury via activated platelets. The fusion proteins are useful to treat individuals that have a bleeding disorder, such as hemophilia A, hemophilia B, or acute bleeding due to traumatic injury.

10 Claims, 24 Drawing Sheets

Specification includes a Sequence Listing.

FIG. 2

| NLX # | SEQ ID NO | Sequence (CDR1, CDR2, CDR3 underlined) |
|---|---|---|
| 2-64 | (62) | QVQLVESGGGLVQAGGSLRLSCAASGNTSGINVMAWYRQASGKQRELVANKARGGLPKYGNSAKGRFTISRDNAKNTIYLQMNNLKPEDTAVYYCNAVWDWALAEYWGQGTQVTVSS |
| 3-5 | (63) | QVQLVESGGGLVQAGGSLRLSCAASGDTSGINIMAWYRQAPGKQRELVANKARGGLPKYADSAKGRFTISRDNAKNTIYLQMNNLKPDDTAVYYCNAVWDWALAEYWGQGTQVTVSS |
| 2-2 | (64) | QVQLVESGGGLVQAGGSLRLSCAASGSTSDINIMAWYRQVSGKARELVANKARGGLPKYADFAKGRFTISRDNAKNTILLQMNNLKPEDTGVYYCNAVSDWKLGDYWGQGIQVTVSS |
| 2-25 | (65) | QVQLVESGGGLVQAGGSLRLSCAASGSTSDINIMAWYRQVSGKQRELVANKARGGLPKYGDFVKGRFAISRDNAKNIVYLQMNSLKPEDTAVYYCNAVTDWALGDYWGQGTQVTVSS |
| 2-43 | (66) | QVQLVESGGGLVQAGGSLRLSCAASGSTSEINVMAWYRQVSGNQRELVANKARGGLPKYGDFVKGRFAISRDNAKNTITLQMNNLKPEDTAVYYCNAVTDWALGDYWGQGTQVTVSS |
| 3-20 | (67) | QVQLVESGGGLVQAGGSLRLSCAASGSTSEINIMAWYRQVSGNQRELVANKARGGLPKYGDFVKGRFAISRDNAKNTITLQMNNLKPEDTAVYYCNAVTDWALGDYWGQGTQVTVSS |
| 2-33 | (68) | QVQLVESGGGLVQPGGSLTLSCAASGSIANIGGMAWYRRLPGNKRAMVASITSAGTASSYIDSVKGRFTISRDNAKNTVYLQMTSLKPEDTAVYLCKAWDRDLVDYWGQGIQVTVSS |
| 2-18 | (69) | QVQLVESGGGLVQPGGSLTLSCAASGSIANINGMAWYRRLPGKVRAMVASITSAGTASSYIDSVKGRFTISRDNAKNTVYLQMTSLKPEDTAVYYCKAWDRDLVDYWGQGIQVTVSS |
| 2-90 | (70) | QVQLVESGGGLVQAGGSLRLSCAASGNTSGINVMAWYRQAPGKQRELVANKARGGLPKYADSAKGRFTISRDNTKNTISLQMNSLKPEDTAVYYCNALLDWRLGDYWGQGTQVTVSS |
| 2-69 | (71) | QVQLVESGGGLVQAGGSLRLSCAASGSTSGINLMAWYRQASGKQRELVANIARGGLPKYADSAKGRFTISRDNAKNTMYLQMNSLKPEDTAVYYCNAVWDWKLGDYWGQGTQVTVSS |
| 2-67 | (72) | QLQLVESGGGTVQAGGSLRLSCAASGSTSGINIMAWYRQRSGEPRELVANKARGGLPKYADFARGRFTISRDNAKNTIDLQMSNLKPEDSAVYYCNAVWDWKLGDYWGQGTQVTVSS |
| 3-108 | (73) | QVQLVESGGGTVQAGGSLRLSCAASGNTSGINIMAWYRQRSGEPRELVANKARGGLPKYADSAKGRFTITRDNAKNTIYLQMNNLKPEDTAVYYCNAVWDWKLGDYWGQGTQVTVSS |
| 2-127 | (74) | QVQLVESGGGLVQAGGSLRLSCVASGSTSDINIMAWYRQAQGKQRELVANKARGGLPKYGDFVKGRFAISRDNAKNTIYLQMNSLKPEDTGVYYCNAVTDWQLGDYWGQGTQVTVSS |

FIG. 2 (Continued)

| NLX # | SEQ ID NO | CDR1 | CDR2 | CDR3 |
|---|---|---|---|---|
| 2-54: | (75) | QLQLVQSGGGLVQAGGSLRLSCVASGSTPDINLMAWYRQASGKQRELVANKARGGLPKYADFAKGRFTISRDNAKNTITLQMNSLKPEDTAVYYCNALLDWRAGDYWGQGTQVTVSP | | |
| 2-132: | (76) | QLQLVESGGGLVQAGGSLRLSCVASGSTSDINLMAWYRQASGKQRELVANKARGGLPKYADFAKGRFTISRDNAKNTITLQMNSLKPEDTAVYYCNALLDWRAGDYWGQGTQVTVSP | | |
| 3-119: | (77) | QLQLVESGGGLVQAGGSLRLSCAASGDTSDINVMAWYRQASGKQRELVANKARGGLPKYADFAKGRFTISRDNAKNTITLQMNSLKPEDTAVYYCNALLDWRAGDYWGQGTQVTVSP | | |
| 3-3: | (78) | QLQLVESGGGSVQAGGSLRLSCVASGGSTSDINLMAWYRQASGKQRELVANKARGGLPKYADFAKGRFTISRDNAKNTLVLQMDLKPEDTAVYYCNALLDWALGEYWGQGTQVTVSS | | |
| 3-7: | (79) | QLQLVESGGGLVQAGGSLRLSCAASGRSTSDINIMAWYRQASGKQRELVANKARGGLPKYADFAKGRFTISRDNAKNTVYLEMNSLKPEDTATYYCNAVLDWKLGEYWGQGTQVTVSS | | |
| 3-32: | (80) | QVQLVESGGGLVQPGGSLRLSCAASGNTSGINVMAWYRQASGKQRELVANKARGGLPKYADFAKGRFTISRDNAKNTVSLQMNSLKPEDTAVYYCNAVWDWQLGDYWGQGTQVTVSS | | |
| 3-110: | (81) | QVQLVESGGGLVQAGGSLRLTCVASGNTSGINVMAWYRQTSGKQRELVANKARGGLPKYADSAKGRFTISRDNAKNTLYLQMNNLKPEDTGVYYCNAVWDWQLGDYWGQGTQVTVSS | | |
| 2-5: | (82) | QLQLVESGGGLVQAGGSLRLSCAASRDIFSFNVMGWYRQAPGKQRELVAFITTSAGYTNVVHSVKGRFTISRDNTKNTVYLQMSSLKPEDTAVYYCAAAEAYAEKYDYWGQGTQVTVSS | | |
| 2-30: | (83) | QLQLVESGGGLVQAGGSLRLSCAASGSISSINVMGWYRQAPGKQRELVAFITTPGYTNYAHSVKGRFTISRDNAKNTVYLQMNSLKPQDTAVYYCAAAEAYAEKYDYWGQGTQVTVSS | | |
| 2-6: | (84) | QVQLVESGGGLVQAGGSLRLSCAASGSTSNINIMAWYRQALGKPRELVANKARGGLPKKYADFAKGRFTISRDNAKNAVYLQMNSLKPEDTAVYYCNAVEDWRLGDYWGQGTQVTVSS | | |
| 2-138: | (85) | QVQLVESGGGLVQAGGSLRLSCAASGSTSSINIMAWYRQAPGKPRELVANKARGGLPKYADFAKGRFTISRDNAKNTVYLQMNSLKPEDTAVYYCNAVEDWRLGDYWGQGTQVTVSS | | |
| 2-51: | (86) | LQLVESGGGLVQAGGSLRLSCAASGSTSGINLMAWYRQTSGKQRELVANIARGGLPKYGDSAKGRFTISRDSAKGRFTIYLQMRNLKPEDTAVYYCNAVLDWQLGDYWGQGTQVTVSS | | |
| 2-123: | (87) | QVQLVESGGGLVQPGGSLRLSCAASTSGFSFSDYYVNWFRQPPGKQHEVVASINPNGFTNYADSVKGRFTISRDNVKNAVYLQMNSLKPEDTALYYCHAVRISGGANYWGPGTQVTVSS | | |

FIG. 2 (Continued)

| NLX # | SEQ ID NO | Sequence (CDR1, CDR2, CDR3 underlined) |
|---|---|---|
| 2-141: | (88) | QVQLVESGGGLVQTGGSLRLSCAASGISFSDAAMGWYRQTPRKSREAVATIGNRGSVSYIDAVKGRFTISRDNAKNTLYLQMNSLEPEDTAVYYCRSFQEDLWGQGTQVTVSS |
| 3-8: | (89) | QVQLVESGGGLVQAGGSLRLSCTASGNTSGINIMAWYRQTSGKQREFLANIARGGLPKYSDSAKGRFTISRDNAKNTVHLQMNSLKPEDTAVYYCNALMDWRLGEYWGQGTQVTVSS |
| 3-33: | (90) | QVQLVESGGGLVQAGGSLRLSCVASGNTSGINIMAWYRQAPGKQRELVANKARGGLPKYADFAKGRFTISRDNAKNTVYLQMNMLKPEDTAVYYCNALMDWRLGEYWGQGTQVTVSS |
| 3-14: | (91) | QVQLVESGGGLVQAGGSLRLSCAASGSTSSINIMAWYRQASGKQRELVANKARGGLPKYADFAKGRFTVSRDNAKNTLYLQMNSLKPEDTAVYYCHALEDWALGEYWGQGTQVTVSS |
| 3-31: | (92) | QVQLVESGGGLVQAGGSLRLSCAASGSTSGINIMAWYRQASGKQRELVANKARGGLPKYADFAKGRFTVSRDNAKNTLYLQMNSLKPEDTAVYYCHALEDWALGEYWGQGTQVTVSS |
| 3-18: | (93) | QVQLVESGGGLAQAGGSLRLRLTCVASGNTSGINIMAWYRQTSGKQRELVANKARGGLPKYADSAKGRFTISRDNAKNTLYLQMNSLKPEDTGVYYCNALWDWALGEYWGQGTQVTVSS |
| 3-91: | (94) | QVQLVESGGGLVQAGGSLTLSCAASGNTSGINIMAWYRQASGKQREFLANIARGGLPKYSDSAKGRFTISRDNAKNTVYLQMNSLKPEDTAVYYCNAVMDWRLGEYWGQGTQVTVSS |
| 3-38: | (95) | QVQLVESGGGLVQAGGSLRLSCAASGSTSSINIMAWYRQVPGKQRELVANKARGGLPKYADFAKGRFTISRDNAKNTLYLQMNSLKPEDTAVYYCNAVMDWRLGEYWGQGTQVTVSS |
| 3-117: | (96) | QLQLVESGGGLVQAGGSLITLSCAASGNTSGINVMGWYRQTSGKQRELVANKARGGLPKYADFAKGRFTISRDNAKNTIYLQMNSLKPEDTAVYYCNAVMDWRLGEYWGQGTQVTVSS |
| 3-131: | (97) | QVQLVESGGGLVQAGGSLRLSCTASGNTSGINIMAWYRQTSGKQREFLANIARGGLPKYGDFAKGRFTISRDNAKNTVYLQMNSLKPEDTAVYYCNAVLDWRLGEYWGQGTQVTVSS |
| 3-51: | (98) | QLQLVESGGGLVQAGGSLRLSCIASGSTSDINVMAWYRQASGKQRELVANKARGGLPKYGDFAKGRFTISRDNAKNTIYLQMNDLKPEDTAVYYCNAVLDWRLGDYWGQGTQVTVSS |
| 3-68: | (99) | QVQLVESGGGLVQAGGSLRLSCVASGSTSDINIMAWYRQASGKQRELVANMARGGLPKYADSAKGRFTISRDNAKSTINLQMNDLKPEDTAVYYCNALLDWRLGEYWGQGTQVTVSS |

| CDR1 | (SEQ ID NO) | CDR2 | (SEQ ID NO) | CDR3 | (SEQ ID NO) |
|---|---|---|---|---|---|
| GNTSGINV | (1) | KARGGLP | (31) | NAVWDWALAEY | (40) |
| GDTSGINI | (2) | ITSAGTAS | (32) | NAVSDWKLGDY | (41) |
| GSTSDINI | (3) | ITTPGYT | (33) | NAVTDWALGDY | (42) |
| GSTSEINV | (4) | ITSAGYT | (34) | KAWDRDLVDY | (43) |
| GSTSEINI | (5) | IARGGLP | (35) | NALLDWRLGDY | (44) |
| GSIANIGG | (6) | INPNGFT | (36) | NAVWDWKLGDY | (45) |
| GSIANING | (7) | IGNRGSV | (37) | NAVTDWQLGDY | (46) |
| GSTSGINV | (8) | ITTFGYI | (38) | NALLDWRAGDY | (47) |
| GNTSGINI | (9) | MARGGLP | (39) | NALLDWALGEY | (48) |
| GSTSGINI | (10) | | | NAVLDWKLGEY | (49) |
| GSTSDINL | (11) | | | NAVWDWQLGDY | (50) |
| GSTPDINL | (12) | | | AAAEAYAEKYDY | (51) |
| GDTSDINV | (13) | | | NAVEDWRLGDY | (52) |
| GGSTSDINI | (14) | | | NAVLDWQLGDY | (53) |
| GRSTSDINI | (15) | | | HAVRISGGANY | (54) |
| SGNTSGINV | (16) | | | RSFQPDL | (55) |
| SGNTSGINI | (17) | | | NALWDWRLGEY | (56) |
| GSISSINV | (18) | | | HALEDWALGEY | (57) |
| RDIFSFNV | (19) | | | NALWDWALGEY | (58) |
| GSTSSINI | (20) | | | NAVWDWRLGEY | (59) |
| GSTSNINI | (21) | | | NAVLDWRLGDY | (60) |
| GSTSGINL | (22) | | | NALLDWRLGEY | (61) |
| TSGFSFSDY | (23) | | | | |
| GISFSDAA | (24) | | | | |
| GNTSGINL | (25) | | | | |
| GSTSSINI | (26) | | | | |
| GSTSGINI | (27) | | | | |
| GNTSGINI | (28) | | | | |
| GNTSGINV | (29) | | | | |
| GSTSDINV | (30) | | | | |

| sdAb | SEQ NO | CDR1 (SEQ NO) | CDR2 (SEQ NO) | CDR3 (SEQ NO) |
|---|---|---|---|---|
| 2-2 | 64 | GSTSDINI (3) | KARGGLP (31) | NAVSDWKLGDY (41) |
| 2-25 | 65 | GSTSDINI (3) | KARGGLP (31) | NAVTDWALGDY (42) |
| 2-33 | 68 | GSIANIGG (6) | ITSAGTAS (32) | KAWDRDLVDY (43) |
| 2-64 | 62 | GNTSGINV (1) | KARGGLP (31) | NAVWDWALAEY (40) |
| 2-69 | 71 | GNTSGINL (25) | IARGGLP (35) | NAVWDWKLGDY (45) |
| 2-90 | 70 | GSTSGINV (8) | KARGGLP (31) | NALLDWRLGDY (44) |
| 2-127 | 74 | GSTSDINI (3) | KARGGLP (31) | NAVTDWQLGDY (46) |
| 2-132 | 76 | GSTSDINL (11) | KARGGLP (31) | NALLDWRAGDY (47) |
| 3-32 | 80 | SGNTSGINV (16) | KARGGLP (31) | NAVWDWQLGDY (50) |
| 3-38 | 95 | GNTSGINL (25) | IARGGLP (35) | NAVWDWRLGEY (59) |

FIG. 4 sTF209 (SEQ ID NO: 100)

SGTTNTVAAYNLTWKSTNFKTILEWEPKPVNQVYTVQISTKSGDWKSKCFYTTDTECDLTDEIVKDVKQTYLARVFSYPAG
NVESTGSAGEPLYENSPEFTPYLETNLGQPTIQSFEQVGTKVNVTVEDERTLVRRNNTFLSRDVFGKDLIYTLYYWKSSS
SGKKTAKTNTNEFLIDVDKGENYCFSVQAVIPSRTVNRKSTDSPVEC sTF209-His (SEQ ID NO: 101)

masmSGTTNTVAAYNLTWKSTNFKTILEWEPKPVNQVYTVQISTKSGDWKSKCFYTTDTECDLTDEIVKDVKQTYLARVFS
YPAGNVESTGSAGEPLYENSPEFTPYLETNLGQPTIQSFEQVGTKVNVTVEDERTLVRNNTFLSRDVFGKDLIYTLYYW
KSSSSGKKTAKTNTNEFLIDVDKGENYCFSVQAVIPSRTVNRKSTDSPVECHHHHHH

FIG. 5A

1. sdAb-2-33-His (SEQ ID NO: 102)

maQVQLVESGGGLVQPGGSLTLSCAASGSIANIGGMAWYRRLPGNKRAMVASITSAGTASSYIDSVKGRFTISRDNAKN
   TVYLQMTSLKPEDTAVYLCKAWDRDLVDYWGQGIQVTVSSHHHHHH

2. sdAb-2-90-His (SEQ ID NO:103)

maQVQLVESGGGLVQAGGSLTLSCAASGSTSGINVMAWYRQAPGKQRELVANKARGGLPKYADFAKGRFTISRDNTKNT
   ISLQMNSLKPEDTAVYYCNALLDWRLGDYWGQGTQVTVSSHHHHHH

3. sTF₂₀₉-PC1-sdAb 2-33ᵣₗᵣ-His fusion protein (SEQ ID NO: 104)

masmSGTTNTVAAYNLTWKSTNFKTILEWEPKPVNQVYTVQISTKSGDWKSKCFYTTDTECDLTDEIVKDVKQTYLARV
   FSYPAGNVESTGSAGEPLYENSPEFTPYLETNLGQPTIQSFEQVGTKVNVTVEDERTLVRRNNTFLSLRDVFGKDLIYT
   LYWKSSSSGKKTAKTNTNEFLIDVDKGENYCFSVQAVIPSRTVNRKSTDSPVECGSGGGTGGGSGGGSGGGTGGGS<u>AI</u>
   <u>EPRSFSQN</u>QVQLVESGGGLVQPGGSLTLSCAASGSIANIGGMAWYRRLPGNKRAMVASITSAGTASSYIDSVKGRFTIS
   RDNAKNTVYLQMTSLKPEDTAVYLCKAWDRDLVDYWGQGIQVTVSSHHHHHH

4. sTF₂₀₉-PC1-sdAb 2-90ᵣₗᵣ-His fusion protein (SEQ ID NO: 105)

masmSGTTNTVAAYNLTWKSTNFKTILEWEPKPVNQVYTVQISTKSGDWKSKCFYTTDTECDLTDEIVKDVKQTYLARV
   FSYPAGNVESTGSAGEPLYENSPEFTPYLETNLGQPTIQSFEQVGTKVNVTVEDERTLVRRNNTFLSLRDVFGKDLIYT
   LYWKSSSSGKKTAKTNTNEFLIDVDKGENYCFSVQAVIPSRTVNRKSTDSPVECGSGGGTGGGSGGGSGGGTGGGS<u>AI</u>
   <u>EPRSFSQN</u>QVQLVESGGGLVQAGGSLTLSCAASGSTSGINVMAWYRQAPGKQRELVANKARGGLPKYADFAKGRFTISR
   DNTKNTISLQMNSLKPEDTAVYYCNALLDWRLGDYWGQGTQVTVSSHHHHHH

FIG. 5B 1. sTF$_{209}$-PC1-sdAb 2-33$_{TLT}$ fusion protein (SEQ ID NO: 106)

SGTTNTVAAYNLTWKSTNFKTILEWEPKPVNQVYTVQISTKSGDWKSKCFYTTDTECDLTDEIVKDVKQTYLARVFSYP
AGNVESTGSAGEPLYENSPEFTPYLETNLGQPTIQSFEQVGTKVNVTVEDERTLVRRNNTFLSLRDVFGKDLIYTLYYW
KSSSSGKKTAKTNTNEFLIDVDKGENYCFSVQAVIPSRTVNRKSTDSPVECGSSGGGTGGGSGGGTGGGSGGGTGGGSGATEPKS
ESQNQVQLVESGGGLVQPGGSLTLSCAASGSIANIGGMAWYRRLPGNKRAMVASITSAGTASSYIDSVKGRFTISRDNA
KNTVYLQMTSLKPEDTAVYLCKAWDRDLVDYWGQGIQVTVSS 2. sTF$_{209}$-PC1-sdAb 2-90$_{TLT}$ fusion protein (SEQ ID NO: 107)

SGTTNTVAAYNLTWKSTNFKTILEWEPKPVNQVYTVQISTKSGDWKSKCFYTTDTECDLTDEIVKDVKQTYLARVFSYP
AGNVESTGSAGEPLYENSPEFTPYLETNLGQPTIQSFEQVGTKVNVTVEDERTLVRRNNTFLSLRDVFGKDLIYTLYYW
KSSSSGKKTAKTNTNEFLIDVDKGENYCFSVQAVIPSRTVNRKSTDSPVECGSSGGGTGGGSGGGSGGGTGGGSGATEPKS
ESQNQVQLVESGGGLVQAGGSLTLSCAASGSTSGINVMAWYRQAPGKQRELVANKARGGLPKYADFAKGRFTISRDNTK
NTISLQMNSLKPEDTAVYYCNALLDWRLGDYWGQGTQVTVSS

FIG. 5C

1. sTF$_{209}$-sdAb 2-33$_{TLT}$ fusion protein (SEQ ID NO: 108)

SGTTNTVAAYNLTWKSTNFKTILEWEPKPVNQVYTVQISTKSGDWKSKCFYTTDTECDLTDEIVKDVKQTYLARVFSYP
AGNVESTGSAGEPLYENSPEFTPYLETNLGQPTIQSFEQVGTKVNVTVEDERTLVRRNNTFLSLRDVFGKDLIYTLYYW
KSSSSGKKTAKTNTNEFLIDVDKGENYCFSVQAVIPSRTVNRKSTDSPVECGSGGGTGGSGGGTGGGSGQVLVE
SGGGLVQPGGSLTLSCAASGSIANIGGMAWYRRLPGNKRAMVASITSAGTASSYIDSVKGRFTISRDNAKNTVYLQMTS
LKPEDTAVYLCKAWDRDLVDYWGQGIQVTVSS 2. sTF$_{209}$-sdAb 2-90$_{TLT}$ fusion protein (SEQ ID NO: 109)

SGTTNTVAAYNLTWKSTNFKTILEWEPKPVNQVYTVQISTKSGDWKSKCFYTTDTECDLTDEIVKDVKQTYLARVFSYP
AGNVESTGSAGEPLYENSPEFTPYLETNLGQPTIQSFEQVGTKVNVTVEDERTLVRRNNTFLSLRDVFGKDLIYTLYYW
KSSSSGKKTAKTNTNEFLIDVDKGENYCFSVQAVIPSRTVNRKSTDSPVECGSGGGTGGSGGGTGGGSGQVLVE
SGGGLVQAGGSLTLSCAASGSTSGINVMAWYRQAPGKQRELVANKARGGLPKYADFAKGRFTISRDNTKNTISLQMNSL
KPEDTAVYYCNALLDWRLGDYWGQGTQVTVSS

FIG. 5D

Full-length human tissue factor (SEQ ID NO: 110)

SGTTNTVAAYNLTWKSTNFKTILEWEPKPVNQVYTVQISTKSGDWKSKCFYTTDTECDLTDEIVKDVKQTYLARVF
SYPAGNVESTGSAGEPLYENSPEFTPYLETNLGQPTIQSFEQVGTKVNTFLSLRDVFGKDLI
YTLYYWKSSSSGKKTAKTNTNEEFLIDVDKGENYCFSVQAVIPSRTVNRKSTDSPVECMQEKGEFREIFYIIGAVV
FVVIILVITLAISLHKCRKAGVGQSWKENSPLNVS

FIG. 5E

1. sTF$_{209}$-PC2-sdAb 2-33$_{TLT}$ fusion protein (SEQ ID NO: 111)

SGTTNTVAAYNLTWKSTNFKTILEWEPKPVNQVYTVQISTKSGDWKSKCFYTTDTECDLTDEIVKDVKQTYLARVFSYP
AGNVESTGSAGEPLYENSPEFTPYLETNLGQPTIQSFEQVGTKVNVTVEDERTLVRRNNTFLSLRDVFGKDLIYTLYYW
KSSSSGKKTAKTNTNEFLIDVDKGENYCFSVQAVIPSRTVNRKSTDSPVECGSGGGTGGGSGGGSGGGTGGGSGGGSID
CRIVFCQVQLVESGGGLVQPGGSLTLSCAASGSIANIGGMAWYRRLPGNKRAMVASITSAGTASSYIDSVKGRFTISRD
NAKNTVYLQMTSLKPEDTAVYLCKAWDRDLVDYWGQGIQVTVSS

2. sTF$_{209}$-PC2-sdAb 2-90$_{TLT}$ fusion protein (SEQ ID NO: 112)

SGTTNTVAAYNLTWKSTNFKTILEWEPKPVNQVYTVQISTKSGDWKSKCFYTTDTECDLTDEIVKDVKQTYLARVFSYP
AGNVESTGSAGEPLYENSPEFTPYLETNLGQPTIQSFEQVGTKVNVTVEDERTLVRRNNTFLSLRDVFGKDLIYTLYYW
KSSSSGKKTAKTNTNEFLIDVDKGENYCFSVQAVIPSRTVNRKSTDSPVECGSGGGTGGGSGGGSGGGTGGGSGGGSID
CRIVFCQVQLVESGGGLVQAGGSLTLSCAASGSTSGINVMAWYRQAPGKQRELVANKARGGLPKYADFAKGRFTISRDN
TKNTISLQMNSLKPEDTAVYYCNALLDWRLGDYWGQGTQVTVSS

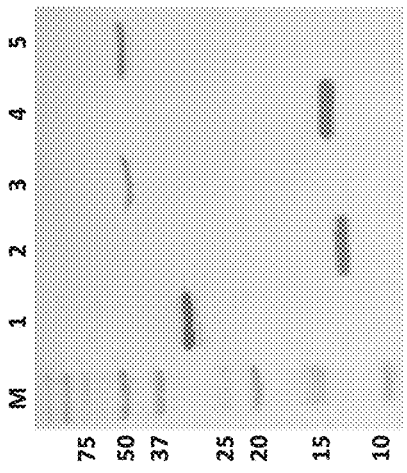
FIG. 8C
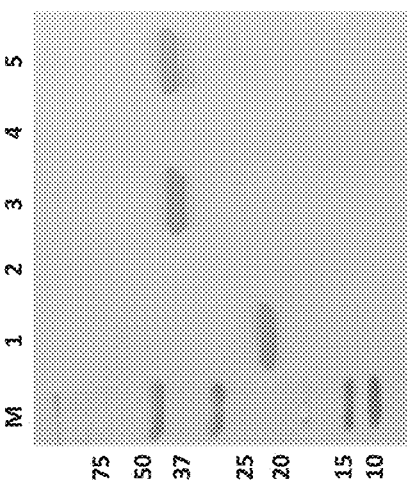
FIG. 8B
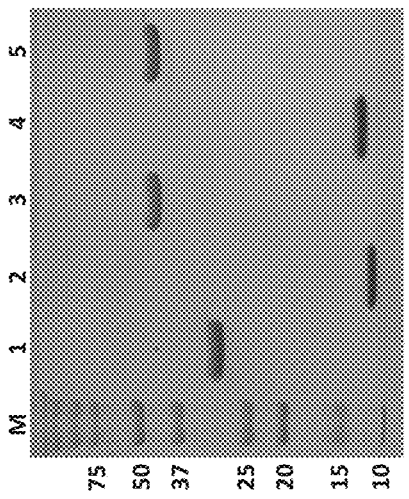
FIG. 8A
FIG. 8D

FUSION PROTEIN OF SINGLE DOMAIN ANTIBODY AND PROCOAGULANT

This application is a continuation of PCT/US2020/029599, filed Apr. 23, 2020; which claims the benefit of U.S. Provisional Application No. 62/844,610, filed May 7, 2019. The contents of the above-identified applications are incorporated herein by reference in their entirety.

REFERENCE TO SEQUENCE LISTING, TABLE OR COMPUTER PROGRAM

The Sequence Listing is concurrently submitted herewith with the specification as an ASCII formatted text file via EFS-Web with a file name of Sequence Listing.txt with a creation date of May 7, 2020, and a size of 87,400 bytes. The Sequence Listing filed via EFS-Web is part of the specification and is hereby incorporated in its entirety by reference herein.

FIELD OF THE INVENTION

The present invention relates to single domain antibodies (sdAbs) against TREM (triggering receptors expressed on myeloid cells) like transcript-1 (TLT-1) molecules that are present on activated platelets at the site of an injury, and especially on a subset of activated platelets, coated platelets. Furthermore, the present invention relates to fusion proteins comprising sdAbs and the extracellular (soluble) domain of tissue factor (sTF). Such fusion proteins direct sTF to activated platelets at the site of injury. Individuals that have a bleeding disorder, such as hemophilia A, hemophilia B, or acute bleeding due to traumatic injury are benefited from the treatment using such fusion proteins.

BACKGROUND OF THE INVENTION

Platelets normally circulate in blood flow in their resting stage. When blood vessels are injured, platelets interact with the damaged subendothelial cells via platelet glycoproteins (GP), such as GP Ib-IX-V and GP IIb/IIIa receptors, as well as tissue factor expressed there. This interaction initiates platelet adhesion, aggregation and activation at the site of injury as well as platelet shape change, and subsequent alpha- and dense-granule release. In addition to other membrane proteins, activated platelets express both P-selectin, that mediates interactions with leukocytes, and TLT-1 receptor, that enhances $Ca^{++}$ influx and promotes platelet aggregation on the surface when platelets get activated. However, TLT-1 receptor is found to be expressed exclusively on the surface of activated platelets, making it an ideal target molecule for coagulation factor localization, since activated platelets are almost exclusively found at a site of injury, though they have been implicated in some other disease states. Activated, 'coated' platelets (Dale, 2005, S. Thromb. Haemost. Volume 3 pp. 2185-2192) can be defined as expressing P-selectin, GPIIb/IIIa, and CD40L proteins, among others, on the platelet surface. (Yun et al., 2016, Biomed Res. Inter., volume 2016, e9060143). This population of activated platelets also induces flipping and exposure of membrane phosphatidylserine (PS) to their surface that serves to mediate interaction with coagulation proteins. This negatively-charged surface of PS-containing platelet-derived membranes plays a critical role in activating prothrombinase complex formation, the final step in the coagulation pathway that drives thrombin production, with subsequent fibrin formation.

Hemostasis is a natural clotting mechanism that takes place at the site of an injury to prevent excessive bleeding. The ideal therapeutic molecules for treating a bleeding disorder should only act at the site of injury and therefore localize coagulation factors there—this principle is a key to therapeutic practices in hemostasis. NOVOSEVEN® (Novo Nordisk, Denmark), a recombinant FVIIa (recFVIIa) molecule produced in cultured mammalian cells, has been a mainstay of biological molecules to treat patients with inhibitors of the coagulation factors FVIII and FIX; as such, molecules like recombinant FVIIa are referred to as "by-pass agents". Under normal hemostatic conditions, FVII circulating in blood is exposed to cell-bound tissue factor (TF) at sites of injury on the vascular adventitia, is activated by TF by their cooperative binding, and as part of the resulting complex, then cleaves FX to FXa. Recombinant FVIIa administration, as a stand-alone molecule, essentially "by-passes" the normal interaction of FVII and TF and acts on FX independently of tissue factor (that is primarily present and exposed only at the site of injury). However, to achieve this effect, FVIIa needs to be administered in pharmacologically large amounts in order to mimic the effects of natural FVII-TF activation (i.e. FX activation). Binding of recFVIIa to cell membranes, without interaction of TF, appears to be mediated by the exposure to phosphatidylserine in the lipid layer of activated platelets, and, much as plasma-derived FVII, mediates activation of FX through FVIIa active-site proteolysis. The high amounts of recFVIIa required for therapeutic efficacy in hemophilia A and B patients is believed to be due, at least in part, to low PS binding of the protein to platelets and a lack of cooperativity with TF. Other "bypass agents", like FEIBA (Baxter International), is composed of a mixture of plasma-derived coagulation factors, that includes only a small fraction of activated coagulation factors, like FVIIa, and can be used to treat hemophilia A and B patients with inhibitors; however, it is difficult to characterize this product due to the nature and variability of its diverse contents.

Rather than relying strictly on the properties of coagulation factors themselves, phosphatidylserine-binding proteins, such as annexin V and lactadherin C-2 proteins, have been considered as potential targeting vehicles to direct coagulation factors and other molecules to the lipid bilayers of activated platelets at a site of injury in order to accelerate clot production. Annexin V, for example, has high-affinity and high-specificity for PS in membranes (Thiagarajan and Tait, 1991, J. Biol. Chem., volume 266, pp. 24302-24307; Rescher and Gerke, 2004, J. Cell Sci., volume 117, pp. 2631-2639) making it ideal for targeting activated platelets. Fusion proteins that incorporate these domains with coagulation factors represent an alternative method for interaction with activated platelets but with a higher affinity than might be achieved with recFVIIa alone, for example. The extracellular domain of tissue factor fused to annexin V has been shown to be extremely potent in stemming blood flow in bleeding models (Huang et al., 2006, Blood, volume 107, pages 980-986) and represents a potential "by-pass" agent. Unfortunately, despite their potential utility, molecules like annexin V that specifically bind to PS have several downsides: phosphatidylserine can be expressed on non-platelet surfaces like apoptotic or dying cells, as well as other cell types, in addition to activated platelets, and PS-binding proteins or their fusions can compete with other coagulation factors for binding to PS on activated platelet surfaces and thereby limit coagulation processes (Thiagarajan and Tait, 1991, J. Biol. Chem., volume 266, pp. 24302-24307).

An alternative means for achieving high-affinity and high-specificity targeting to specific cell types is through antibodies. Monoclonal antibodies are used extensively to target therapeutic molecules to variety of the cells and platelets. These include both delivery of specific drugs to cancer targets (e.g., Yang et al., 2018, Biotechnol. Lett., volume 40, pp. 789-795; Khongorzul et al., 2020, Mol. Cancer Res., volume 18, pp. 3-19) or to damaged tissue (Runge et al., 1987, Proc. Natl. Acad. Sci. (USA), volume 84, pp. 7659-7662). In general, their large molecular size (150 kDa; even larger size as a fusion protein) and the constraints to their flexibility as a function of their complex heavy and light chain architecture and post-translational modifications, can lead to lower accessibility of some relevant target epitopes and relatively high production and purification costs, respectively, thereby limiting their use in developing therapeutically-useful fusion protein derivatives. In addition, their long plasma half-lives can be a detriment where short-lived and self-regulating attributes may be desired. In fact, few molecular fusions involving monoclonal antibodies have successfully been produced or used.

By contrast, single-domain antibodies (sdAbs), also known as nanobodies or domains, are antibodies that derive from heavy-chain-only antibodies present in sera of members of the family Camelidae (FIG. 1); similar sdAbs have also been identified in some members of the class Chondrichthyes. Camelid antibodies are devoid of the heavy-chain CH1 domain and thus do not support binding to a cognate light chain fragments as do other mammals. The variable domain of the heavy chain immunoglobulin (so-called VHH) is the smallest available intact antigen-binding domain derived from a functional immunoglobulin, ranging from 1.2-15 kDa in molecular weight. The VHH, unlike variable regions of other mammalian heavy and light chains, are able to intercalate or penetrate into domain clefts that are otherwise inaccessible to conventional antibodies or their derivatives that generally bind to epitopes on the surface of proteins (e.g., Schmitz et al., 2013, Structure, volume 21, pp. 1214-1224).

Tissue factor (TF), the primary initiator of coagulation, is a membrane-bound protein not normally expressed on the surface of cells in contact with the bloodstream. With vascular injury, subendothelial TF becomes exposed to blood flow and binds plasma factor VII. The resulting complex initiates an extrinsic cascade of coagulation activation steps, and specific enzymatic reactions, that ultimately culminate in clot formation and vascular sealing. Neither full-length TF, nor its soluble extracellular domain (sTF), can be used as a therapeutic molecule on its own. This is because, on the one hand, the potent and generalized activation of the coagulation system by full-length TF causes massive and disseminated thrombus formation that was already noted early in the twentieth century (Howell, 1912, Am. J. Physiol., volume 31, pages, p. 1-21). On the other hand, sTF is orders of magnitude less potent than the full-length form: membrane anchoring of TF is essential to support full proteolytic activity of FVIIa (Paborsky, 1991; Petrillo, 2010); as a result, sTF itself is essentially non-functional, especially at lower doses (Morrissey, U.S. Pat. No. 5,504,067).

Molecular agents to stem bleeding are critical for patients suffering from genetic diseases, like hemophilia A or B, but also from severe injuries, due to accidents, surgery or other traumatic events. Over the years, only an exceedingly small number of molecular entities have been created that are able to demonstrate efficacy in use in bleeding diathases, and even then, concern about potential excessive thrombotic side-effects, as well as drug costs, have made their use impractical.

There remains a considerable need to identify affordable and efficacious biological entities for treating bleeding disorders. Such entities will need to demonstrate critical attributes to fill in the areas of need beyond those served by normal or extended half-life coagulants, like long-acting FVIII or FIX, or to newer molecules, like more potent recombinant FVIIa molecules that appear to have untoward side-effects.

BRIEF DESCRIPTION OF THE DRAWINGS

FIG. 2 shows the amino acid sequences of the 38 anti-TLT-1 sdAb sequences, in which complementary determining regions, CDR1, CDR2 and CDR3, are highlighted.

FIG. 3A shows the amino acid sequences of CDR1, CDR2 and CDR3, of the 38 anti-TLT-1 sdAbs. FIG. 3B shows the specific CDR1, CDR2 and CDR3, of the 10 preferred anti-TLT-1 sdAbs.

FIG. 4 shows the amino acid sequence (1-209) of the extracellular domain of tissue factor (SEQ ID NO: 100), and the same sequence plus amino acids derived from the plasmid expression vector at N-terminal (lowercase letters) and a C-terminal His-6 tag at C-terminal (SEQ ID NO: 101)

FIG. 5A shows the amino acid sequences of sdAb-based proteins. Two anti-TLT-1 sdAb antibodies with a C-terminal His tag are shown: (1) sdAb-2-33-His (SEQ ID NO: 102) and (2) sdAb-2-90-His (SEQ ID NO: 103). Two fusion proteins with His tag are shown: (3) $sTF_{209}$-PC1-sdAb $2\text{-}33_{TLT}$-His (SEQ ID NO: 104) and (4) $sTF_{209}$-PC1-sdAb $2\text{-}90_{TLT}$-His (SEQ ID NO: 105). The linker sequence between the anti-TLT-1 sdAb and $sTF_{209}$ cassette includes a 22 amino acid Gly-Ser linker (underlined) from human transthyretin and a thrombin cleavage site (bolded) derived from human FVIII. In all cases, lowercase letters at the N-terminus indicate amino acids derived from the plasmid expression vector; uppercase letters indicate the primary sequence of the said protein.

FIG. 5B shows preferred amino acid sequences of TF fusions with anti-TLT-1 sdAbs. (1) $sTF_{209}$-PC1-sdAb $2\text{-}33_{TLT}$ (SEQ ID NO: 106) and (2) $sTF_{209}$-PC1-sdAb $2\text{-}33_{TLT}$ (SEQ ID NO: 107) containing a thrombin cleavage site proximal to the sdAb.

FIG. 5C shows the preferred sequences of the tissue factor-sdAb fusion proteins. (1) $sTF_{209}$-sdAb $2\text{-}33_{TLT}$ (SEQ ID NO: 108) and (2) $sTF_{209}$-sdAb $2\text{-}33_{TLT}$ (SEQ ID NO: 109), that do not contain a thrombin cleavage site.

FIG. 5D shows a full-length human tissue factor (SEQ ID 110) with the transmembrane domain highlighted.

FIG. 5E shows two fusion proteins with factor Xa cleavage site shown. (1) $sTF_{209}$-PC2-sdAb $2\text{-}33_{TLT}$-His (SEQ ID NO: 111) and (2) $sTF_{209}$-PC2-sdAb $2\text{-}90_{TLT}$-His (SEQ ID NO: 112). The linker sequence between the anti-TLT-1 sdAb and $sTF_{209}$ cassette includes a 22 amino acid Gly-Ser linker from human transthyretin and a human factor Xa cleavage site derived from human prothrombin.

FIGS. 8A-8D demonstrate the purity and molecular weight for recombinant proteins. (8A) A gel electropherogram of recombinantly-expressed sdAb 2-33 TLT-His (lane 2), sdAb 2-90 TLT-His (lane 4), sTF209-His (lane 1), sTF209-PC1-dAb 2-33 TLT-His (lane 3) and sTF209-PC1-sdAb 2-90 TLT-His (lane 5). Two micrograms of each protein were run onto a 15% SDS-PAGE gel and stained with Coomassie Brilliant Blue stain. (8B) A corresponding Western Blot for protein lanes 1, 2, 3, 4, and 5 in FIG. 8A. An anti-TF tag antibody was used to detect the protein in the Western blot. (8C) A corresponding Western Blot for protein lanes 1, 2, 3, 4, and 5 in FIG. 8A. An anti-His antibody was used to detect the protein in the Western blot. Lane M, Molecular weight marker (MW); Lane 1, sTF209-His; Lane 2, sdAb-2-33TLT-His; Lane 3, sTF209-PC1-sdAb 2-33TLT-His; Lane 4, sdAb 2-90TLT-His; Lane 5, STF209-PC1-sdAb 2-90TLT-His. (8D) A gel electropherogram of all ten recombinantly-expressed sdAbs shown in FIG. 3. Lane 1, sdAb 2-3TLT-His; Lane 2, sdAb 2-25TLT-His; Lane 3, sdAb 2-33TLT-His; Lane 4, sdAb 2-64TLT-His; Lane 5, sdAb 2-90TLT-His, Lane 6, sdAb 2-127TLT-His, Lane 7, sdAb 2-132TLT-His, Lane 8, sdAb 3-32TLT-His, Lane 9, sdAb 3-38TLT-His, Lane 10, sdAb 2-69TLT-His.

FIG. 14A shows the effect of fusion proteins on bleeding time and FIG. 14B shows the effect of fusion proteins for blood loss.

DETAILED DESCRIPTION OF THE INVENTION

Definitions

Figure 1:
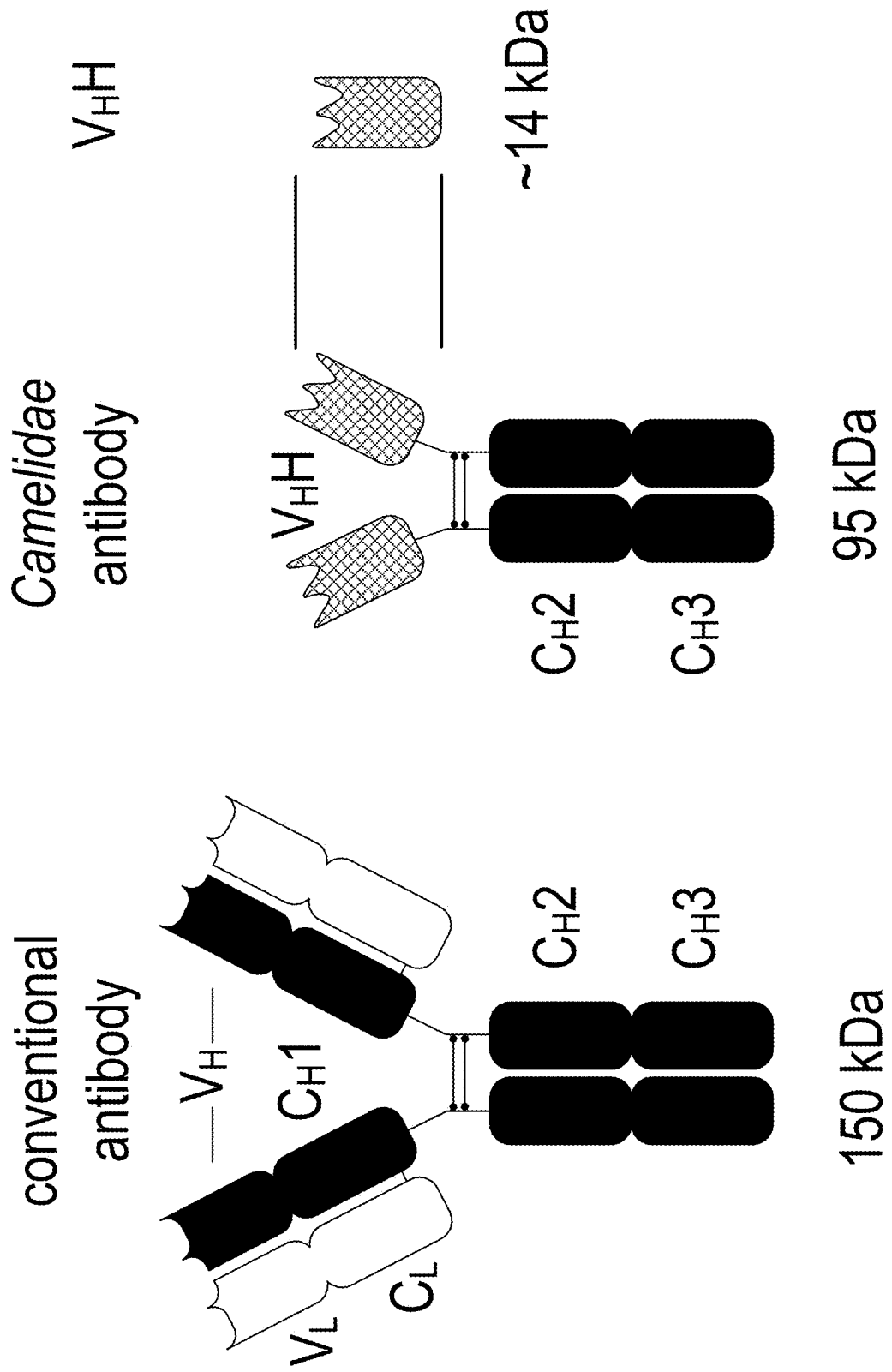
FIG. 1 illustrates the structures of conventional antibody, Camelidae antibody, and VHH. The conventional antibody is a four-polypeptide unit consisting of two identical heavy chains (H) and two identical light chains (L) held together by disulfide bonds to form the Y shape of the antibody and the N-terminal variable region (VH-VL) binds to the antigens. Camelid antibodies lacks a light chain and are composed of only two identical heavy chains, where the VHH domain (also known as sdAb or nanobody) binds the antigen.

"CDR"s are complementary-determining Regions of VH or VL chains of antibody which are critical for binding with antigen.

A "domain" means one region in a polypeptide which is folded into a particular structure independently of other regions.

A "single domain antibody" (sdAb), or a "variable domain of heavy chain of heavy-chain antibody" (VHH), also known as a nanobody, is an antibody fragment consisting of a single monomeric variable antibody, i.e., a variable domain of a heavy chain of an antibody. A single domain antibody is typically derived from the Camelidae family. VHH and sdAb are used interchangeably in this application.

A "tissue factor" (TF), also called platelet tissue factor, factor III, or CD142, is a membrane-bound protein encoded by the F3 gene, present in subendothelial tissue and leukocytes.

Its role in the clotting process is the initiation of thrombin formation from the zymogen prothrombin.

"TREM (triggering receptors expressed on myeloid cells) like transcript-1" (TLT-1), as used herein, is a membrane protein receptor found only in alpha-granules of platelets and megakaryocytes. TLT-1 contains an extracellular V-set Ig domain, a proline-rich region, and an immune receptor tyrosine-based inhibitory motif in its cytoplasmic tail. Upon platelet activation, TLT-1 is rapidly brought to the surface of platelets where it can enhance $Ca^{++}$ influx and promote platelet aggregation.

The present invention is directed to high-affinity single-domain antibodies (sdAb) that specifically bind both mouse and human TLT-1 proteins on activated, but not resting, platelets. Due to their smaller size, elevated stability, larger number of accessible epitopes, relatively low production costs and improved robustness, the inventors selected sdAb as targeting agents to prepare fusion proteins.

The present invention is also directed to fusion proteins comprising an extracellular (soluble) domain of tissue factor (sTF) linked to these single-domain antibodies for efficiently targeting sTF to sites of vascular injury. The targeting is through binding of the sdAbs to TLT-1, a membrane protein receptor confined exclusively to the alpha-granules of resting platelets and megakaryocytes that then translocates to the surface of platelets upon their activation; positioning of sTF for interaction with FVII is achieved on activated platelet membranes to promote procoagulant activity. This targeting maximizes TF's ability to function as a strong hemostatic agent, while minimizing the chance of inducing disseminated intravascular coagulation (DIC) by excess thrombin formation. The fusion proteins of present invention fulfill the needs to treating patients with severe bleeding disorders.

Single-Domain Antibodies (sdAb) against TLT-1 (TREM-Like Transcript 1)

TLT-1 (TREM-like transcript 1) protein is expressed selectively on the surface of activated platelets and contains a number of described grooves on its surface (Gattis et al., 2006, Proc. Natl. Acad. Sci. USA, volume 281, pp. 13396-13403). The inventors discovered that such characteristics making TLT-1 ideally suited for interacting with the single-domain antibodies. These surface grooves appear to contain amino acid residues with both negatively-charged and uncharged electrostatic properties that allow interaction with selected amino acids distinctly- and conformationally-displayed on sdAbs.

The inventors have prepared high-affinity single domain antibodies, that target TLT-1 protein. The inventors have generated a total of 103 sdAb, in which 38 sdAb sequences were identified. FIG. 2 shows the amino acid sequences of the 38 anti-TLT-1 sdAb sequences, in which complementary determining regions, CDR1, CDR2 and CDR3, are highlighted. FIG. 3A shows the CDRs (CDR1, CDR2, and CDR3) of the 38 anti-TLT-1 sdAb sequences. Ten preferred sdAb sequences with highest activities were selected by solid phase ligand binding assay and their sequences are SEQ ID NOs. 62, 64, 65, 68, 70, 71, 74, 76, 80, and 95. FIG. 3B shows the specific CDR1, CDR2 and CDR3, of the 10 preferred anti-TLT-1 sdAbs.

The present invention is directed to a single-domain antibody against TLT-1, comprising CDR1 selected from the group consisting of: SEQ ID NOs: 1-30, CDR2 selected from the group consisting of: SEQ ID NOs: 31-39, and CDR3 selected from the group consisting of: SEQ ID NOs: 40-61.

The present invention is also directed to a single domain antibody against TLT-1, comprising: (a) CDR1 being SEQ ID NO: 6, CDR2 being SEQ ID NO: 32, CDR3 being SEQ ID NO: 43; (b) CDR1 being SEQ ID NO: 8, CDR2 being SEQ ID NO: 31, CDR3 being SEQ ID NO: 44; (c) CDR1 being SEQ ID NO: 3, CDR2 being SEQ ID NO: 31, CDR3 being SEQ ID NO: 41; (d) CDR1 being SEQ ID NO: 3, CDR2 being SEQ ID NO: 31, CDR3 being SEQ ID NO: 42; (e) CDR1 being SEQ ID NO: 1, CDR2 being SEQ ID NO: 31, CDR3 being SEQ ID NO: 40; (f) CDR1 being SEQ ID NO: 25, CDR2 being SEQ ID NO: 35, CDR3 being SEQ ID NO: 45; (g) CDR1 being SEQ ID NO: 3, CDR2 being SEQ ID NO: 31, CDR3 being SEQ ID NO: 46; (h) CDR1 being SEQ ID NO: 11, CDR2 being SEQ ID NO: 31, CDR3 being SEQ ID NO: 47; (i) CDR1 being SEQ ID NO: 16, CDR2 being SEQ ID NO: 31, CDR3 being SEQ ID NO: 50; or (j) CDR1 being SEQ ID NO: 25, CDR2 being SEQ ID NO: 35, CDR3 being SEQ ID NO: 59. (FIG. 3B)

The present invention is further directed to a single domain antibody comprising the sequence selected from the group consisting of SEQ ID NOs: 62-99, or a sequence having at least 95%, or 96%, or 97%, or 98%, or 99% sequence identify thereof, provided that the sequence variations are in the non-CDR framework regions. Preferred single domain antibodies include those comprising the sequence selected from the group consisting of SEQ ID NOs: 62, 64, 65, 68, 70, 71, 74, 76, 80, and 95, preferably SEQ ID NOs. 68 and 70, or a sequence having at least 95%, or 96%, or 97%, or 98%, or 99% sequence identify thereof, provided that the sequence variations are in the non-CDR framework regions. The sequence variation, i.e., the amino acid changes are preferably of a minor amino acid change such as a conservative amino acid substitution. A conservative amino acid substitution is well known to a person skilled in the art.

The present invention provides single domain antibodies that interact both with human and mouse forms of the TLT-1 protein. Such antibodies are suitable for testing in both human and mouse models of bleeding, such as in transgenic mouse models of hemophilia or in acquired bleeding though inhibitors of coagulation pathways.

Fusion Proteins

The second aspect of the invention is directed to a fusion protein comprising (a) an extracellular domain of tissue factor, (b) a single domain antibody against TLT-1, and (c) a linker.

Activated platelets, and in particular, "coated" platelets, are substrates for numerous coagulation cascade components that, in combination with fibrinogen, are able to generate a fibrin-based clot needed to seal a vascular injury. By fusing sdAbs with the soluble domain of human tissue factor (sTF), the inventors have demonstrated the targeting of these protein fusions to activated platelets directly and specifically. This specific targeting thus "bypasses" the normal coagulation cascade much in the way of a recombinant FVIIa. Mechanistically, however, the two 'bypass agents' are very different. For the chimeric sTF-sdAb fusions, the extracellular portion of TF becomes anchored to activated platelets through the insertion of a high-affinity sdAb fusion partner into relevant epitope folds of the TLT-1 protein; in the correct surface orientation, the sTF domain is thermodynamically-favored to bind to circulating plasma FVII, and activates it in situ to FVIIa; factor VIIa in turns activates FX to FXa, and further stimulates and promotes the common coagulation cascade. This mechanism is considerably different than the mechanics of recombinant FVIIa activation of coagulation factors and direct platelet binding.

The amino acid sequence of full length of human tissue factor protein is shown in FIG. 5D (SEQ ID NO: 110). In the fusion protein of the present invention, the extracellular domain of tissue factor (sTF) is selected from amino acid residues 1-208 to 1-221, or 1-209 to 1-220 of SEQ ID NO: 110. For example, sTF is 1-208, 1-209, 1-210, 1-211, 1-212, 1-213, 1-214, 1-215, 1-216, 1-217, 1-218, 1-219, 1-220, or 1-221 of SEQ ID NO: 110. A preferred sTF is 1-209 of SEQ ID NO: 110.

In the fusion protein of the present invention, the sdAb is any sdAb described above in the preceding sections.

In the fusion protein of the present invention, the sdAb may be C-terminal or N-terminal to the sTF, and a flexible linker is used to connect the sdAb with the soluble tissue factor. A flexible linker can be any length that links the two proteins, spaces the two protein properly, and does not affect the functionality of the two proteins. The length of linker sequence can be optimized in order to allow ideal positioning sTF of the fusion molecule on the surface of the platelet, as a function of its insertion into the TLT-1 molecule, to efficiently bind FVII, which is the first step in propagating the extrinsic coagulation pathway. The length of the linker sequence is in general 5-40, 10-30, or 15-30 amino acids, preferably the length of the linker is 18-26 amino acids.

A flexible linker may contain a variety of amino acids. In one embodiment, a flexible linker comprises various combinations of glycine and serine, as well as other amino acids, such as threonine. For example, a flexible linker can be a natural amino acid sequence derived from a human transthyretin protein such as GSGGGTGGGSGGSGGGTGGGSG (SEQ ID NO: 113). For example, the flexible linker can be an artificial sequence such as GGGGSGGGGSGGGGS (SEQ ID NO: 114).

Figure 6B:
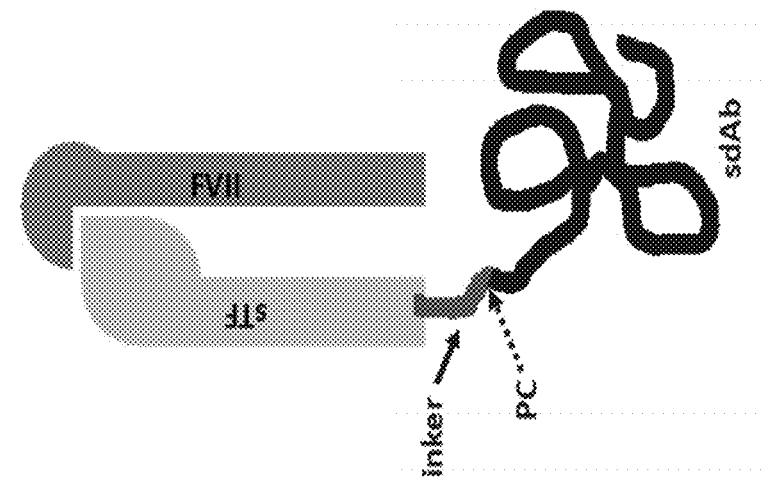
FIGS. 6A-6B show schematic representation of fusion proteins of soluble domain of tissue factor (sTF) and single domain antibody (sdAB). (6A) The C-terminus of the sTF$_{209}$ is fused to the N-terminus of an sdAb through a flexible polypeptide sequence containing a Gly-Ser linker and FVIII thrombin cleavage site; the figure is based on crystal structures of sTF and a camelid sdAb. (6B) Stick figure representation of the similar structure in (A) but indicating the interaction of sTF with FVII after binding of sdAb to TLT-1 protein on the surface of activated platelets. 'PC' indicates the position of a proteolytic cleavage site.
Figure 6A:
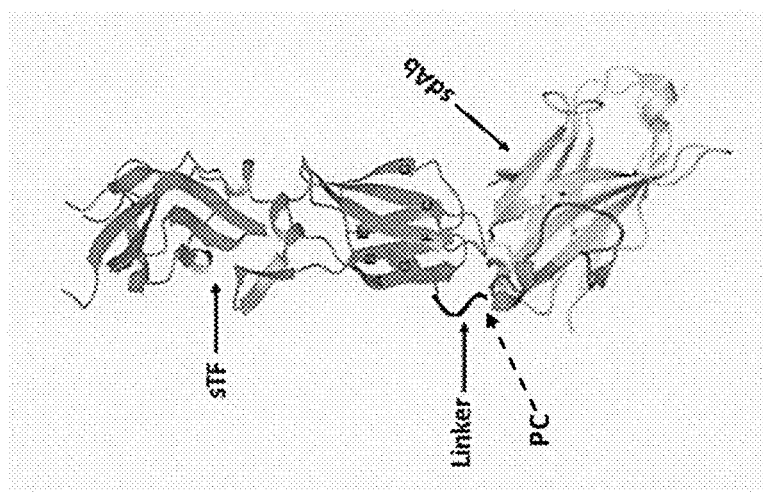

In one embodiment, the fusion protein of the present invention may further comprise a protease cleavage site. In this embodiment, the fusion protein comprises: (a) an extracellular domain of tissue factor, (b) a single domain antibody against TLT-1, (c) a linker, and (d) a polypeptide sequence that can be proteolytically-cleaved by a protease. The polypeptide sequence of (d) includes, but not limited to, a thrombin cleavage site, a FXa cleavage site, or a FXIa cleavage site, to allow auto-regulation of thrombin production (FIG. 6). For example, a thrombin cleavage site may comprise the amino acid sequence of AIEPRSFSQN (SEQ ID NO: 115). For example, a FXa cleavage site may comprise the amino acid sequence of LESYIDGRIVEG (SEQ ID NO: 116) or SDRAIEGRTATS (SEQ ID 117). The proteolytic cleavage site may be located at the C-terminus or N-terminal of the flexible linker. The proteolytic cleavage site may also be located inside of the flexible linker. Introduction of a protease cleavage site allows thrombin generated by FXa/FII complex in the vicinity of the sTF-sdAb fusion to access this linker and separate the two fusion partners, namely, the TLT-1 sdAb from the sTF domain; neither fusion partner alone is functionally-active. This self-limiting mechanism will prevent excess thrombin generation and dramatically increase the safety margin upon administration of the fusion protein to patients.

In one embodiment, the present invention provides nucleotide sequences encoding the fusion proteins of the present invention. The nucleotide sequences allow inclusion as part of a prokaryotic, fungal, or eukaryotic expression vector for expression in bacterial cells (like *Escherichia coli*), yeast (like *Saccharomyces cerevisiae*), insect cells (like Sf9, Sf21 and High Five), or mammalian cells (like CHO, HEK, BHK, for example), respectively. Due to the small size of the sdAb, the fusion protein can be expressed in bacteria, yeast, insect cells or other eukaryotic cells, such as mammalian cells.

In a further aspect, the present invention provides a pharmaceutical composition comprising the fusion protein of the present invention and a pharmaceutically acceptable carrier. In a further aspect, the present invention provides a method for treating bleeding disorders, such as those of congenital or acquired coagulopathies, traumatic bleeding due to injury, or other uses where bleeding cannot easily be controlled. The method comprises the step of administering an effective amount of the fusion protein of the present invention to a patient in need thereof with. The fusion protein, for example, can be administered by injection or other parenteral administration, or by oral administration.

The fusion protein of the present invention avidly, and specifically, binds to TLT-1 molecules on activated platelets. This binding to TLT-1 then conformationally-promotes interaction of sTF to FVII, the molecule that, when activated, further facilitates the downstream common coagulation cascade leading to thrombin formation. The resulting fusion protein exhibits the desired properties of a functional procoagulant: high-affinity binding to activated platelets, high-affinity binding to FVII and conversion to FVIIa, conversion of factor X to factor Xa, and incorporation of a proteolytic (thrombin) cleavage site to self-limit excess thrombin formation. Cleavage allows selective dissociation of the sTF domain (domain responsible for FVII activation but only when bound as a fusion) from the sdAb antibody domain that binds TLT-1 on the activated platelet (these domains do not promote coagulation or platelet aggregation in any case). The fusion proteins optionally have a hexanucleotide His tag incorporated at their C-terminus to facilitate purification and detection.

The inventors have demonstrated two high-affinity sdAb domains, sdAb 2-33$_{TLT}$ (SEQ ID: 68) and sdAb 2-90$_{TLT}$ (SEQ ID: 70), to act as fusion partners with the extracellular domain of tissue factor (amino acid 1-209 of SEQ ID NO: 100). The resulting preferred fusion molecules, named sTF$_{209}$-PC1-sdAb 2-33$_{TLT}$ (SEQ ID: 106) and sTF$_{209}$-PC1-sdAb 2-90$_{TLT}$ SEQ ID: 107), bind efficiently to both mouse and human platelets through the interaction with the platelet TLT-1 receptor. They effectively bind to FVIIa to promote the generation of FXa from FX, to generate formation of thrombin (FIIa) from prothrombin, and to reduce blood loss in a mouse model of bleeding. On the other hand, neither the sTF domain alone, nor the sdAb antibody domain alone, nor sTF-sdAb fusion protein is able to mediate platelet aggregation or activation at the tested dose.

The following examples further illustrate the present invention. These examples are intended merely to be illustrative of the present invention and are not to be construed as being limiting.

EXAMPLES

TABLE 1

Abbreviations

| Abbreviation Name | Description |
|---|---|
| TLT-1 | TREM-like transcript-1 |
| sdAb | Single domain antibody |
| sTF | Tissue factor extracellular (soluble) domain |
| VHH | Variable domain of the heavy chain immunoglobulin |
| FVIIa | Activated factor VII |
| CHO | Chinese hamster ovary |
| BHK | Baby Hamster Kidney |
| HEK | Human embryonic kidney |
| SEQ | Sequence |
| CDR | Complementary determining regions |
| PBMC | Peripheral blood mononuclear cell |
| GLY | Glycine |
| SER | Serine |
| HIS | Histidine |
| PC1 | Thrombin cleavage site |
| PC2 | Factor Xa cleavage site |

Example 1: Human TLT-1 Amino Acid Sequence

The amino acid sequence of human TLT-1, an abundant platelet type I transmembrane receptor with an immunoglobulin-like structure, is presented below; the underlined sequence is the signal sequence at the N-terminus of the protein and the highlighted sequence is the TLT-1 transmembrane domain. The extracellular domain of human ILT-1 that was used in generation of the anti-TLT-1 single domain antibodies (sdAbs) is a 147 amino acid protein between the end of the signal sequence and the beginning of the transmembrane domain (underlined), UniProt sequence Q86YW5:

(SEQ ID NO: 118)

MGLTLLLLLLLGLEGQGIVGSLPEVLQAPVGSSILVQCHYRLQDVKAQKV

WCRFLPEGCQPLVSSAVDRRAPAGRRTFLTDLGGGLLQVEMVTLQEEDAG

EYGCMVDGARGPQILHRVSLNILPPEEEEETHKIGSLAENAFSDPAGSAN

PLEPSQDEKSIPLIWGAVLLVGLLVAAVVLFAVMAKRKQGNRLGVCGRFL

-continued

SSRVSGMNPSSVVHHVSDSGPAAELPLDVPHIRLDSPPSFDNTTYTSLPL

DSPSGKPSLPAPSSLPPLPPKVLVCSKPVTYATVIFPGGNKGGGTSCGPA

QNPPNNQTPSS

Example 2. Generation of Anti-Human TLT-41 Single Domain Antibodies (sdAbs)

In order to create coagulation co-factors targeting specific proteins on platelets, the inventors first identified sdAb antibodies specific for human TLT-1 by immunizing llamas five times with recombinant, soluble human TLT-1 protein and recovering the mRNAs coding for the heavy-chain antibody fragments from the B-cells of the immunized llamas. Messenger RNAs were converted into complementary DNA (cDNA) and cloned into a major coat protein gene (pIII) of bacteriophage M13 for expression. VHH domains of interest were selected by phage display methods (e.g., Kushwaha et al., 2014, J. Vis. Exp., volume 84, e50685; Saw and Song, 2019, Protein Cell, volume 10, pp. 787-807). The recovered sdAbs were selected from the pool of antibody fragments by binding repeatedly to immobilized human TLT-1 protein, as well as to unrelated proteins; repeated selection by this method identified only those that were true and high-affinity binders to TLT-1, while non-specific binders were discarded. DNA sequencing and sequence alignment were used to validate the structure and sequence of the resulting specific sdAb. Further characterization of potential candidates was made by testing of binding of individual sdAb expressed in, and purified from, bacterial cells to full-length, membrane-bound human recombinant TLT-1 that was transfected into, and expressed on the surface of, Chinese hamster ovary (CHO) cells and on both resting and activated platelets using Flow cytometry to demonstrate specificity and functional binding of sdAbs. Finally, select sdAbs were tested as fusions with sTF to determine their ability to reduce blood loss in animal models of bleeding.

Animal Immunization

One llama was immunized subcutaneously at 3-week intervals and at multiple site of injection. Over the course of 5 rounds of injections with 0.5-1.0 mg of human TLT-1-His antigen (encompassing the TLT-1 extracellular domain shown in FIG. 1, but with the addition of hexahistidine tag; Sino Biological US, PA), the antibody titer against this antigen increased from undetectable to 1:12,800 which indicates a high-titer response to the injected antigen.

Immune Library Construction and Screening

After the immunization protocol was completed, whole blood was collected from the immunized llama for PBMC isolation. RNA was extracted and tested by gel electrophoresis to be intact. The VHH genes of immunoglobulin RNA were amplified by two rounds of PCR after reverse transcription using unique primers to camelid variable and constant region domain sequences. The PCR products and the phagemid DNA were digested with Sfi I restriction site endonuclease and ligated together with T4 DNA ligase. The ligation mix was transformed into *E. coli* TG1 cells. The final constructed library consisted of $5.2\times10^8$ independent members. Three rounds of bio-panning for single-domain binders against TLT-1-His protein was then performed and an enriching factor of about a thousand-fold was achieved.

Binder Validation

Based on the bio-panning strategy, a total of 300 clones were validated against TLT-1 using ELISA and, of these, 147 clones were identified as positive. DNA sequence indicated that 145 of 147 clones were correctly identified as authentic camelid antibodies. A total of 103 unique clones have been identified at the amino acid level. As some groups of the identified unique clones present the same CDR3 region but have differences in their CDR1 and/or CDR2 regions, these unique sequences were further analyzed based on their CDR3 regions (the CDR regions are predicted via IMGT database). A total of 38 unique sdAb sequences with different CDR1, CDR2, and/or CDR3 were identified (FIG. 2 and FIG. 3). From the 38 sdAbs, the top 10 clones with the highest clone frequency were re-tested by ELISA (Table 1). Data demonstrated strong positive signals compared with the negative control protein.

ELISA Ligand Binding Assay

The top 10 clones were then confirmed in the final soluble ELISA validation. Soluble TLT-1 extracellular domain His tag (sTLT-1-His) protein was coated (0.1 µg/well) onto a 96-well plate and incubated overnight at 4° C. An irrelevant protein with His tag and an no coating group were used in the assay as negative controls. On the next day, the coated plate was washed 3 times with 200 µL PBST buffer per well and blocked with 300 µL blocking buffer per well for 1 h at 37° C. The blocking buffer was then removed and the plate was washed 3 times with the washing buffer. After washing, 100 µL of HRP-anti-TLT-1 sdAb antibody in blocking buffer was added to each well and incubated at 37° C. for 1 h. The plate was washed three times with the washing buffer and then 100 µL of TMB substrate solution was added per well and incubated at room temperature for 15 minutes; 100 µL of 2M $H_2SO_4$ were then added to stop the reaction and the plate was analyzed using a microplate reader at 490 nm. According to the results, consistent results were obtained. In the meantime, the negative control groups present expected low signal, which indicated all the Top 10 clones did not cross-react with His tag and can bind to the target specifically.

TABLE 2

[OD 490 nm]

| Clone | Coating: TLT-1 protein (3 µg/mL) | Coating: Irrelevant protein (3 µg/mL) | No Coating |
|---|---|---|---|
| 2-2 | 0.796 | 0.103 | 0.096 |
| 2-25 | 0.512 | 0.073 | 0.104 |
| 2-33 | 1.501 | 0.070 | 0.095 |
| 2-64 | 0.911 | 0.066 | 0.104 |
| 2-69 | 0.494 | 0.076 | 0.099 |
| 2-90 | 0.762 | 0.081 | 0.132 |
| 2-127 | 0.760 | 0.076 | 0.102 |
| 2-132 | 0.981 | 0.114 | 0.079 |
| 3-32 | 0.858 | 0.097 | 0.106 |
| 3-38 | 0.818 | 0.087 | 0.099 |

Figure 7A:
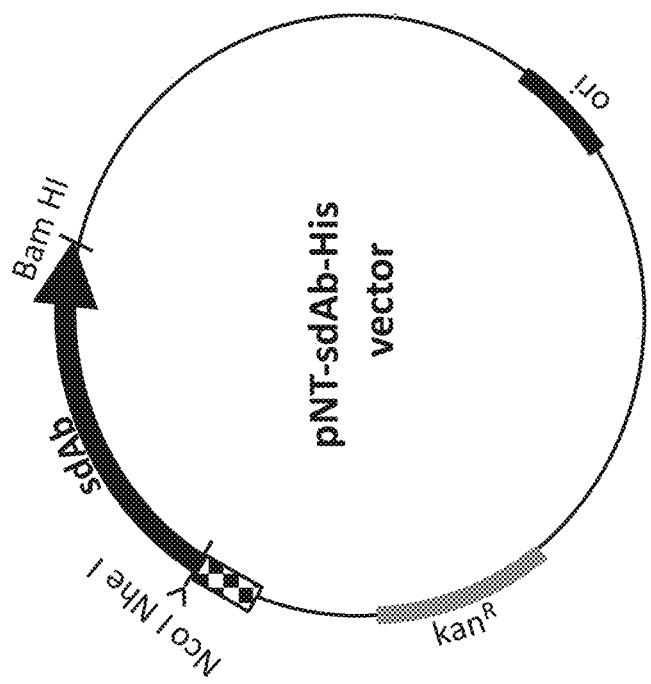
FIGS. 7A-7C represent plasmid maps for the expression of anti TLT-1 sdAbs, sTF and sTF-sdAb fusion proteins. DNAs corresponding to each protein was subcloned into specified restriction enzyme cleavage sites and expressed under a T7 promoter (stippled box). (7A) Plasmid map for the expression vectors pNT-sdAb 2-33$_{TLT}$ and pNT-sdAb 2-90$_{TLT}$. The expression cassettes contain the DNA sequence encoding sdAb 2-33$_{TLT}$-His or sdAb 2-90$_{TLT}$-His with a C-terminal His-tag. The cloning sites are Nco I and Bam HI. (7B) Plasmid map for the expression vector pNT-sTF$_{209}$-His. The expression cassette contains the DNA sequence encoding extracellular domain of tissue factor amino acid 1-209 (sTF$_{209}$) with a C-terminal His-tag. The cloning sites are Nhe I and Bam HI. (7C) Plasmid map for the expression vector pNT-sTF$_{209}$-PC-sdAb 2-33$_{TLT}$-His and pNT-sTF$_{209}$-PC-sdAb 2-90$_{TLT}$-His. The expression cassette contains the DNA sequence encoding sTF$_{209}$ and either sdAb 2-33$_{TLT}$ or sdAb 2-90$_{TLT}$ proteins containing a C-terminal His-tag; 'PC' indicates the presence of a proteolytic cleavage site at the C-terminal side of the Gly-Ser linker. The cloning sites for the DNA cassettes are Nhe I and Bam HI.

Example 3. Development of pNT-sdAb 2-33$_{TLT}$-His, pNT-sdAb 2-132$_{TLT}$-His, pNT-sdAb 2-25$_{TLT}$-His, pNT-sdAb 2-64$_{TLT}$-His, pNT-sdAb 2-90$_{TLT}$-His, pNT-sdAb 2-127$_{TLT}$-His, pNT-sdAb 2-2$_{TLT}$-His, pNT-sdAb 3-32$_{TLT}$-His, pNT-sdAb 3-38$_{TLT}$-His and pNT-sdAb 2-69$_{TLT}$-His Expression Constructs In order to evaluate the utility of these novel antibodies, DNAs corresponding to ten selected single-domain antibodies identified in TABLE 1 were synthesized and codon-optimized for bacterial expression (GenScript, Piscataway N.J.); corresponding amino acid sequences and SEQ ID numbers are shown in FIG. 2. A Nco I restriction enzyme site at the 5'-end and a Bam HI restriction enzyme site at the 3'-end were included for cloning purposes. To facilitate recombinant sdAb purification, a sequence encoding six histidine amino acids (His) was also incorporated at the 3'-end of the synthesized genes upstream of the Bam HI site. The synthesized genes were inserted into Nco I and Bam HI restriction enzyme sites of a pNT-based plasmid expression vector. The resulting vectors were designated as pNT-sdAb 2-33$_{TLT}$-His, pNT-sdAb 2-132$_{TLT}$-His, pNT-sdAb 2-25$_{TLT}$, pNT-sdAb 2-64$_{TLT}$-His, pNT-sdAb 2-90$_{TLT}$-His, pNT-sdAb 2-127$_{TLT}$-His, pNT-sdAb 2-2$_{TLT}$-His, pNT-sdAb 3-32$_{TLT}$-His, pNT-sdAb 3-38$_{TLT}$-His and PNT-sdAb 2-69$_{TLT}$-His (TABLE 2). A representative illustration of the plasmid expression vector for the anti-TLT-sdAbs and sTF-sdAbs fusions is shown in FIG. 7A.

Example 4. Development of pNT-sTF$_{209}$-His Expression Construct

Figure 7B:
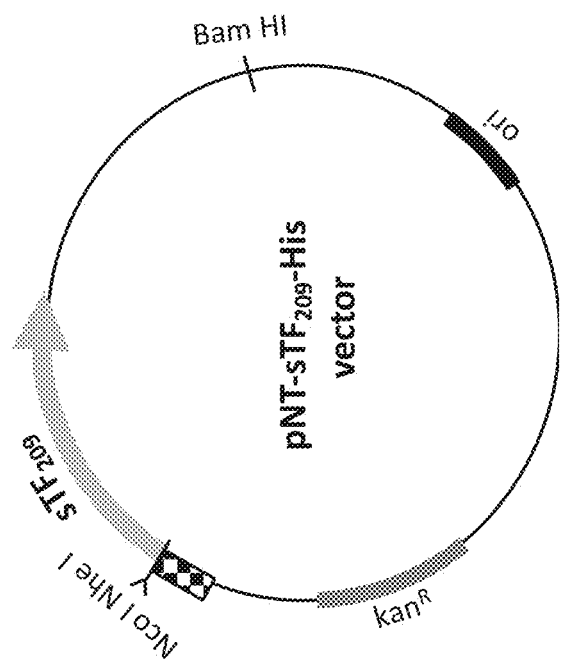

DNA corresponding to the extracellular domain of tissue factor (sTF) amino acid 1-209 was synthesized as previously described and codon-optimized for expression in bacteria. A Nhe I restriction enzyme site at the 5'-end and a Bam HI restriction enzyme site at the 3'-end were included for cloning purposes. To facilitate recombinant sTF purification, a sequence encoding six histidine amino acids (His) was also incorporated at the 3'-end of the synthesized genes upstream of the Bam HI site. The synthesized sTF209-His was inserted into Nhe I and Bam HI restriction enzyme sites of a pNT-based expression vector and the resulting vector was designated as pNT-sTF$_{209}$-His (TABLE 2). A representative illustration of the plasmid expression vector for the extracellular domain of soluble tissue factor (sTF) is shown in FIG. 7B.

Figure 7C:
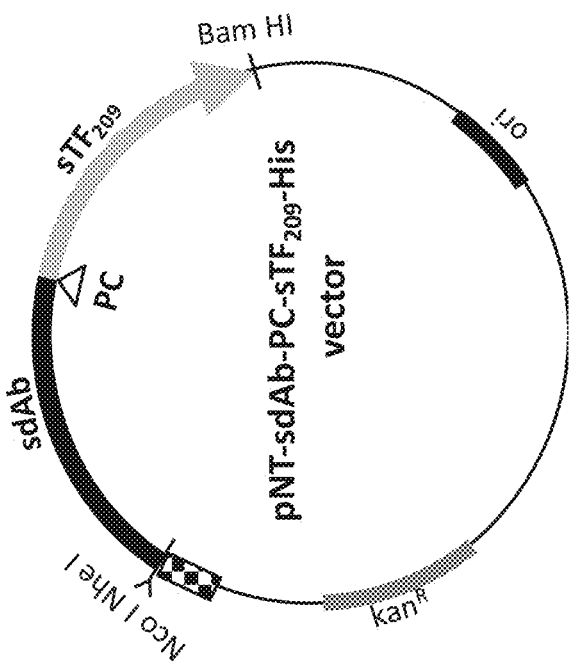

Example 5. Development of pNT-sTF$_{209}$-PC1-sdAb 2-33$_{TLT}$ and pNT-sTF$_{209}$-PC1-sdAb 2-90$_{TLT}$ Expression Constructs The expression cassettes encoding sTF$_{209}$-PC1-sdAb 2-33$_{TLT}$-His and sTF$_{209}$-PC1-sdAb 2-90$_{TLT}$-His were synthesized (GenScript, Piscataway N.J.) and codon-optimized for bacterial expression. A Nhe I restriction enzyme site at the 5'-end and a Bam HI restriction enzyme site at the 3'-end were included for cloning purposes. To facilitate purification of the recombinant fusion proteins, a sequence encoding six histidine amino acids (His) was also incorporated at the 3'-end of the synthesized genes upstream of the Bam HI site. To properly position sTF on the surface of the cell surface and to limit thrombin overexpression, a Gly-Ser linker sequence from human transthyretin (encoding 22 amino acids) and a thrombin cleavage site from human factor VIII ('PCI'), respectively, were inserted between the sTF and sdAb sequences. The synthesized genes were inserted into Nhe I and Bam HI restriction enzyme sites of a pNT expression vector, itself based on the pET9d plasmid vector. The resulting vectors were designated as pNT-sTF$_{209}$-PC1-sdAb 2-33$_{TLT}$-His and pNT-sTF209-PC1-sdAb 2-90$_{TLT}$-His, respectively (Table 3). A representative illustration of the plasmid expression vector for the sTF-sdAb fusions is shown in FIG. 7C.

TABLE 3

| Expression Construct | Name | Coding Protein Description |
|---|---|---|
| 1 | pNT-sdAb 2-33$_{TLT}$-His | sdAb 2-33$_{TLT}$-His |
| 2 | pNT-sdAb 2-132$_{TLT}$-His | sdAb 2-132$_{TLT}$-His |
| 3 | pNT-sdAb 2-25$_{TLT}$-His | sdAb 2-25$_{TLT}$-His |
| 4 | pNT-sdAb 2-64$_{TLT}$-His | sdAb 2-64$_{TLT}$-His |
| 5 | pNT-sdAb 2-90$_{TLT}$-His | sdAb 2-90$_{TLT}$-His |
| 6 | pNT-sdAb 2-127$_{TLT}$-His | sdAb 2-127$_{TLT}$-His |
| 7 | pNT-sdAb 2-2$_{TLT}$-His | sdAb 2-2$_{TLT}$-His |
| 8 | pNT-sdAb 3-32$_{TLT}$-His | sdAb 2-32$_{TLT}$-His |
| 9 | pNT-sdAb 3-38$_{TLT}$-His | dAb 2-38$_{TLT}$-His |
| 10 | pNT-sdAb 2-69$_{TLT}$-His | sdAb 2-69$_{TLT}$-His |
| 11 | pNT-sTF$_{209}$-His | sTF$_{209}$-His |
| 12 | pNT- sTF$_{209}$-PC1-sdAb 2-33$_{TLT}$-His | sTF$_{209}$-PC1-sdAb 2-33$_{TLT}$-His fusion |
| 13 | pNT- sTF$_{209}$-PC1-sdAb 2-90$_{TLT}$-His | sTF$_{209}$-PC1-sdAb 2-90$_{TLT}$-His fusion |

Example 6. Expression and Purification of Recombinant sTF$_{209}$, TLT-1 sdAbs and sTF$_{209}$-sdAb Fusion Proteins Expressed in Bacteria All ten sdAbs, as well as sTF$_{209}$, and the two sTF$_{209}$-sdAb fusion protein DNA sequences described in TABLE 2 were chemically-transformed into an *E. coli* BL21-based bacteria strain and expressed in LB medium. The bacteria were harvested after protein expression and sonicated in lysis buffer (20 mM HEPES pH 8.0, 300 mM KCl and 10% glycerol). The supernatants were then collected by high-speed centrifugation and applied to a His-Trap HP column (GE) for His-tag protein purification using GE AKTA chromatography system. After washing with 20 column volumes of washing buffer (20 mM HEPES pH 8.0, 20 mM imidazole, 300 mM KCl and 10% glycerol), the absorbed proteins were eluted by using gradient elution buffer (20 mM HEPES pH 8.0, 40-300 mM imidazole, 300 mM KCl and 10% glycerol). Fluted proteins were then concentrated and buffer exchanged into PBS buffer. The purified proteins were analyzed using 10% SDS-PAGE method and confirmed with Western blot. FIG. 5A (SDS-PAGE), FIG. 8B (Western blot of FIG. 8A with anti-TF antibody) and FIG. 8C (Western blot of FIG. 8A with anti-His antibody) demonstrate the quality of the purified sdAb 2-33$_{TLT}$-His, sdAb 2-90$_{TLT}$-His, sTF$_{209}$-PC1-sdAb 2-33$_{TLT}$-His, sTF$_{209}$-PC1-sdAb 2-90$_{TLT}$-His and sTF$_{209}$-His proteins; all proteins are present as single bands and display the expected molecular weight. FIG. 8D demonstrates purified ten sdAbs on SDS-PAGE.

Figure 9A:
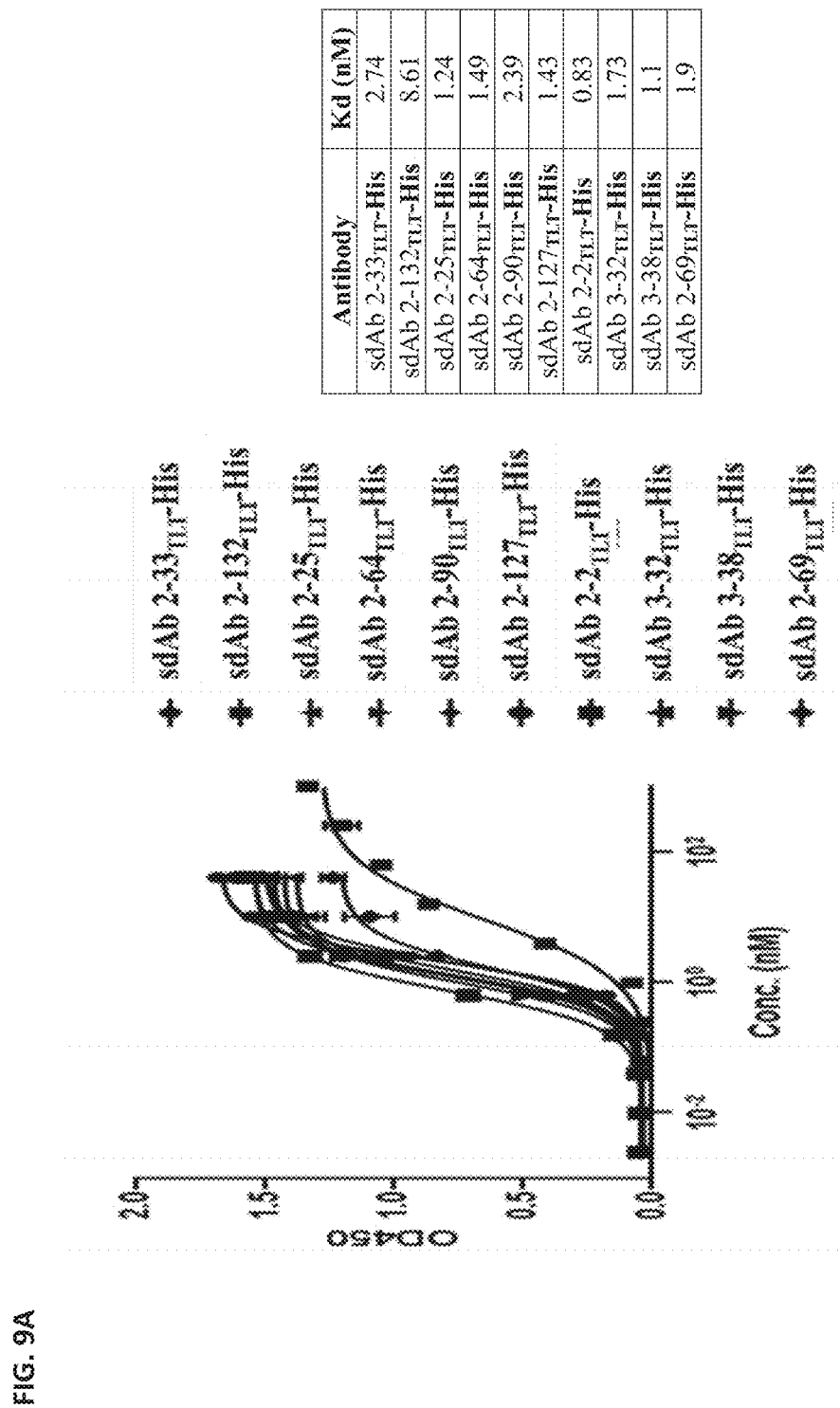
FIGS. 9A and 9B show binding-affinity determinations of proteins to the extracellular domain of human TLT-1. The extracellular domain of human TLT-1 protein was coated onto a 96-well plate for ELISA. After 24 hours incubation at 4° C. and 2 hours of blocking at room temperature (RT) with the blocking buffer, increasing concentrations of ten anti-TLT-1 sdAbs, sTF$_{209}$-PC1sdAb 2-33$_{TLT}$-His and sTF$_{209}$-PC2sdAb 2-90$_{TLT}$-His proteins were added to the respective wells for 1-hour incubation at RT. Anti-His tag—HRP-labeled antibody was used to evaluate the binding. The binding affinity of all ten anti-TLT-1 sdAbs (FIG. 9A) and sTF$_{209}$-PC1-sdAb 2-33$_{TLT}$-His and sTF$_{209}$-PC1sdAb 2-90$_{TLT}$-His (FIG. 9B) are <10 nM. By this criterion, sTF$_{209}$-His does not appear to affect the ability of sdAb$_{TLT}$ to bind to TLT-1.
Figure 9B:
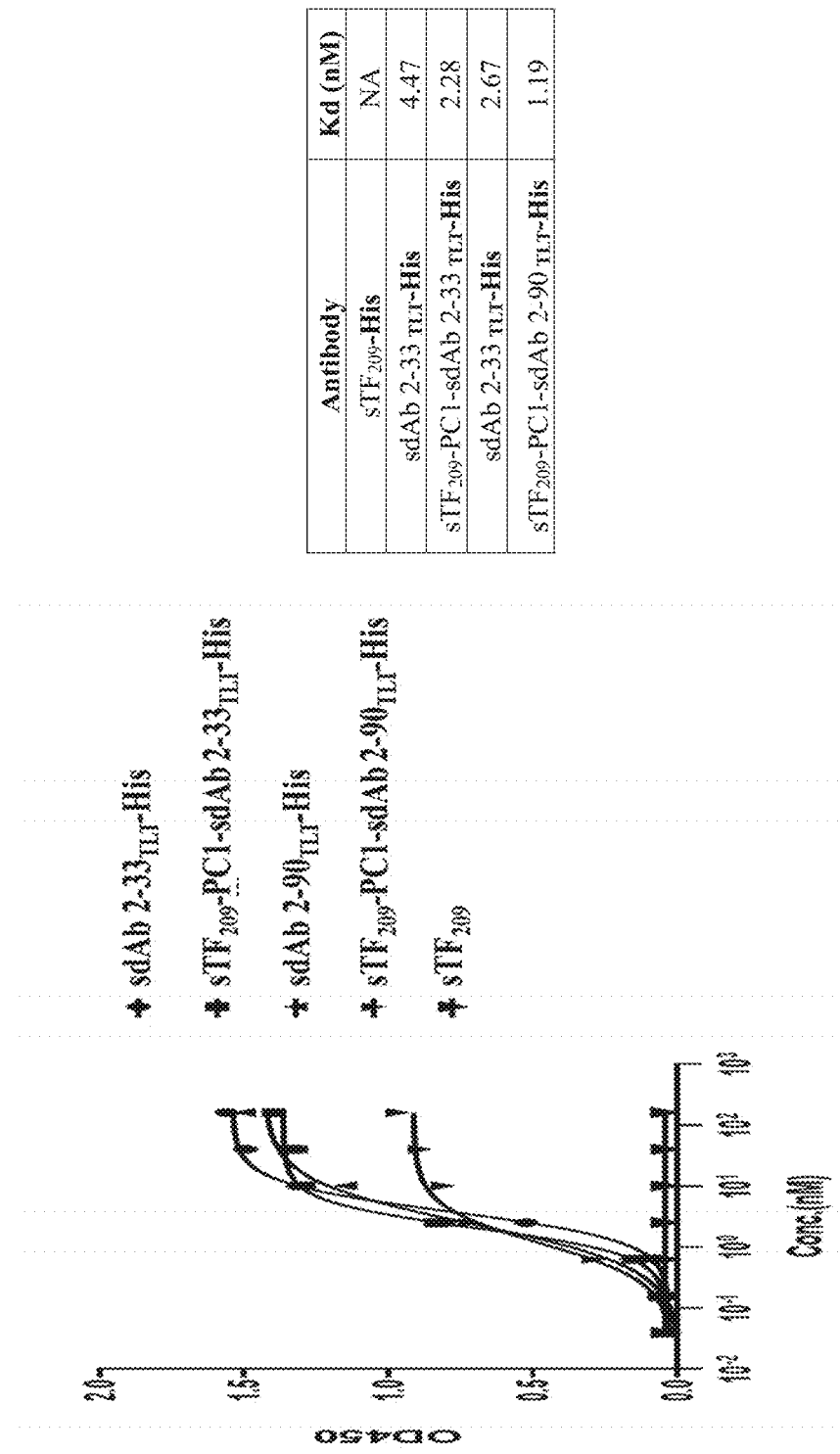

Example 7. Binding Affinity (Kd) Determination of TLT-1 sdAbs and sTF$_{209}$-sdAb Fusion Proteins to Extracellular Domain of TLT-1 Receptor The binding of sdAb 2-33TLT-His, sdAb 2-132 TLT-His, sdAb 2-25 TLT-His, sdAb 2-64 TLT-His, sdAb 2-90 TLT-His, sdAb 2-127 TLT-His, sdAb 2-2 TLT-His, sdAb 3-32 TLT-His, sdAb 3-38 TLT-His and sdAb 2-69 TLT-His, sTF209-PC1-sdAb 2-33TLT-His and sTF209-PC1-sdAb 2-90TLT-His proteins to the human extracellular domain of TLT-1-Fc tagged protein (sTLT-1-Fc) was analyzed using ELISA. STLT-1-Fc (3 µg/ml) was immobilized onto a 96-well plate for 24 hours at 4° C. and each well immobilized with sTLT-1-Fc was blocked with 2% BSA PBST (PBS plus 0.1% Tween 20) for 2 hours at room temperature (RT). Serial dilution (1000 nM to 0.001 nM) of TLT-sdAbs and sTF-sdAb fusion proteins was performed and diluted proteins were then added to the coated 96-well platelet and incubated for 1 hour. After 3 times of washing with PBST, anti-His HRP antibody was added and incubated for 1 hour at RT. The plate was then washed for 3 times to remove the excess HRP conjugate and 100 µL TMB substrate was then added and incubated for 10-15 mins. To stop the reaction of color development, 2M sulfuric acid was added to the well. The binding affinity (Kd) was calculated based on OD450 nm measurement using GRAPHPAD PRISM® 8.0, computer software for analyzing and graph scientific data (FIGS. 9A and 9B). The data indicate that the Kd of sdAb 2-33TLT-His, sdAb 2-90TLT-His, sTF209-PC1-sdAb 2-33TLT-His and sTF209-PC1-sdAb 2-90TLT-His proteins are all in the low nanomolar range (<10 nM).

Example 8. Binding to Activated Human and Mouse Platelets

Figure 10A:
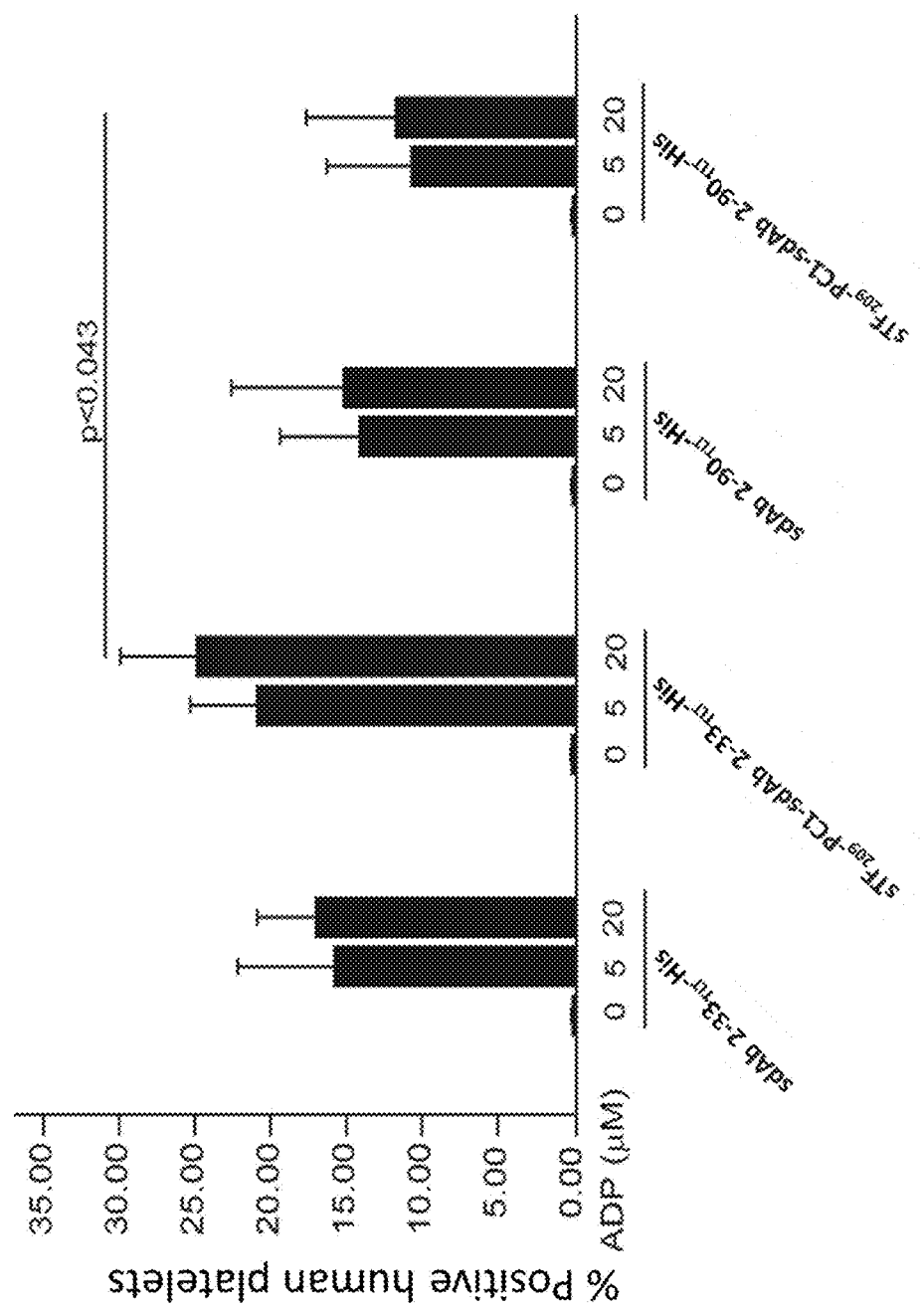
FIGS. 10A and 10B show the binding of proteins to activated platelets. Human and mouse whole blood were used to characterize whether sdAb-2-33$_{TLT}$-His, sdAb 2-90$_{TLT}$-His, sTF$_{209}$-sdAb 2-33$_{TLT}$-His and sTF$_{209}$-PC1-sdAb 2-90$_{TLT}$-His would exclusively bind to both activated human (FIG. 10A) and mouse platelets (FIG. 10B). To prepare activated human platelets, ADP (5 and 20 µM) were preincubated with human whole blood and the above proteins were then added to the ADP-treated whole blood. To prepare activated mouse platelets, collagen, at either 5 µg/ml or 10 µg/ml, was preincubated with mouse whole blood and the above proteins were then added to the ADP-treated whole blood. The binding of the proteins with platelets was detected with FITC-labeled—anti-His tag antibody. The results clearly demonstrated that the sdAb-2-33$_{TLT}$-His, sdAb 2-90$_{TLT}$-His, sTF$_{209}$-PC1-sdAb 2-33$_{TLT}$-His and sTF$_{209}$-PC1-sdAb 2-90$_{TLT}$-His proteins bind to activated both human and mouse platelet exclusively and fused sTF to sdAbs do not alter their binding to platelet TLT-1 receptors. The results provide a basis for using a mouse bleeding model to demonstrate the efficacy of human sTF$_{209}$-PC1-sdAb 2-33$_{TLT}$-His and sTF$_{209}$-PC1-sdAb 2-90$_{TLT}$-His fusion proteins to stem blood loss.
Figure 10B:
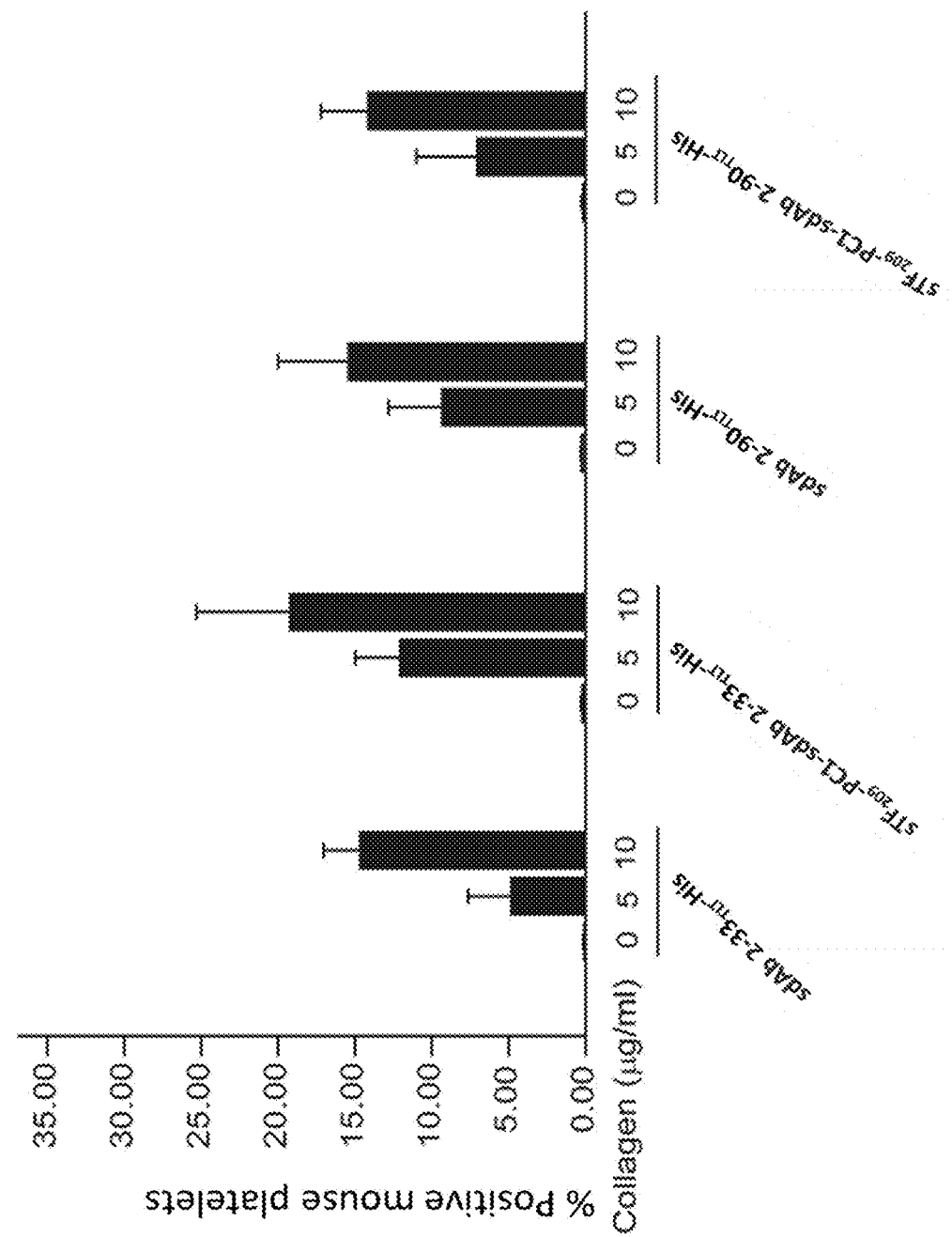

The binding capability of sdAb 2-33$_{TLT}$-His, sTF$_{209}$-PC1-sdAb 2-33$_{TLT}$-His and sTF$_{209}$-PC1-sdAb 2-90$_{TLT}$-His proteins to both human and mouse resting and activated platelets was tested by FACS assay. Citrated human (3 donors) and mouse (12 mice) whole blood were collected at room temperature (RT) and 10 µL of whole blood was used for each sample. To activate human platelets, ADP (5 and 20 µM) was used, and incubated with whole blood for 10 min at room temperature (RT). To activate mouse platelet, Type I fibrillary collagen (5 and 10 ug/ml) was used and incubated with whole blood for 10 min at room temperature (RT). Both ADP and collagen used were from Helena Laboratory, Beaumont Tex., Then, for each sample, 10 µg/ml of test article (i.e., sdAb 2-33$_{TLT}$-His, sdAb 2-90$_{TLT}$-His, sTF$_{209}$-PC1-sdAb 2-33$_{TLT}$-His or sTF$_{209}$-PC1-sdAb 2-90$_{TLT}$-His proteins) was added, followed by one or the other labeled antibodies, either APC-anti-CD41a antibody that was used in gating platelet population, or FITC anti-His antibody, that was used in detecting TLT-1 binding of TLT-sdAbs or sTF$_{209}$-sdAb fusion proteins on activated platelets. APC-anti-CD62P antibody was used as an activated platelet binding control antibody in the assay. After incubation for 30 min at room temperature, all samples were fixed with 500 µL of 5% paraformaldehyde for 10 min at RT and analyzed by FACS (LSR II, Beckon Dickinson, San Jose, CA). Data in FIG. 10A are presented as % of positive platelets collected during a fixed time and demonstrated that sdAb 2-33$_{TLT}$-His, sdAb 2-90$_{TLT}$-His, sTF$_{209}$-PC1-sdAb 2-33$_{TLT}$-His and sTF$_{209}$-PC1-sdAb 2-90$_{TLT}$-His proteins exclusively bind to activated human platelets. FIG. 10B shows the equivalent experiment using mouse platelets. No significant binding difference between sdAbs and sTF-sdAb was observed. These observations demonstrate the novelty of these sdAbs in their ability to bind both mouse and human TLT-1 on activated platelets. This observation further indicates that testing of sdAbs and their fusion counterparts can proceed directly in mouse bleeding models without resorting to the use of transfused human platelets to facilitate binding (Example 13).

Figure 11:
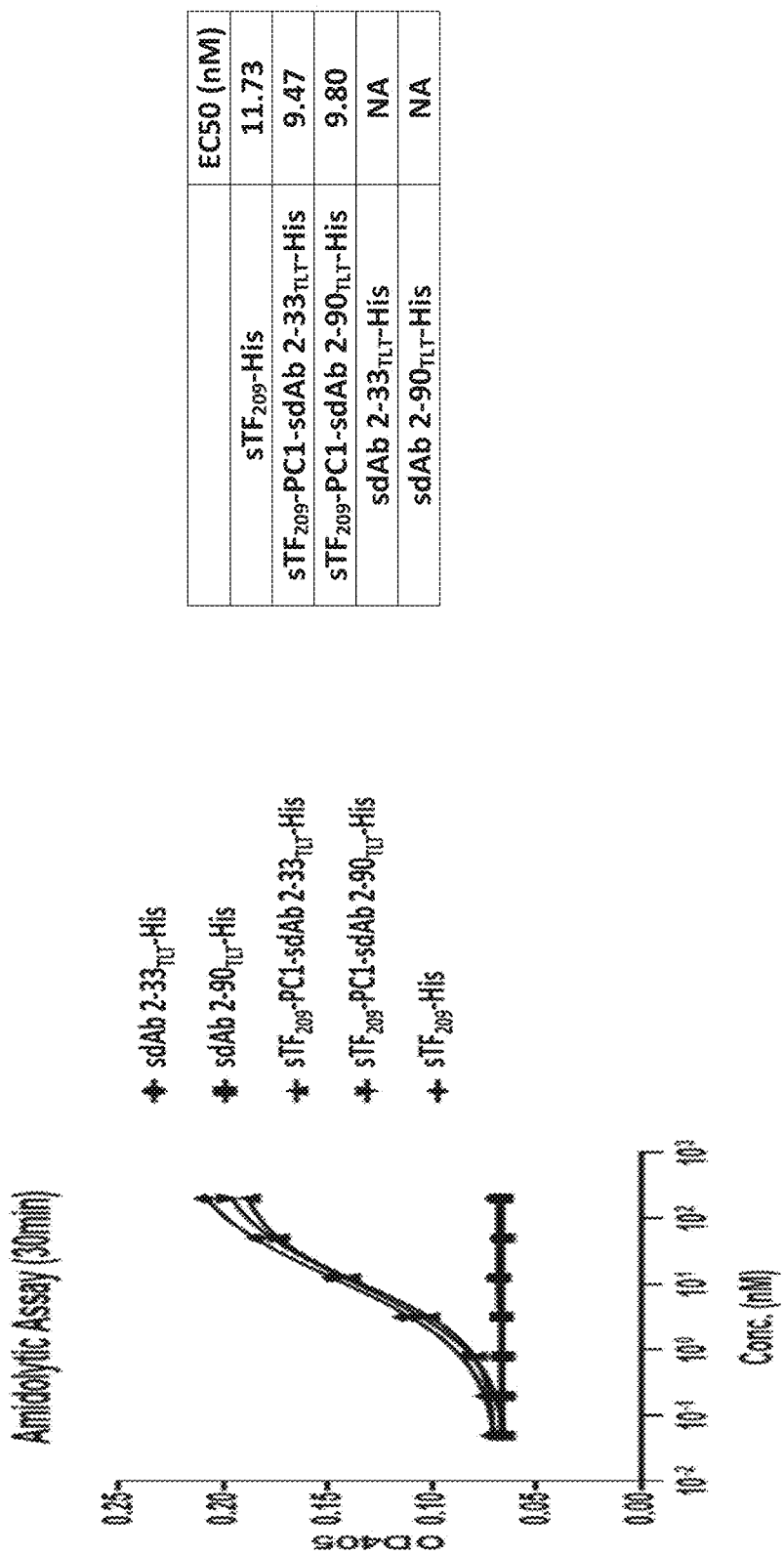
FIG. 11 shows a characterization of FVIIa amidolytic activity. sTF$_{209}$-PC1-dAb 2-33$_{TLT}$-His, sTF$_{209}$-PC1-sdAb 2-90$_{TLT}$-His; sTF$_{209}$-His, sdAb-2-33$_{TLT}$-His and sdAb 2-90$_{TLT}$-His proteins were used as test articles in the assay. The binding curve indicates a similar TF-mediated, concentration-dependent FVIIa amidolytic activity as is seen with both sTF$_{209}$-PC1-dAb 2-33$_{TLT}$-His and sTF$_{209}$-PC1-sdAb 2-90$_{TLT}$-His. This demonstrates that the function of sTF$_{209}$-His was not affected by fusing it to the nanobodies; by contrast, sdAb-2-33$_{TLT}$-His and sdAb 2-90$_{TLT}$-His alone had no effect on FVIIa amidolytic activity.

Example 9. Binding of sTF-sdAb Fusion Proteins to FVIIa sTF$_{209}$-PC1-sdAb 2-33$_{TLT}$-His and sTF$_{209}$-PC1-sdAb 2-90$_{TLT}$-His fusion proteins are designed to target sTF to the surface of activated platelets through sdAb/TLT-1 receptor interaction. To verify whether fusing TLT-1 sdAb to sTF would affect its binding to FVIIa, are FVIIa amidolytic activity assay was performed. Various concentrations (0-100 nM) of sTF$_{209}$ and sTF$_{209}$-sdAb fusion proteins were incubated with factor FVIIa (5 nM) in a butler containing 100 nM NaCl, 50 mM HEPES, pH 7.4, 5 mM CaCl$_2$, 0.1% BSA at 37° C. for 5 minutes. FVIIa amidolytic activity was assayed with the addition of a 5 mM Chromozym tPA substrate and the absorbance were measured at 405 nm at room temperature. Both sdAb 2-33$_{TLT}$-His and sdAb 2-90$_{TLT}$-His were included in the assay as negative controls. The data (FIG. 11) demonstrated that the FVIIa amidolytic activities induced by sTF$_{209}$-PC1-sdAb 2-33$_{TLT}$-His and sTF$_{209}$-PC1-sdAb 2-90$_{TLT}$-His fusion proteins are indistinguishable from that induced by sTF$_{209}$-His in a concentration-dependent manner. These results are consistent with and support observations made for alternate constructs based on sTF and sTF-annexin V (Huang et al., 2006, Blood, volume 107, pp. 980-986).

Figure 12:
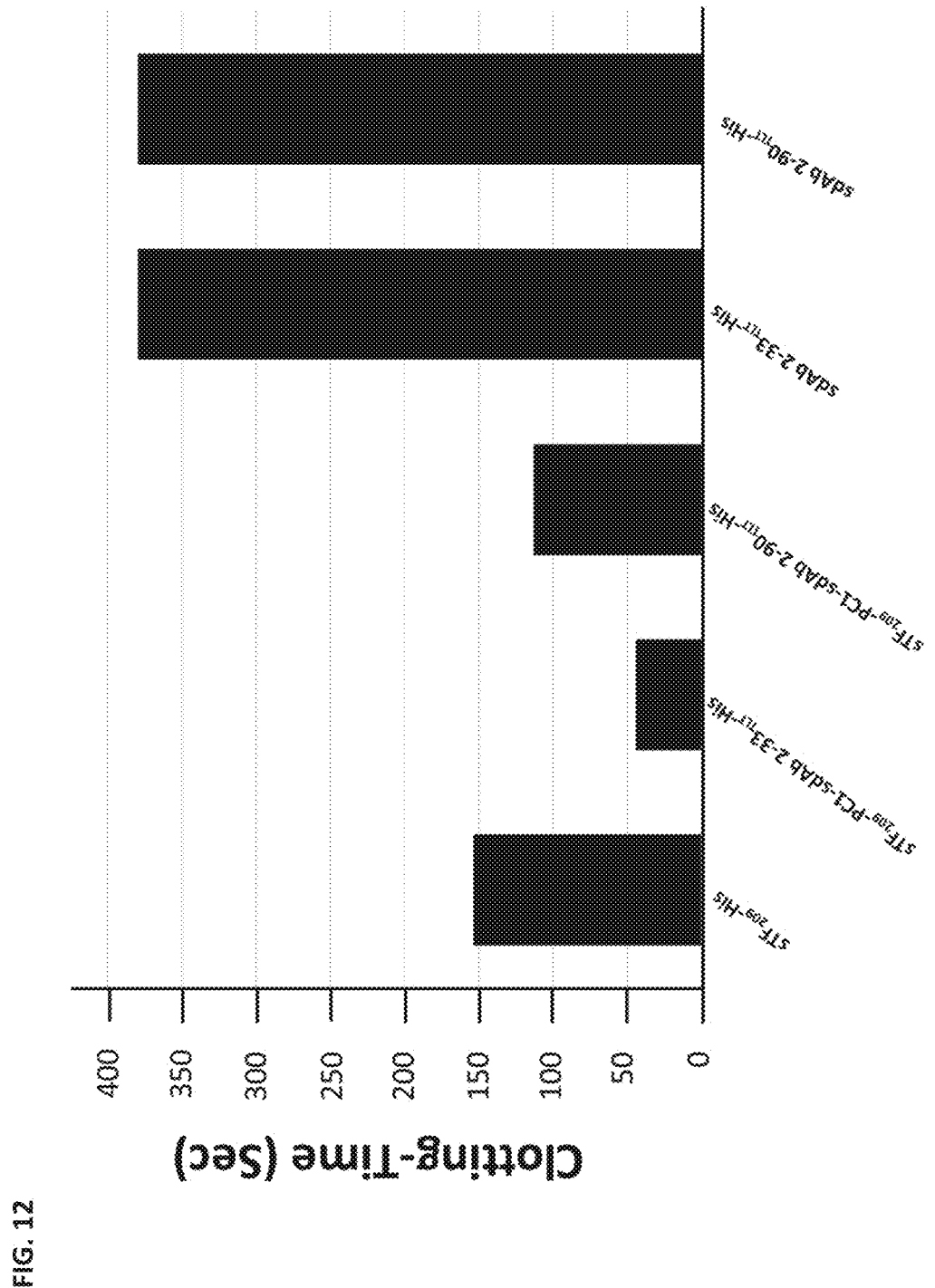
FIG. 12 shows the effect of sTF$_{209}$-PC1-sdAb 2-33$_{TLT}$-His and sTF$_{209}$-PC1-sdAb 2-90$_{TLT}$-His, sTF$_{209}$-His, sdAb-2-33$_{TLT}$-His and sdAb 2-90$_{TLT}$-His in an APTT-like clotting assay. Human FVIII-deficient plasma from a hemophilia A patient was mixed with transfected CHO cells that stably expressed human TLT-1 receptor on the surface, and each of the five proteins at a final concentration of 1 nM were tested in the assay. The result clearly demonstrated the procoagulant activity of both sdAb-2-33$_{TL}$-His and sdAb 2-90$_{TLT}$-His fusion proteins in hemophilia A patient plasma, as there was a dramatic decrease in clotting time observed only with the two fusion proteins.

Example 10. Procoagulant Effect of Targeted sTF$_{209}$ in a One-Stage Clotting Assay Targeting sTF$_{209}$ to TLT-1 receptor is expected to promote coagulant activity. To confirm the hypothesis, the procoagulant activity of sTF$_{209}$-PC1-sdAb 2-33$_{TLT}$ and sTF$_{209}$-PC1-sdAb 2-90$_{TLT}$ fusion proteins were evaluated in a modified one-stage activated partial thromboplastin time (APTT) clot assay. The APTT clotting times were measured using a STar 4 Hemostasis Analyzer (Diagnostica Stago). Fifty microliters of hemophilia A patient plasma (George King Bio-Medical, Overland Park, KS), 50 μL containing 0.5×10$^6$ CHO-K1 cells expressing human TLT-1 protein and 1 nM of test article (sTF$_{209}$-PC1-sdAb 2-33$_{TLT}$-His or sTF$_{209}$-PC1-sdAb 2-90$_{TLT}$-His) were added to the sample cuvette with total volume of 100 μL. After 200 seconds incubation at 37° C., 50 μL calcium chloride (20 mM) was added to initiate the clot formation. The data (FIG. 12) shows that the clotting time of hemophilia A patient plasma with 1 nM sTF$_{209}$-PC1-sdAb 2-33$_{TLT}$-His fusion protein could be completely normalized compared to sTF$_{209}$, sdAb 2-33$_{TLT}$-His and sdAb-2-90$_{TLT}$-His. sTF209-PC1-sdAb 2-90$_{TLT}$-His fusion protein also markedly reduced the clotting time, but potency is less than sTF299-sdAb 2-33$_{TLT}$-His in this type of assay.

Figure 13:
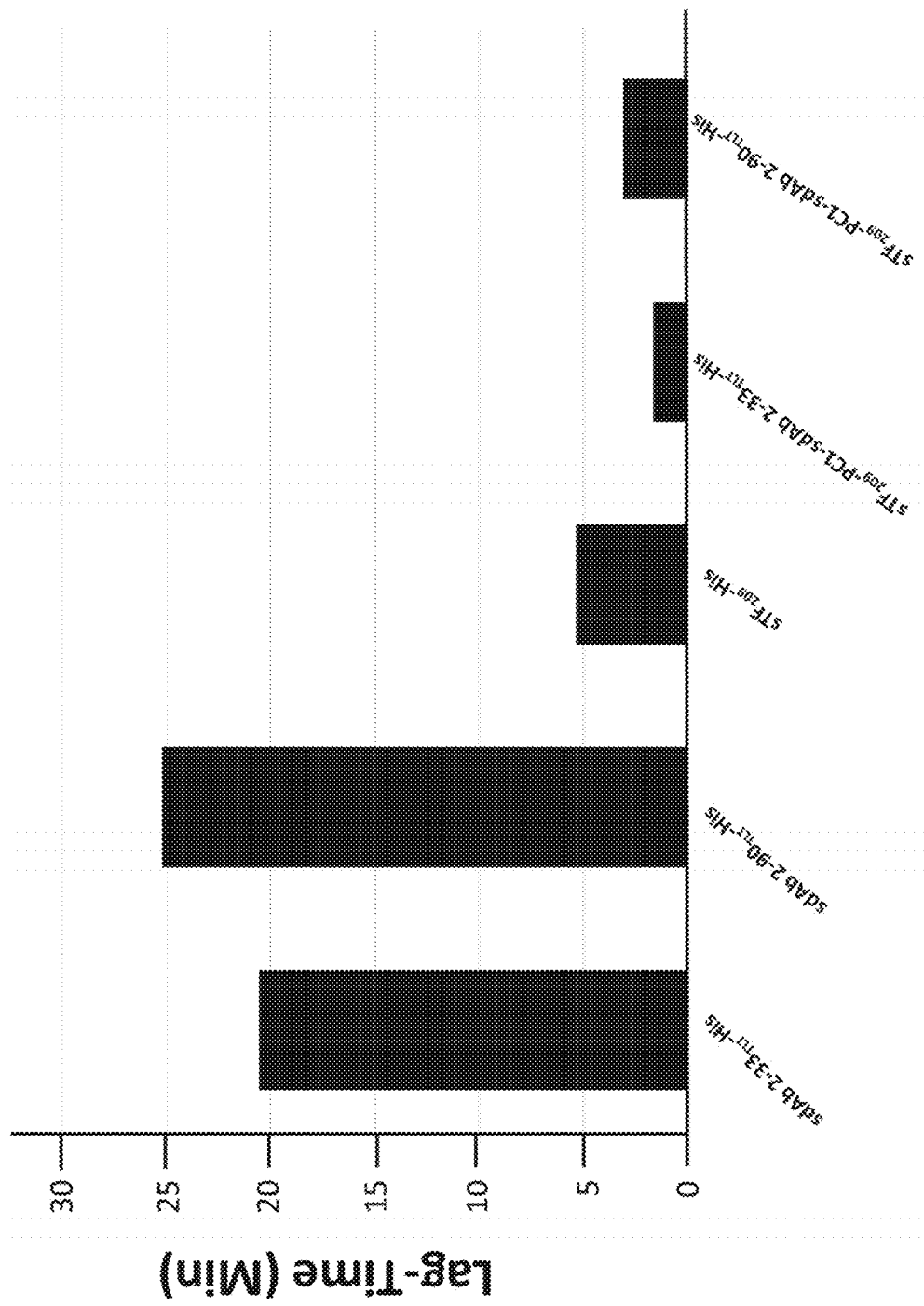
FIG. 13 illustrates thrombin generation promoted by the fusion proteins. A thrombin generation assay (TGA) was used to demonstrate the effects of sTF$_{209}$-PC1-dAb 2-33$_{TLT}$-His and sTF$_{209}$-PC1-sdAb 2-90$_{TLT}$-His, sTF$_{209}$-His, sdAb-2-33$_{TLT}$-His and sdAb 2-90$_{TLT}$-His proteins on thrombin generation. Citrated human platelet-rich plasma (PRP) was mixed with the above five proteins, each present at a final concentration of 25 nM. The TGA results demonstrated that the sTF-sdAb fusions, but not the single-chain antibodies (sdAbs), targeted to platelets markedly reduced the lag-time for peak thrombin generation.

Example 11. Targeted sTF to the Surface of Activated Platelets Promotes Thrombin Generation Human platelet-rich plasma (PRP) was prepared by centrifugation of human whole blood containing 0.32% Sodium Citrate at 150×g for 20 min. Thrombin generation assay was performed by adding 20 μL of PRP reagent (Diagnostica Stago), 80 μL of PRP and 25 nM of testing samples. The reaction was started by the addition of 20 μL FluCa substrate (Diagnostica Stago) to U-bottom 96-well plates (ThermoFisher) and the fluorescent signal from the substrate was detected in a Fluoroskan Ascent plate reader (ThermoFisher). The results showed that STF$_{209}$-PC1-sdAb 2-33$_{TLT}$-His and sTF$_{209}$-PC1-sdAb 2-90$_{TLT}$-His have an increased potency in thrombin generation compared to s TF$_{209}$-His, sdAb 2-33$_{TLT}$-His and sdAb 2-90$_{TLT}$-His (FIG. 13). The lag time of thrombin generation for sTF$_{209}$-PC1-sdAb 2-33$_{TLT}$-His and sTF$_{209}$-PC1-sdAb 2-90$_{TLT}$-His was approximately 2-3 times shorter than sTF$_{209}$-His. These results support the hypothesis that interaction of the selected sdAbs, only when directly fused with sTF as described, promotes binding to TLT-1 and conformational-positioning of sTF with endogenous FVII, its activation to FVIIa, and subsequent thrombin formation.

Figure 14A:
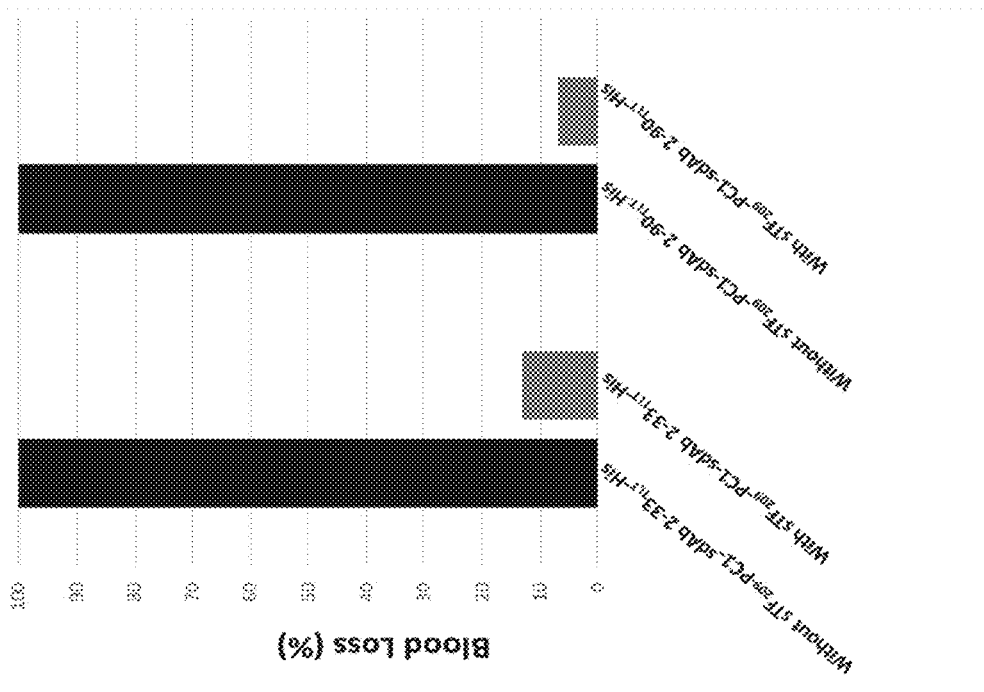
FIGS. 14A-14B demonstrates that the procoagulant effect of fusion proteins in a mouse bleeding model. The mouse bleeding model was established by injecting sodium enoxaparin (30 mg/kg) subcutaneously. Test articles administered in the presence of enoxaparin, namely, STF209-PC1-dAb 2-33 TLT-His, sTF209-PC1-sdAb 2-90 TLT-His, and controls, were administered at a dose of 90 g/kg of mouse body weight. Blood loss was measured by weighing blood collected during the tail bleeding assay. Time to clot formation was determined by directed visualization when bleeding stopped.
Figure 14B:
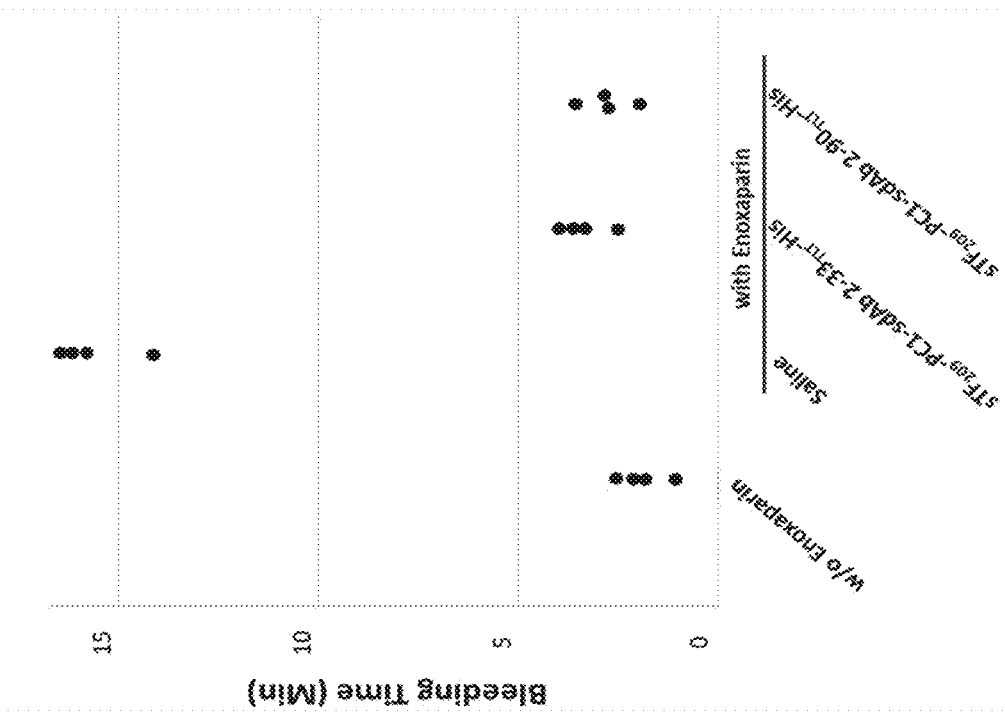

Example 12. sTF209-sdAb Fusion Proteins Reduced Tail-Bleeding in Enoxaparin Treated Mice The procoagulant effect of sTF$_{209}$-PC1-sdAb 2-33$_{TLT}$-His and sTF$_{209}$-PC1-sdAb 2-90$_{FLT}$-His fusion proteins were tested in an enoxaparin-induced tail-bleeding model in mice (Washington Biotechnology Inc, Baltimore Md.). Mice (4 per group) were injected subcutaneously with sodium enoxaparin (30 mg/kg) and two hours later were anaesthetized by intraperitoneal injection of ketamine/xylazine (10 mg/kg). The baseline bleeding time and blood loss were determined by transecting the mouse tail at a point 10 mm from tail tip. The time required for bleeding to stop was recorded, and blood loss was determined by collecting blood in a warmed (37° C.) normal saline solution. An intravenous injection of sTF$_{209}$-PC1-sdAb 2-33$_{TLT}$-His and sTF$_{209}$-PC1-sdAb 2-90$_{FLT}$-His fusion proteins (90 μg/kg) were performed immediately after the first bleeding time determination. A second bleeding time was then measured 5 minutes after the injection of the above proteins, and bleeding time and blood loss was determined in a similar manner as described. The results show that administration of the sTF$_{209}$-PC1-sdAb 2-33$_{TLT}$-His and sTF$_{209}$-PC1-sdAb 2-90$_{TLT}$-His fusion proteins completely normalize the bleeding time to that of control animals in this bleeding model (FIG. 14A) and significantly reduced blood loss (FIG. 14B).

Example 13. Targeted sTF to the Surface of Activated Platelets Promotes Fibrin Clot Formation in Human Whole Blood (Prophetic Example)

Citrated human whole blood (HWB) is drawn from normal donors. Clot formation is measured by thrombelastography (TEG5000) analyzer (Haemonetics, Boston, MA). The final concentrations (0-100 nM) of sdAb 2-33$_{TLT}$-His, sdAb 2-90$_{TLT}$-His, sTF$_{209}$-His, sTF$_{209}$-PC1-sdAb 2-33$_{TLT}$-His and sTF$_{209}$-PC1-sdAb 2-90$_{TLT}$-His are added to 340 μL of whole blood containing the kaolin activator. Clotting formation measurement is initiated with addition of 20 μL of 0.2 M CaCl$_2$. The TEG trace is followed continuously for up to 60 min. The R-time (clotting time) is recorded for potency comparison of testing samples. The data are expected to demonstrate that sTF$_{209}$-sdAb fusion proteins shortened R-time (clotting time) in a concentration dependent manner compared to sTF$_{209}$-His and sdAb 2-33$_{TLT}$-His and sdAb 2-90$_{TLT}$-His proteins. The results are expected to further demonstrate that the enhanced thrombin generation seen in Example 11 generates bona fide fibrin formation necessary to generate a functional clot.

What is claimed is:

1. A single domain antibody against triggering receptors expressed on myeloid cells (TREM)-like transcript-1 (TLT-1), comprising:
   (a) CDR1 being SEQ ID NO: 6, CDR2 being SEQ ID NO: 32, CDR3 being SEQ ID NO: 43;
   (b) CDR1 being SEQ ID NO: 8, CDR2 being SEQ ID NO: 31, CDR3 being SEQ ID NO: 44;
   (c) CDR1 being SEQ ID NO: 3, CDR2 being SEQ ID NO: 31, CDR3 being SEQ ID NO: 41;
   (d) CDR1 being SEQ ID NO: 3, CDR2 being SEQ ID NO: 31, CDR3 being SEQ ID NO: 42;
   (e) CDR1 being SEQ ID NO: 1, CDR2 being SEQ ID NO: 31, CDR3 being SEQ ID NO: 40;
   (f) CDR1 being SEQ ID NO: 25, CDR2 being SEQ ID NO: 35, CDR3 being SEQ ID NO: 45;
   (g) CDR1 being SEQ ID NO: 3, CDR2 being SEQ ID NO: 31, CDR3 being SEQ ID NO: 46;
   (h) CDR1 being SEQ ID NO: 11, CDR2 being SEQ ID NO: 31, CDR3 being SEQ ID NO: 47;
   (i) CDR1 being SEQ ID NO: 16, CDR2 being SEQ ID NO: 31, CDR3 being SEQ ID NO: 50; or
   (j) CDR1 being SEQ ID NO: 25, CDR2 being SEQ ID NO: 35, CDR3 being SEQ ID NO: 59.

2. The single domain antibody according to claim 1, comprising the sequence selected from the group consisting of SEQ ID NOs: 68, 70, 64, 65, 62, 71, 74, 76, 80, and 95, or a sequence having at least 95% identity thereof, provided that the sequence variation is in the non-CDR framework region.

3. A fusion protein comprising (i) an extracellular domain of a tissue factor protein having the amino acid sequence of 1-208, 1-209, 1-210, 1-211, 1-212, 1-213, 1-214, 1-215, 1-216, 1-217, 1-218, 1-219, 1-220, or 1-221 amino acid residues of SEQ ID NO: 110, (ii) a single domain antibody according claim 1, and (iii) a linker.

4. The fusion protein according to claim 3, wherein the linker has a length of 15-30 amino acids.

5. The fusion protein according to claim 3, further comprises a protease cleavage site.

6. The fusion protein according to claim 5, wherein the protease cleavage site is a thrombin cleavage site or a FXa cleavage site.

7. A pharmaceutical composition comprising the fusion protein of claim 3 and a pharmaceutically acceptable carrier.

8. A single domain antibody comprising the sequence selected from the group consisting of SEQ ID NOs: 62-99, or a sequence having 95% identity thereof, provided that the sequence variation is in a non-CDR framework region.

9. A fusion protein comprising the amino acid sequence of SEQ ID NO: 106, 107, 108, 109, 111, or 112.

10. A pharmaceutical composition comprising the fusion protein of claim 9 and a pharmaceutically acceptable carrier.

\* \* \* \* \*

SEQUENCE LISTING

<160> NUMBER OF SEQ ID NOS: 118

<210> SEQ ID NO 1
<211> LENGTH: 8
<212> TYPE: PRT
<213> ORGANISM: Unknown

```
<220> FEATURE:
<223> OTHER INFORMATION: Camelidae

<400> SEQUENCE: 1

Gly Asn Thr Ser Gly Ile Asn Val
1               5

<210> SEQ ID NO 2
<211> LENGTH: 8
<212> TYPE: PRT
<213> ORGANISM: Unknown
<220> FEATURE:
<223> OTHER INFORMATION: Camelidae

<400> SEQUENCE: 2

Gly Asp Thr Ser Gly Ile Asn Ile
1               5

<210> SEQ ID NO 3
<211> LENGTH: 8
<212> TYPE: PRT
<213> ORGANISM: Unknown
<220> FEATURE:
<223> OTHER INFORMATION: Camelidae

<400> SEQUENCE: 3

Gly Ser Thr Ser Asp Ile Asn Ile
1               5

<210> SEQ ID NO 4
<211> LENGTH: 8
<212> TYPE: PRT
<213> ORGANISM: Unknown
<220> FEATURE:
<223> OTHER INFORMATION: Camelidae

<400> SEQUENCE: 4

Gly Ser Thr Ser Glu Ile Asn Val
1               5

<210> SEQ ID NO 5
<211> LENGTH: 8
<212> TYPE: PRT
<213> ORGANISM: Unknown
<220> FEATURE:
<223> OTHER INFORMATION: Camelidae

<400> SEQUENCE: 5

Gly Ser Thr Ser Glu Ile Asn Ile
1               5

<210> SEQ ID NO 6
<211> LENGTH: 8
<212> TYPE: PRT
<213> ORGANISM: Unknown
<220> FEATURE:
<223> OTHER INFORMATION: Camelidae

<400> SEQUENCE: 6

Gly Ser Ile Ala Asn Ile Gly Gly
1               5

<210> SEQ ID NO 7
<211> LENGTH: 8
<212> TYPE: PRT
<213> ORGANISM: Unknown
<220> FEATURE:
```

```
<223> OTHER INFORMATION: Camelidae

<400> SEQUENCE: 7

Gly Ser Ile Ala Asn Ile Asn Gly
1               5

<210> SEQ ID NO 8
<211> LENGTH: 8
<212> TYPE: PRT
<213> ORGANISM: Unknown
<220> FEATURE:
<223> OTHER INFORMATION: Camelidae

<400> SEQUENCE: 8

Gly Ser Thr Ser Gly Ile Asn Val
1               5

<210> SEQ ID NO 9
<211> LENGTH: 8
<212> TYPE: PRT
<213> ORGANISM: Unknown
<220> FEATURE:
<223> OTHER INFORMATION: Camelidae

<400> SEQUENCE: 9

Gly Asn Thr Ser Gly Ile Asn Ile
1               5

<210> SEQ ID NO 10
<211> LENGTH: 8
<212> TYPE: PRT
<213> ORGANISM: Unknown
<220> FEATURE:
<223> OTHER INFORMATION: Camelidae

<400> SEQUENCE: 10

Gly Ser Thr Ser Gly Ile Asn Ile
1               5

<210> SEQ ID NO 11
<211> LENGTH: 8
<212> TYPE: PRT
<213> ORGANISM: Unknown
<220> FEATURE:
<223> OTHER INFORMATION: Camelidae

<400> SEQUENCE: 11

Gly Ser Thr Ser Asp Ile Asn Leu
1               5

<210> SEQ ID NO 12
<211> LENGTH: 8
<212> TYPE: PRT
<213> ORGANISM: Unknown
<220> FEATURE:
<223> OTHER INFORMATION: Camelidae

<400> SEQUENCE: 12

Gly Ser Thr Pro Asp Ile Asn Leu
1               5

<210> SEQ ID NO 13
<211> LENGTH: 8
<212> TYPE: PRT
<213> ORGANISM: Unknown
<220> FEATURE:
<223> OTHER INFORMATION: Camelidae
```

```
<400> SEQUENCE: 13

Gly Asp Thr Ser Asp Ile Asn Val
1               5

<210> SEQ ID NO 14
<211> LENGTH: 9
<212> TYPE: PRT
<213> ORGANISM: Unknown
<220> FEATURE:
<223> OTHER INFORMATION: Camelidae

<400> SEQUENCE: 14

Gly Gly Ser Thr Ser Asp Ile Asn Ile
1               5

<210> SEQ ID NO 15
<211> LENGTH: 9
<212> TYPE: PRT
<213> ORGANISM: Unknown
<220> FEATURE:
<223> OTHER INFORMATION: Camelidae

<400> SEQUENCE: 15

Gly Arg Ser Thr Ser Asp Ile Asn Ile
1               5

<210> SEQ ID NO 16
<211> LENGTH: 9
<212> TYPE: PRT
<213> ORGANISM: Unknown
<220> FEATURE:
<223> OTHER INFORMATION: Camelidae

<400> SEQUENCE: 16

Ser Gly Asn Thr Ser Gly Ile Asn Val
1               5

<210> SEQ ID NO 17
<211> LENGTH: 9
<212> TYPE: PRT
<213> ORGANISM: Unknown
<220> FEATURE:
<223> OTHER INFORMATION: Camelidae

<400> SEQUENCE: 17

Ser Gly Asn Thr Ser Gly Ile Asn Ile
1               5

<210> SEQ ID NO 18
<211> LENGTH: 8
<212> TYPE: PRT
<213> ORGANISM: Unknown
<220> FEATURE:
<223> OTHER INFORMATION: Camelidae

<400> SEQUENCE: 18

Gly Ser Ile Ser Ser Ile Asn Val
1               5

<210> SEQ ID NO 19
<211> LENGTH: 8
<212> TYPE: PRT
<213> ORGANISM: Unknown
<220> FEATURE:
<223> OTHER INFORMATION: Camelidae
```

```
<400> SEQUENCE: 19

Arg Asp Ile Phe Ser Phe Asn Val
1               5

<210> SEQ ID NO 20
<211> LENGTH: 8
<212> TYPE: PRT
<213> ORGANISM: Unknown
<220> FEATURE:
<223> OTHER INFORMATION: Camelidae

<400> SEQUENCE: 20

Gly Ser Thr Ser Ser Ile Asn Ile
1               5

<210> SEQ ID NO 21
<211> LENGTH: 8
<212> TYPE: PRT
<213> ORGANISM: Unknown
<220> FEATURE:
<223> OTHER INFORMATION: Camelidae

<400> SEQUENCE: 21

Gly Ser Thr Ser Asn Ile Asn Ile
1               5

<210> SEQ ID NO 22
<211> LENGTH: 8
<212> TYPE: PRT
<213> ORGANISM: Unknown
<220> FEATURE:
<223> OTHER INFORMATION: Camelidae

<400> SEQUENCE: 22

Gly Ser Thr Ser Gly Ile Asn Leu
1               5

<210> SEQ ID NO 23
<211> LENGTH: 9
<212> TYPE: PRT
<213> ORGANISM: Unknown
<220> FEATURE:
<223> OTHER INFORMATION: Camelidae

<400> SEQUENCE: 23

Thr Ser Gly Phe Ser Phe Ser Asp Tyr
1               5

<210> SEQ ID NO 24
<211> LENGTH: 8
<212> TYPE: PRT
<213> ORGANISM: Unknown
<220> FEATURE:
<223> OTHER INFORMATION: Camelidae

<400> SEQUENCE: 24

Gly Ile Ser Phe Ser Asp Ala Ala
1               5

<210> SEQ ID NO 25
<211> LENGTH: 8
<212> TYPE: PRT
<213> ORGANISM: Unknown
<220> FEATURE:
<223> OTHER INFORMATION: Camelidae

<400> SEQUENCE: 25
```

```
Gly Asn Thr Ser Gly Ile Asn Leu
1               5
```

<210> SEQ ID NO 26
<211> LENGTH: 8
<212> TYPE: PRT
<213> ORGANISM: Unknown
<220> FEATURE:
<223> OTHER INFORMATION: Camelidae

<400> SEQUENCE: 26

```
Gly Ser Thr Ser Ser Ile Asn Ile
1               5
```

<210> SEQ ID NO 27
<211> LENGTH: 8
<212> TYPE: PRT
<213> ORGANISM: Unknown
<220> FEATURE:
<223> OTHER INFORMATION: Camelidae

<400> SEQUENCE: 27

```
Gly Ser Thr Ser Gly Ile Asn Ile
1               5
```

<210> SEQ ID NO 28
<211> LENGTH: 8
<212> TYPE: PRT
<213> ORGANISM: Unknown
<220> FEATURE:
<223> OTHER INFORMATION: Camelidae

<400> SEQUENCE: 28

```
Gly Asn Thr Ser Gly Ile Asn Ile
1               5
```

<210> SEQ ID NO 29
<211> LENGTH: 8
<212> TYPE: PRT
<213> ORGANISM: Unknown
<220> FEATURE:
<223> OTHER INFORMATION: Camelidae

<400> SEQUENCE: 29

```
Gly Asn Thr Ser Gly Ile Asn Val
1               5
```

<210> SEQ ID NO 30
<211> LENGTH: 8
<212> TYPE: PRT
<213> ORGANISM: Unknown
<220> FEATURE:
<223> OTHER INFORMATION: Camelidae

<400> SEQUENCE: 30

```
Gly Ser Thr Ser Asp Ile Asn Val
1               5
```

<210> SEQ ID NO 31
<211> LENGTH: 7
<212> TYPE: PRT
<213> ORGANISM: Unknown
<220> FEATURE:
<223> OTHER INFORMATION: Camelidae

<400> SEQUENCE: 31

Lys Ala Arg Gly Gly Leu Pro
1               5

<210> SEQ ID NO 32
<211> LENGTH: 8
<212> TYPE: PRT
<213> ORGANISM: Unknown
<220> FEATURE:
<223> OTHER INFORMATION: Camelidae

<400> SEQUENCE: 32

Ile Thr Ser Ala Gly Thr Ala Ser
1               5

<210> SEQ ID NO 33
<211> LENGTH: 7
<212> TYPE: PRT
<213> ORGANISM: Unknown
<220> FEATURE:
<223> OTHER INFORMATION: Camelidae

<400> SEQUENCE: 33

Ile Thr Thr Pro Gly Tyr Thr
1               5

<210> SEQ ID NO 34
<211> LENGTH: 7
<212> TYPE: PRT
<213> ORGANISM: Unknown
<220> FEATURE:
<223> OTHER INFORMATION: Camelidae

<400> SEQUENCE: 34

Ile Thr Ser Ala Gly Tyr Thr
1               5

<210> SEQ ID NO 35
<211> LENGTH: 7
<212> TYPE: PRT
<213> ORGANISM: Unknown
<220> FEATURE:
<223> OTHER INFORMATION: Camelidae

<400> SEQUENCE: 35

Ile Ala Arg Gly Gly Leu Pro
1               5

<210> SEQ ID NO 36
<211> LENGTH: 7
<212> TYPE: PRT
<213> ORGANISM: Unknown
<220> FEATURE:
<223> OTHER INFORMATION: Camelidae

<400> SEQUENCE: 36

Ile Asn Pro Asn Gly Phe Thr
1               5

<210> SEQ ID NO 37
<211> LENGTH: 7
<212> TYPE: PRT
<213> ORGANISM: Unknown
<220> FEATURE:
<223> OTHER INFORMATION: Camelidae

<400> SEQUENCE: 37

Ile Gly Asn Arg Gly Ser Val

<210> SEQ ID NO 38
<211> LENGTH: 7
<212> TYPE: PRT
<213> ORGANISM: Unknown
<220> FEATURE:
<223> OTHER INFORMATION: Camelidae

<400> SEQUENCE: 38

Ile Thr Thr Phe Gly Tyr Ile
1               5

<210> SEQ ID NO 39
<211> LENGTH: 7
<212> TYPE: PRT
<213> ORGANISM: Unknown
<220> FEATURE:
<223> OTHER INFORMATION: Camelidae

<400> SEQUENCE: 39

Met Ala Arg Gly Gly Leu Pro
1               5

<210> SEQ ID NO 40
<211> LENGTH: 11
<212> TYPE: PRT
<213> ORGANISM: Unknown
<220> FEATURE:
<223> OTHER INFORMATION: Camelidae

<400> SEQUENCE: 40

Asn Ala Val Trp Asp Trp Ala Leu Ala Glu Tyr
1               5                   10

<210> SEQ ID NO 41
<211> LENGTH: 11
<212> TYPE: PRT
<213> ORGANISM: Unknown
<220> FEATURE:
<223> OTHER INFORMATION: Camelidae

<400> SEQUENCE: 41

Asn Ala Val Ser Asp Trp Lys Leu Gly Asp Tyr
1               5                   10

<210> SEQ ID NO 42
<211> LENGTH: 11
<212> TYPE: PRT
<213> ORGANISM: Unknown
<220> FEATURE:
<223> OTHER INFORMATION: Camelidae

<400> SEQUENCE: 42

Asn Ala Val Thr Asp Trp Ala Leu Gly Asp Tyr
1               5                   10

<210> SEQ ID NO 43
<211> LENGTH: 10
<212> TYPE: PRT
<213> ORGANISM: Unknown
<220> FEATURE:
<223> OTHER INFORMATION: Camelidae

<400> SEQUENCE: 43

Lys Ala Trp Asp Arg Asp Leu Val Asp Tyr
1               5                   10

```
<210> SEQ ID NO 44
<211> LENGTH: 11
<212> TYPE: PRT
<213> ORGANISM: Unknown
<220> FEATURE:
<223> OTHER INFORMATION: Camelidae

<400> SEQUENCE: 44

Asn Ala Leu Leu Asp Trp Arg Leu Gly Asp Tyr
1               5                   10

<210> SEQ ID NO 45
<211> LENGTH: 11
<212> TYPE: PRT
<213> ORGANISM: Unknown
<220> FEATURE:
<223> OTHER INFORMATION: Camelidae

<400> SEQUENCE: 45

Asn Ala Val Trp Asp Trp Lys Leu Gly Asp Tyr
1               5                   10

<210> SEQ ID NO 46
<211> LENGTH: 11
<212> TYPE: PRT
<213> ORGANISM: Unknown
<220> FEATURE:
<223> OTHER INFORMATION: Camelidae

<400> SEQUENCE: 46

Asn Ala Val Thr Asp Trp Gln Leu Gly Asp Tyr
1               5                   10

<210> SEQ ID NO 47
<211> LENGTH: 11
<212> TYPE: PRT
<213> ORGANISM: Unknown
<220> FEATURE:
<223> OTHER INFORMATION: Camelidae

<400> SEQUENCE: 47

Asn Ala Leu Leu Asp Trp Arg Ala Gly Asp Tyr
1               5                   10

<210> SEQ ID NO 48
<211> LENGTH: 11
<212> TYPE: PRT
<213> ORGANISM: Unknown
<220> FEATURE:
<223> OTHER INFORMATION: Camelidae

<400> SEQUENCE: 48

Asn Ala Leu Leu Asp Trp Ala Leu Gly Glu Tyr
1               5                   10

<210> SEQ ID NO 49
<211> LENGTH: 11
<212> TYPE: PRT
<213> ORGANISM: Unknown
<220> FEATURE:
<223> OTHER INFORMATION: Camelidae

<400> SEQUENCE: 49

Asn Ala Val Leu Asp Trp Lys Leu Gly Glu Tyr
1               5                   10
```

<210> SEQ ID NO 50
<211> LENGTH: 11
<212> TYPE: PRT
<213> ORGANISM: Unknown
<220> FEATURE:
<223> OTHER INFORMATION: Camelidae

<400> SEQUENCE: 50

Asn Ala Val Trp Asp Trp Gln Leu Gly Asp Tyr
1               5                   10

<210> SEQ ID NO 51
<211> LENGTH: 12
<212> TYPE: PRT
<213> ORGANISM: Unknown
<220> FEATURE:
<223> OTHER INFORMATION: Camelidae

<400> SEQUENCE: 51

Ala Ala Ala Glu Ala Tyr Ala Glu Lys Tyr Asp Tyr
1               5                   10

<210> SEQ ID NO 52
<211> LENGTH: 11
<212> TYPE: PRT
<213> ORGANISM: Unknown
<220> FEATURE:
<223> OTHER INFORMATION: Camelidae

<400> SEQUENCE: 52

Asn Ala Val Glu Asp Trp Arg Leu Gly Asp Tyr
1               5                   10

<210> SEQ ID NO 53
<211> LENGTH: 11
<212> TYPE: PRT
<213> ORGANISM: Unknown
<220> FEATURE:
<223> OTHER INFORMATION: Camelidae

<400> SEQUENCE: 53

Asn Ala Val Leu Asp Trp Gln Leu Gly Asp Tyr
1               5                   10

<210> SEQ ID NO 54
<211> LENGTH: 11
<212> TYPE: PRT
<213> ORGANISM: Unknown
<220> FEATURE:
<223> OTHER INFORMATION: Camelidae

<400> SEQUENCE: 54

His Ala Val Arg Ile Ser Gly Gly Ala Asn Tyr
1               5                   10

<210> SEQ ID NO 55
<211> LENGTH: 7
<212> TYPE: PRT
<213> ORGANISM: Unknown
<220> FEATURE:
<223> OTHER INFORMATION: Camelidae

<400> SEQUENCE: 55

Arg Ser Phe Gln Pro Asp Leu
1               5

```
<210> SEQ ID NO 56
<211> LENGTH: 11
<212> TYPE: PRT
<213> ORGANISM: Unknown
<220> FEATURE:
<223> OTHER INFORMATION: Camelidae

<400> SEQUENCE: 56

Asn Ala Leu Trp Asp Trp Arg Leu Gly Glu Tyr
1               5                   10

<210> SEQ ID NO 57
<211> LENGTH: 11
<212> TYPE: PRT
<213> ORGANISM: Unknown
<220> FEATURE:
<223> OTHER INFORMATION: Camelidae

<400> SEQUENCE: 57

His Ala Leu Glu Asp Trp Ala Leu Gly Glu Tyr
1               5                   10

<210> SEQ ID NO 58
<211> LENGTH: 11
<212> TYPE: PRT
<213> ORGANISM: Unknown
<220> FEATURE:
<223> OTHER INFORMATION: Camelidae

<400> SEQUENCE: 58

Asn Ala Leu Trp Asp Trp Ala Leu Gly Glu Tyr
1               5                   10

<210> SEQ ID NO 59
<211> LENGTH: 11
<212> TYPE: PRT
<213> ORGANISM: Unknown
<220> FEATURE:
<223> OTHER INFORMATION: Camelidae

<400> SEQUENCE: 59

Asn Ala Val Trp Asp Trp Arg Leu Gly Glu Tyr
1               5                   10

<210> SEQ ID NO 60
<211> LENGTH: 11
<212> TYPE: PRT
<213> ORGANISM: Unknown
<220> FEATURE:
<223> OTHER INFORMATION: Camelidae

<400> SEQUENCE: 60

Asn Ala Val Leu Asp Trp Arg Leu Gly Asp Tyr
1               5                   10

<210> SEQ ID NO 61
<211> LENGTH: 11
<212> TYPE: PRT
<213> ORGANISM: Unknown
<220> FEATURE:
<223> OTHER INFORMATION: Camelidae

<400> SEQUENCE: 61

Asn Ala Leu Leu Asp Trp Arg Leu Gly Glu Tyr
1               5                   10

<210> SEQ ID NO 62
```

```
<211> LENGTH: 117
<212> TYPE: PRT
<213> ORGANISM: Unknown
<220> FEATURE:
<223> OTHER INFORMATION: Camelidae

<400> SEQUENCE: 62

Gln Val Gln Leu Val Glu Ser Gly Gly Gly Leu Val Gln Ala Gly Gly
1               5                   10                  15

Ser Leu Arg Leu Ser Cys Ala Ala Ser Gly Asn Thr Ser Gly Ile Asn
            20                  25                  30

Val Met Ala Trp Tyr Arg Gln Ala Ser Gly Lys Gln Arg Glu Leu Val
        35                  40                  45

Ala Asn Lys Ala Arg Gly Gly Leu Pro Lys Tyr Gly Asn Ser Ala Lys
    50                  55                  60

Gly Arg Phe Thr Ile Ser Arg Asp Asn Ala Lys Asn Thr Ile Tyr Leu
65                  70                  75                  80

Gln Met Asn Asn Leu Lys Pro Glu Asp Thr Ala Val Tyr Tyr Cys Asn
                85                  90                  95

Ala Val Trp Asp Trp Ala Leu Ala Glu Tyr Trp Gly Gln Gly Thr Gln
            100                 105                 110

Val Thr Val Ser Ser
            115

<210> SEQ ID NO 63
<211> LENGTH: 117
<212> TYPE: PRT
<213> ORGANISM: Unknown
<220> FEATURE:
<223> OTHER INFORMATION: Camelidae

<400> SEQUENCE: 63

Gln Val Gln Leu Val Glu Ser Gly Gly Gly Leu Val Gln Ala Gly Gly
1               5                   10                  15

Ser Leu Arg Leu Ser Cys Ala Ala Ser Gly Asp Thr Ser Gly Ile Asn
            20                  25                  30

Ile Met Ala Trp Tyr Arg Gln Ala Pro Gly Lys Gln Arg Glu Leu Val
        35                  40                  45

Ala Asn Lys Ala Arg Gly Gly Leu Pro Lys Tyr Ala Asp Ser Ala Lys
    50                  55                  60

Gly Arg Phe Thr Ile Ser Arg Asp Asn Ala Lys Asn Thr Ile Tyr Leu
65                  70                  75                  80

Gln Met Asn Asn Leu Lys Pro Asp Asp Thr Ala Val Tyr Tyr Cys Asn
                85                  90                  95

Ala Val Trp Asp Trp Ala Leu Ala Glu Tyr Trp Gly Gln Gly Thr Gln
            100                 105                 110

Val Thr Val Ser Ser
            115

<210> SEQ ID NO 64
<211> LENGTH: 117
<212> TYPE: PRT
<213> ORGANISM: Unknown
<220> FEATURE:
<223> OTHER INFORMATION: Camelidae

<400> SEQUENCE: 64

Gln Val Gln Leu Val Glu Ser Gly Gly Gly Leu Val Gln Ala Gly Gly
1               5                   10                  15
```

```
Ser Leu Arg Leu Ser Cys Ala Ala Ser Gly Ser Thr Ser Asp Ile Asn
            20                  25                  30

Ile Met Ala Trp Tyr Arg Gln Val Ser Gly Lys Ala Arg Glu Leu Val
        35                  40                  45

Ala Asn Lys Ala Arg Gly Gly Leu Pro Lys Tyr Ala Asp Phe Ala Lys
    50                  55                  60

Gly Arg Phe Thr Ile Ser Arg Asp Asn Ala Lys Asn Thr Ile Leu Leu
65                  70                  75                  80

Gln Met Asn Asn Leu Lys Pro Glu Asp Thr Gly Val Tyr Tyr Cys Asn
                85                  90                  95

Ala Val Ser Asp Trp Lys Leu Gly Asp Tyr Trp Gly Gln Gly Ile Gln
            100                 105                 110

Val Thr Val Ser Ser
        115
```

<210> SEQ ID NO 65
<211> LENGTH: 117
<212> TYPE: PRT
<213> ORGANISM: Unknown
<220> FEATURE:
<223> OTHER INFORMATION: Camelidae

<400> SEQUENCE: 65

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Ser Asp Ile Asn
            20                  25                  30

Ile Met Ala Trp Tyr Arg Gln Ala Ser Gly Lys Gln Arg Glu Leu Val
        35                  40                  45

Ala Asn Lys Ala Arg Gly Gly Leu Pro Lys Tyr Gly Asp Phe Val Lys
    50                  55                  60

Gly Arg Phe Ala Ile Ser Arg Asp Asn Ala Lys Asn Ile Val Tyr Leu
65                  70                  75                  80

Gln Met Asn Ser Leu Lys Pro Glu Asp Thr Ala Val Tyr Tyr Cys Asn
                85                  90                  95

Ala Val Thr Asp Trp Ala Leu Gly Asp Tyr Trp Gly Gln Gly Thr Gln
            100                 105                 110

Val Thr Val Ser Ser
        115
```

<210> SEQ ID NO 66
<211> LENGTH: 117
<212> TYPE: PRT
<213> ORGANISM: Unknown
<220> FEATURE:
<223> OTHER INFORMATION: Camelidae

<400> SEQUENCE: 66

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Ser Glu Ile Asn
            20                  25                  30

Val Met Ala Trp Tyr Arg Gln Val Ser Gly Lys Gln Arg Glu Leu Val
        35                  40                  45

Ala Asn Lys Ala Arg Gly Gly Leu Pro Lys Tyr Gly Asp Phe Val Lys
    50                  55                  60

Gly Arg Phe Ala Ile Ser Arg Asp Asn Ala Lys Asn Thr Ile Thr Leu
65                  70                  75                  80
```

Gln Met Asn Ser Leu Lys Pro Glu Asp Thr Ala Val Tyr Tyr Cys Asn
                85                  90                  95

Ala Val Thr Asp Trp Ala Leu Gly Asp Tyr Trp Gly Gln Gly Thr Gln
            100                 105                 110

Val Thr Val Ser Ser
        115

<210> SEQ ID NO 67
<211> LENGTH: 117
<212> TYPE: PRT
<213> ORGANISM: Unknown
<220> FEATURE:
<223> OTHER INFORMATION: Camelidae

<400> SEQUENCE: 67

Gln Val Gln Leu Val Glu Ser Gly Gly Gly Leu Val Gln Ala Gly Gly
1               5                   10                  15

Ser Leu Thr Leu Ser Cys Ala Ala Ser Gly Ser Thr Ser Glu Ile Asn
            20                  25                  30

Ile Met Ala Trp Tyr Arg Gln Val Ser Gly Asn Gln Arg Glu Leu Val
        35                  40                  45

Ala Asn Lys Ala Arg Gly Gly Leu Pro Lys Tyr Gly Asp Phe Val Lys
    50                  55                  60

Gly Arg Phe Ala Ile Ser Arg Asp Asn Ala Lys Asn Thr Ile Thr Leu
65                  70                  75                  80

Gln Met Asn Asn Leu Lys Pro Glu Asp Thr Ala Val Tyr Tyr Cys Asn
                85                  90                  95

Ala Val Thr Asp Trp Ala Leu Gly Asp Tyr Trp Gly Gln Gly Thr Gln
            100                 105                 110

Val Thr Val Ser Ser
        115

<210> SEQ ID NO 68
<211> LENGTH: 117
<212> TYPE: PRT
<213> ORGANISM: Unknown
<220> FEATURE:
<223> OTHER INFORMATION: Camelidae

<400> SEQUENCE: 68

Gln Val Gln Leu Val Glu Ser Gly Gly Gly Leu Val Gln Pro Gly Gly
1               5                   10                  15

Ser Leu Thr Leu Ser Cys Ala Ala Ser Gly Ser Ile Ala Asn Ile Gly
            20                  25                  30

Gly Met Ala Trp Tyr Arg Arg Leu Pro Gly Asn Lys Arg Ala Met Val
        35                  40                  45

Ala Ser Ile Thr Ser Ala Gly Thr Ala Ser Tyr Ile Asp Ser Val
    50                  55                  60

Lys Gly Arg Phe Thr Ile Ser Arg Asp Asn Ala Lys Asn Thr Val Tyr
65                  70                  75                  80

Leu Gln Met Thr Ser Leu Lys Pro Glu Asp Thr Ala Val Tyr Leu Cys
                85                  90                  95

Lys Ala Trp Asp Arg Asp Leu Val Asp Tyr Trp Gly Gln Gly Ile Gln
            100                 105                 110

Val Thr Val Ser Ser
        115

<210> SEQ ID NO 69
<211> LENGTH: 117
<212> TYPE: PRT
<213> ORGANISM: Unknown
<220> FEATURE:
<223> OTHER INFORMATION: Camelidae

<400> SEQUENCE: 69

Gln Val Gln Leu Val Glu Ser Gly Gly Gly Leu Val Gln Pro Gly Gly
1               5                   10                  15

Ser Leu Arg Leu Ser Cys Ala Ala Ser Gly Ser Ile Ala Asn Ile Asn
            20                  25                  30

Gly Met Ala Trp Tyr Arg Arg Leu Pro Gly Lys Val Arg Ala Met Val
        35                  40                  45

Ala Ser Ile Thr Ser Ala Gly Thr Ala Ser Ser Tyr Ile Asp Ser Val
    50                  55                  60

Lys Gly Arg Phe Thr Ile Ser Arg Asp Asn Ala Lys Asn Thr Val Tyr
65                  70                  75                  80

Leu Gln Met Thr Ser Leu Lys Pro Glu Asp Thr Ala Val Tyr Tyr Cys
                85                  90                  95

Lys Ala Trp Asp Arg Asp Leu Val Asp Tyr Trp Gly Gln Gly Ile Gln
            100                 105                 110

Val Thr Val Ser Ser
        115

<210> SEQ ID NO 70
<211> LENGTH: 117
<212> TYPE: PRT
<213> ORGANISM: Unknown
<220> FEATURE:
<223> OTHER INFORMATION: Camelidae

<400> SEQUENCE: 70

Gln Val Gln Leu Val Glu Ser Gly Gly Gly Leu Val Gln Ala Gly Gly
1               5                   10                  15

Ser Leu Thr Leu Ser Cys Ala Ala Ser Gly Ser Thr Ser Gly Ile Asn
            20                  25                  30

Val Met Ala Trp Tyr Arg Gln Ala Pro Gly Lys Gln Arg Glu Leu Val
        35                  40                  45

Ala Asn Lys Ala Arg Gly Gly Leu Pro Lys Tyr Ala Asp Phe Ala Lys
    50                  55                  60

Gly Arg Phe Thr Ile Ser Arg Asp Asn Thr Lys Asn Thr Ile Ser Leu
65                  70                  75                  80

Gln Met Asn Ser Leu Lys Pro Glu Asp Thr Ala Val Tyr Tyr Cys Asn
                85                  90                  95

Ala Leu Leu Asp Trp Arg Leu Gly Asp Tyr Trp Gly Gln Gly Thr Gln
            100                 105                 110

Val Thr Val Ser Ser
        115

<210> SEQ ID NO 71
<211> LENGTH: 117
<212> TYPE: PRT
<213> ORGANISM: Unknown
<220> FEATURE:
<223> OTHER INFORMATION: Camelidae

<400> SEQUENCE: 71

Gln Val Gln Leu Val Glu Ser Gly Gly Gly Leu Val Gln Ala Gly Gly
1               5                   10                  15

```
Ser Leu Arg Leu Ser Cys Ala Ala Ser Gly Asn Thr Ser Gly Ile Asn
            20                  25                  30

Leu Met Ala Trp Tyr Arg Gln Ala Ser Gly Lys Gln Arg Glu Leu Val
        35                  40                  45

Ala Asn Ile Ala Arg Gly Gly Leu Pro Lys Tyr Ala Asp Ser Ala Lys
    50                  55                  60

Gly Arg Phe Thr Ile Ser Arg Asp Asn Ala Lys Asn Thr Met Tyr Leu
65                  70                  75                  80

Gln Met Asn Ser Leu Lys Pro Glu Asp Thr Ala Val Tyr Tyr Cys Asn
                85                  90                  95

Ala Val Trp Asp Trp Lys Leu Gly Asp Tyr Trp Gly Gln Gly Thr Gln
            100                 105                 110

Val Thr Val Ser Ser
        115

<210> SEQ ID NO 72
<211> LENGTH: 117
<212> TYPE: PRT
<213> ORGANISM: Unknown
<220> FEATURE:
<223> OTHER INFORMATION: Camelidae

<400> SEQUENCE: 72

Gln Leu Gln Leu Val Glu Ser Gly Gly Gly Leu Val Gln Ala Gly Gly
1               5                   10                  15

Ser Leu Arg Leu Ser Cys Ala Ala Ser Gly Ser Thr Ser Gly Ile Asn
            20                  25                  30

Ile Met Ala Trp Tyr Arg Gln Arg Ser Gly Glu Pro Arg Glu Leu Val
        35                  40                  45

Ala Asn Lys Ala Arg Gly Gly Leu Pro Lys Tyr Ala Asp Phe Ala Arg
    50                  55                  60

Gly Arg Phe Thr Ile Ser Arg Asp Asn Ala Lys Asn Thr Ile Asp Leu
65                  70                  75                  80

Gln Met Ser Asn Leu Lys Pro Glu Asp Ser Ala Val Tyr Tyr Cys Asn
                85                  90                  95

Ala Val Trp Asp Trp Lys Leu Gly Asp Tyr Trp Gly Gln Gly Thr Gln
            100                 105                 110

Val Thr Val Ser Ser
        115

<210> SEQ ID NO 73
<211> LENGTH: 117
<212> TYPE: PRT
<213> ORGANISM: Unknown
<220> FEATURE:
<223> OTHER INFORMATION: Camelidae

<400> SEQUENCE: 73

Gln Val Gln Leu Val Glu Ser Gly Gly Gly Thr Val Gln Ala Gly Gly
1               5                   10                  15

Ser Leu Arg Leu Ser Cys Ala Ala Ser Gly Asn Thr Ser Gly Ile Asn
            20                  25                  30

Ile Met Ala Trp Tyr Arg Gln Ala Ser Gly Lys Gln Arg Glu Phe Ile
        35                  40                  45

Ala Asn Lys Ala Arg Gly Gly Leu Pro Lys Tyr Ala Asp Ser Ala Lys
    50                  55                  60

Gly Arg Phe Thr Ile Thr Arg Asp Asn Ala Lys Asn Thr Ile Tyr Leu
```

```
                65                  70                  75                  80
Gln Met Asn Asn Leu Lys Pro Glu Asp Thr Ala Val Tyr Tyr Cys Asn
                    85                  90                  95

Ala Val Trp Asp Trp Lys Leu Gly Asp Tyr Trp Gly Gln Gly Thr Gln
                100                 105                 110

Val Thr Val Ser Ser
            115

<210> SEQ ID NO 74
<211> LENGTH: 117
<212> TYPE: PRT
<213> ORGANISM: Unknown
<220> FEATURE:
<223> OTHER INFORMATION: Camelidae

<400> SEQUENCE: 74

Gln Val Gln Leu Val Glu Ser Gly Gly Gly Leu Val Gln Ala Gly Gly
1               5                   10                  15

Ser Leu Arg Leu Ser Cys Val Ala Ser Gly Ser Thr Ser Asp Ile Asn
                20                  25                  30

Ile Met Ala Trp Tyr Arg Gln Ala Gln Gly Lys Gln Arg Glu Leu Val
            35                  40                  45

Ala Asn Lys Ala Arg Gly Gly Leu Pro Lys Tyr Gly Asp Phe Val Lys
        50                  55                  60

Gly Arg Phe Ala Ile Ser Arg Asp Asn Ala Lys Asn Thr Ile Tyr Leu
65                  70                  75                  80

Gln Met Asn Ser Leu Lys Pro Glu Asp Thr Gly Val Tyr Tyr Cys Asn
                    85                  90                  95

Ala Val Thr Asp Trp Gln Leu Gly Asp Tyr Trp Gly Gln Gly Thr Gln
                100                 105                 110

Val Thr Val Ser Ser
            115

<210> SEQ ID NO 75
<211> LENGTH: 117
<212> TYPE: PRT
<213> ORGANISM: Unknown
<220> FEATURE:
<223> OTHER INFORMATION: Camelidae

<400> SEQUENCE: 75

Gln Leu Gln Leu Val Gln Ser Gly Gly Gly Leu Val Gln Ala Gly Gly
1               5                   10                  15

Ser Leu Arg Leu Ser Cys Val Ala Ser Gly Ser Thr Pro Asp Ile Asn
                20                  25                  30

Leu Met Ala Trp Tyr Arg Gln Ala Ser Gly Lys Gln Arg Glu Leu Val
            35                  40                  45

Ala Asn Lys Ala Arg Gly Gly Leu Pro Lys Tyr Ala Asp Phe Ala Lys
        50                  55                  60

Gly Arg Phe Thr Ile Ser Arg Asp Asn Ala Lys Asn Thr Ile Thr Leu
65                  70                  75                  80

Gln Met Asn Ser Leu Lys Pro Glu Asp Thr Ala Val Tyr Tyr Cys Asn
                    85                  90                  95

Ala Leu Leu Asp Trp Arg Ala Gly Asp Tyr Trp Gly Gln Gly Thr Gln
                100                 105                 110

Val Thr Val Ser Pro
            115
```

<210> SEQ ID NO 76
<211> LENGTH: 117
<212> TYPE: PRT
<213> ORGANISM: Unknown
<220> FEATURE:
<223> OTHER INFORMATION: Camelidae

<400> SEQUENCE: 76

Gln Leu Gln Leu Val Glu Ser Gly Gly Gly Leu Val Gln Ala Gly Gly
1               5                   10                  15

Ser Leu Arg Leu Ser Cys Val Ala Ser Gly Ser Thr Ser Asp Ile Asn
            20                  25                  30

Leu Met Ala Trp Tyr Arg Gln Ala Ser Gly Lys Gln Arg Glu Leu Val
        35                  40                  45

Ala Asn Lys Ala Arg Gly Gly Leu Pro Lys Tyr Ala Asp Phe Ala Lys
    50                  55                  60

Gly Arg Phe Thr Ile Ser Arg Asp Asn Ala Lys Asn Thr Ile Thr Leu
65                  70                  75                  80

Gln Met Asn Ser Leu Lys Pro Glu Asp Thr Ala Val Tyr Tyr Cys Asn
                85                  90                  95

Ala Leu Leu Asp Trp Arg Ala Gly Asp Tyr Trp Gly Gln Gly Thr Gln
            100                 105                 110

Val Thr Val Ser Pro
        115

<210> SEQ ID NO 77
<211> LENGTH: 117
<212> TYPE: PRT
<213> ORGANISM: Unknown
<220> FEATURE:
<223> OTHER INFORMATION: Camelidae

<400> SEQUENCE: 77

Gln Leu Gln Leu Val Glu Ser Gly Gly Gly Leu Val Gln Ala Gly Gly
1               5                   10                  15

Ser Leu Arg Leu Ser Cys Ala Ala Ser Gly Asp Thr Ser Asp Ile Asn
            20                  25                  30

Val Met Ala Trp Tyr Arg Gln Ala Ser Gly Lys Gln Arg Glu Leu Val
        35                  40                  45

Ala Asn Lys Ala Arg Gly Gly Leu Pro Lys Tyr Ala Asp Phe Ala Lys
    50                  55                  60

Gly Arg Phe Thr Ile Ser Arg Asp Asn Ala Lys Asn Thr Ile Thr Leu
65                  70                  75                  80

Gln Met Asn Ser Leu Lys Pro Glu Asp Thr Ala Val Tyr Tyr Cys Asn
                85                  90                  95

Ala Leu Leu Asp Trp Arg Ala Gly Asp Tyr Trp Gly Gln Gly Thr Gln
            100                 105                 110

Val Thr Val Ser Pro
        115

<210> SEQ ID NO 78
<211> LENGTH: 118
<212> TYPE: PRT
<213> ORGANISM: Unknown
<220> FEATURE:
<223> OTHER INFORMATION: Camelidae

<400> SEQUENCE: 78

Gln Leu Gln Leu Val Glu Ser Gly Gly Gly Ser Val Gln Ala Gly Gly

```
1               5                   10                  15
Ser Leu Lys Leu Ser Cys Val Ala Ser Gly Gly Ser Thr Ser Asp Ile
            20                  25                  30

Asn Leu Met Ala Trp Tyr Arg Gln Ala Ser Gly Lys Gln Arg Glu Leu
            35                  40                  45

Val Ala Asn Lys Ala Arg Gly Gly Leu Pro Lys Tyr Ala Ala Phe Ala
        50                  55                  60

Lys Gly Arg Phe Thr Ile Ser Arg Asp Asn Ala Lys Asn Thr Leu Val
65                  70                  75                  80

Leu Gln Met Asn Asp Leu Lys Pro Glu Asp Thr Ala Val Tyr Tyr Cys
                85                  90                  95

Asn Ala Leu Leu Asp Trp Ala Leu Gly Glu Tyr Trp Gly Gln Gly Thr
            100                 105                 110

Gln Val Thr Val Ser Ser
        115

<210> SEQ ID NO 79
<211> LENGTH: 118
<212> TYPE: PRT
<213> ORGANISM: Unknown
<220> FEATURE:
<223> OTHER INFORMATION: Camelidae

<400> SEQUENCE: 79

Gln Val Gln Leu Val Glu Ser Gly Gly Gly Leu Val Gln Ala Gly Gly
1               5                   10                  15

Ser Leu Arg Leu Ser Cys Ala Ala Ser Gly Arg Ser Thr Ser Asp Ile
            20                  25                  30

Asn Ile Met Ala Trp Tyr Arg Gln Ala Ser Gly Lys Gln Arg Glu Leu
            35                  40                  45

Val Ala Asn Lys Ala Arg Gly Gly Leu Pro Lys Tyr Ala Asp Ser Ala
        50                  55                  60

Lys Gly Arg Phe Thr Ile Ser Arg Asp Asn Ala Lys Asn Thr Val Tyr
65                  70                  75                  80

Leu Glu Met Asn Ser Leu Lys Pro Glu Asp Thr Ala Ile Tyr Tyr Cys
                85                  90                  95

Asn Ala Val Leu Asp Trp Lys Leu Gly Glu Tyr Trp Gly Gln Gly Thr
            100                 105                 110

Gln Val Thr Val Ser Ser
        115

<210> SEQ ID NO 80
<211> LENGTH: 117
<212> TYPE: PRT
<213> ORGANISM: Unknown
<220> FEATURE:
<223> OTHER INFORMATION: Camelidae

<400> SEQUENCE: 80

Gln Val Gln Leu Val Glu Ser Gly Gly Gly Leu Val Gln Pro Gly Gly
1               5                   10                  15

Ser Leu Arg Leu Ser Cys Ala Ala Ser Gly Asn Thr Ser Gly Ile Asn
            20                  25                  30

Val Met Ala Trp Tyr Arg Gln Ala Ser Gly Lys Gln Arg Glu Leu Val
        35                  40                  45

Ala Asn Lys Ala Arg Gly Gly Leu Pro Lys Tyr Ala Asp Phe Ala Lys
        50                  55                  60
```

```
Gly Arg Phe Thr Ile Ser Arg Asp Asn Ala Lys Asn Thr Val Ser Leu
65                  70                  75                  80

Gln Met Asn Ser Leu Lys Pro Glu Asp Thr Ala Val Tyr Tyr Cys Asn
                85                  90                  95

Ala Val Trp Asp Trp Gln Leu Gly Asp Tyr Trp Gly Gln Gly Thr Gln
            100                 105                 110

Val Thr Val Ser Ser
        115
```

<210> SEQ ID NO 81
<211> LENGTH: 117
<212> TYPE: PRT
<213> ORGANISM: Unknown
<220> FEATURE:
<223> OTHER INFORMATION: Camelidae

<400> SEQUENCE: 81

```
Gln Val Gln Leu Val Glu Ser Gly Gly Gly Leu Val Gln Ala Gly Gly
1               5                   10                  15

Ser Leu Arg Leu Thr Cys Val Ala Ser Gly Asn Thr Ser Gly Ile Asn
            20                  25                  30

Ile Met Ala Trp Tyr Arg Gln Thr Ser Gly Lys Gln Arg Glu Leu Val
        35                  40                  45

Ala Asn Lys Ala Arg Gly Gly Leu Pro Lys Tyr Ala Asp Ser Ala Lys
    50                  55                  60

Gly Arg Phe Thr Ile Ser Arg Asp Asn Ala Lys Asn Thr Leu Tyr Leu
65                  70                  75                  80

Gln Met Asn Asn Leu Lys Pro Glu Asp Thr Gly Val Tyr Tyr Cys Asn
                85                  90                  95

Ala Val Trp Asp Trp Gln Leu Gly Asp Tyr Trp Gly Gln Gly Thr Gln
            100                 105                 110

Val Thr Val Ser Ser
        115
```

<210> SEQ ID NO 82
<211> LENGTH: 118
<212> TYPE: PRT
<213> ORGANISM: Unknown
<220> FEATURE:
<223> OTHER INFORMATION: Camelidae

<400> SEQUENCE: 82

```
Gln Leu Gln Leu Val Glu Ser Gly Gly Gly Leu Val Gln Ala Gly Gly
1               5                   10                  15

Ser Leu Arg Leu Ser Cys Ala Ala Ser Arg Asp Ile Phe Ser Phe Asn
            20                  25                  30

Val Met Gly Trp Tyr Arg Gln Ala Pro Gly Lys Gln Arg Glu Leu Val
        35                  40                  45

Ala Phe Ile Thr Ser Ala Gly Tyr Thr Asn Tyr Val His Ser Val Lys
    50                  55                  60

Gly Arg Phe Thr Ile Ser Arg Asp Asn Thr Lys Asn Thr Val Tyr Leu
65                  70                  75                  80

Gln Met Ser Ser Leu Lys Pro Glu Asp Thr Ala Val Tyr Tyr Cys Ala
                85                  90                  95

Ala Ala Glu Ala Tyr Ala Glu Lys Tyr Asp Tyr Trp Gly Gln Gly Thr
            100                 105                 110

Gln Val Thr Val Ser Ser
        115
```

<210> SEQ ID NO 83
<211> LENGTH: 118
<212> TYPE: PRT
<213> ORGANISM: Unknown
<220> FEATURE:
<223> OTHER INFORMATION: Camelidae

<400> SEQUENCE: 83

Gln Leu Gln Leu Val Glu Ser Gly Gly Gly Leu Val Gln Ala Gly Gly
1               5                   10                  15

Ser Leu Arg Leu Ser Cys Ala Ala Ser Gly Ser Ile Ser Ser Ile Asn
            20                  25                  30

Val Met Gly Trp Tyr Arg Gln Ala Pro Gly Lys Gln Arg Glu Leu Val
        35                  40                  45

Ala Phe Ile Thr Thr Pro Gly Tyr Thr Asn Tyr Ala His Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Pro Gln Asp Thr Ala Val Tyr Tyr Cys Ala
                85                  90                  95

Ala Ala Glu Ala Tyr Ala Glu Lys Tyr Asp Tyr Trp Gly Gln Gly Thr
            100                 105                 110

Gln Val Thr Val Ser Ser
        115

<210> SEQ ID NO 84
<211> LENGTH: 117
<212> TYPE: PRT
<213> ORGANISM: Unknown
<220> FEATURE:
<223> OTHER INFORMATION: Camelidae

<400> SEQUENCE: 84

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Ser Asn Ile Asn
            20                  25                  30

Ile Met Ala Trp Tyr Arg Gln Ala Leu Gly Lys Pro Arg Glu Leu Val
        35                  40                  45

Ala Asn Lys Ala Arg Gly Gly Leu Pro Lys Tyr Ala Asp Phe Ala Lys
    50                  55                  60

Gly Arg Phe Thr Ile Ser Arg Asp Asn Ala Lys Asn Ala Val Tyr Leu
65                  70                  75                  80

Gln Met Asn Ser Leu Lys Pro Glu Asp Thr Ala Val Tyr Tyr Cys Asn
                85                  90                  95

Ala Val Glu Asp Trp Arg Leu Gly Asp Tyr Trp Gly Gln Gly Thr Gln
            100                 105                 110

Val Thr Val Ser Ser
        115

<210> SEQ ID NO 85
<211> LENGTH: 117
<212> TYPE: PRT
<213> ORGANISM: Unknown
<220> FEATURE:
<223> OTHER INFORMATION: Camelidae

<400> SEQUENCE: 85

```
Gln Val Gln Leu Val Glu Ser Gly Gly Gly Leu Val Gln Ala Gly Gly
1               5                   10                  15
Ser Leu Arg Leu Ser Cys Ala Ala Ser Gly Thr Ser Ser Ile Asn
            20                  25                  30
Ile Met Ala Trp Tyr Arg Gln Ala Pro Gly Lys Pro Arg Glu Leu Val
        35                  40                  45
Ala Asn Lys Ala Arg Gly Gly Leu Pro Lys Tyr Ala Asp Phe Ala Lys
    50                  55                  60
Gly Arg Phe Thr Ile Ser Arg Asp Asn Ala Lys Asn Thr Val Tyr Leu
65                  70                  75                  80
Gln Met Asn Ser Leu Lys Pro Glu Asp Thr Ala Val Tyr Tyr Cys Asn
                85                  90                  95
Ala Val Glu Asp Trp Arg Leu Gly Asp Tyr Trp Gly Gln Gly Thr Gln
            100                 105                 110
Val Thr Val Ser Ser
            115
```

<210> SEQ ID NO 86
<211> LENGTH: 116
<212> TYPE: PRT
<213> ORGANISM: Unknown
<220> FEATURE:
<223> OTHER INFORMATION: Camelidae

<400> SEQUENCE: 86

```
Leu Gln Leu Val Glu Ser Gly Gly Gly Leu Val Gln Ala Gly Gly Ser
1               5                   10                  15
Leu Arg Leu Ser Cys Ala Ala Ser Gly Ser Thr Ser Gly Ile Asn Leu
            20                  25                  30
Met Ala Trp Tyr Arg Gln Thr Ser Gly Lys Gln Arg Glu Leu Val Ala
        35                  40                  45
Asn Ile Ala Arg Gly Gly Leu Pro Lys Tyr Gly Asp Ser Ala Lys Gly
    50                  55                  60
Arg Phe Thr Ile Ser Arg Asp Asn Ala Lys Asn Thr Ile Tyr Leu Gln
65                  70                  75                  80
Met Asn Asn Leu Lys Pro Glu Asp Thr Ala Val Tyr Tyr Cys Asn Ala
                85                  90                  95
Val Leu Asp Trp Gln Leu Gly Asp Tyr Trp Gly Gln Gly Thr Gln Val
            100                 105                 110
Thr Val Ser Ser
            115
```

<210> SEQ ID NO 87
<211> LENGTH: 119
<212> TYPE: PRT
<213> ORGANISM: Unknown
<220> FEATURE:
<223> OTHER INFORMATION: Camelidae

<400> SEQUENCE: 87

```
Gln Val Gln Leu Val Glu Ser Gly Gly Gly Leu Val Gln Pro Gly Gly
1               5                   10                  15
Ser Leu Arg Leu Ser Cys Ala Ala Ser Thr Ser Gly Phe Ser Phe Ser
            20                  25                  30
Asp Tyr Tyr Val Asn Trp Phe Arg Gln Pro Pro Gly Lys Gln His Glu
        35                  40                  45
Val Val Ala Ser Ile Asn Pro Asn Gly Phe Thr Asn Tyr Ala Asp Ser
    50                  55                  60
```

Val Lys Gly Arg Phe Thr Ile Ser Arg Asp Asn Val Lys Asn Ala Val
65                  70                  75                  80

Tyr Leu Gln Met Asn Ser Leu Lys Pro Glu Asp Thr Ala Leu Tyr Tyr
                85                  90                  95

Cys His Ala Val Arg Ile Ser Gly Gly Ala Asn Tyr Trp Gly Pro Gly
            100                 105                 110

Thr Gln Val Thr Val Ser Ser
            115

<210> SEQ ID NO 88
<211> LENGTH: 113
<212> TYPE: PRT
<213> ORGANISM: Unknown
<220> FEATURE:
<223> OTHER INFORMATION: Camelidae

<400> SEQUENCE: 88

Gln Val Gln Leu Val Glu Ser Gly Gly Gly Leu Val Gln Thr Gly Gly
1               5                   10                  15

Ser Leu Arg Leu Ser Cys Ala Ala Ser Gly Ile Ser Phe Ser Asp Ala
            20                  25                  30

Ala Met Gly Trp Tyr Arg Gln Thr Pro Arg Lys Ser Arg Glu Ala Val
        35                  40                  45

Ala Thr Ile Gly Asn Arg Gly Ser Val Ser Tyr Ile Asp Ala Val Lys
    50                  55                  60

Gly Arg Phe Thr Ile Ser Arg Asp Asn Ala Lys Asn Thr Leu Tyr Leu
65                  70                  75                  80

Gln Met Asn Ser Leu Glu Pro Glu Asp Thr Ala Val Tyr Tyr Cys Arg
                85                  90                  95

Ser Phe Gln Pro Asp Leu Trp Gly Gln Gly Thr Gln Val Thr Val Ser
            100                 105                 110

Ser

<210> SEQ ID NO 89
<211> LENGTH: 117
<212> TYPE: PRT
<213> ORGANISM: Unknown
<220> FEATURE:
<223> OTHER INFORMATION: Camelidae

<400> SEQUENCE: 89

Gln Val Gln Leu Val Glu Ser Gly Gly Gly Leu Val Gln Ala Gly Gly
1               5                   10                  15

Ser Leu Arg Leu Ser Cys Thr Ala Ser Gly Asn Thr Ser Gly Ile Asn
            20                  25                  30

Ile Met Ala Trp Tyr Arg Gln Thr Ser Gly Lys Gln Arg Glu Phe Leu
        35                  40                  45

Ala Asn Ile Ala Arg Gly Gly Leu Pro Lys Tyr Ser Asp Ser Ala Lys
    50                  55                  60

Gly Arg Phe Thr Ile Ser Arg Asp Asn Ala Lys Asn Thr Val His Leu
65                  70                  75                  80

Gln Met Asn Ser Leu Lys Pro Glu Asp Thr Ala Val Tyr Tyr Cys Asn
                85                  90                  95

Ala Leu Trp Asp Trp Arg Leu Gly Glu Tyr Trp Gly Gln Gly Thr Gln
            100                 105                 110

Val Thr Val Ser Ser
            115

<210> SEQ ID NO 90
<211> LENGTH: 117
<212> TYPE: PRT
<213> ORGANISM: Unknown
<220> FEATURE:
<223> OTHER INFORMATION: Camelidae

<400> SEQUENCE: 90

Gln Val Gln Leu Val Glu Ser Gly Gly Gly Leu Val Gln Ala Gly Gly
1               5                   10                  15

Ser Leu Arg Leu Ser Cys Val Ala Ser Gly Asn Thr Ser Gly Ile Asn
            20                  25                  30

Leu Met Ala Trp Tyr Arg Gln Ala Pro Gly Lys Gln Arg Glu Leu Val
        35                  40                  45

Ala Asn Lys Ala Arg Gly Gly Leu Pro Lys Tyr Ala Asp Phe Ala Lys
    50                  55                  60

Gly Arg Phe Thr Ile Ser Arg Asp Asn Ala Lys Asn Thr Val Tyr Leu
65                  70                  75                  80

Gln Met Asn Met Leu Lys Pro Glu Asp Thr Ala Val Tyr Tyr Cys Asn
                85                  90                  95

Ala Leu Trp Asp Trp Arg Leu Gly Glu Tyr Trp Gly Gln Gly Thr Gln
            100                 105                 110

Val Thr Val Ser Ser
        115

<210> SEQ ID NO 91
<211> LENGTH: 117
<212> TYPE: PRT
<213> ORGANISM: Unknown
<220> FEATURE:
<223> OTHER INFORMATION: Camelidae

<400> SEQUENCE: 91

Gln Val Gln Leu Val Glu Ser Gly Gly Gly Leu Val Gln Ala Gly Gly
1               5                   10                  15

Ser Leu Arg Leu Ser Cys Ala Ala Ser Gly Ser Thr Ser Ser Ile Asn
            20                  25                  30

Ile Met Ala Trp Tyr Arg Gln Ala Ser Gly Lys Gln Arg Glu Leu Val
        35                  40                  45

Ala Asn Lys Ala Arg Gly Gly Leu Pro Lys Tyr Ala Asp Phe Ala Lys
    50                  55                  60

Gly Arg Phe Thr Val Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys His
                85                  90                  95

Ala Leu Glu Asp Trp Ala Leu Gly Glu Tyr Trp Gly Gln Gly Ile Gln
            100                 105                 110

Val Thr Val Ser Ser
        115

<210> SEQ ID NO 92
<211> LENGTH: 117
<212> TYPE: PRT
<213> ORGANISM: Unknown
<220> FEATURE:
<223> OTHER INFORMATION: Camelidae

<400> SEQUENCE: 92

```
Gln Val Gln Leu Val Glu Ser Gly Gly Gly Leu Val Gln Ala Gly Gly
1               5                   10                  15

Ser Leu Arg Leu Ser Cys Ala Ala Ser Gly Thr Ser Gly Ile Asn
            20                  25                  30

Ile Met Ala Trp Tyr Arg Gln Ala Ser Gly Lys Gln Arg Glu Leu Val
                35                  40                  45

Ala Asn Lys Ala Arg Gly Gly Leu Pro Lys Tyr Ala Asp Phe Ala Lys
50                  55                  60

Gly Arg Phe Thr Val Ser Arg Asp Asn Ala Lys Asn Thr Leu Tyr Leu
65                  70                  75                  80

Gln Met Asn Ser Leu Lys Pro Glu Asp Thr Ala Val Tyr Tyr Cys His
                85                  90                  95

Ala Leu Glu Asp Trp Ala Leu Gly Glu Tyr Trp Gly Gln Gly Ile Gln
                100                 105                 110

Val Thr Val Ser Ser
            115

<210> SEQ ID NO 93
<211> LENGTH: 117
<212> TYPE: PRT
<213> ORGANISM: Unknown
<220> FEATURE:
<223> OTHER INFORMATION: Camelidae

<400> SEQUENCE: 93

Gln Val Gln Leu Val Glu Ser Gly Gly Gly Leu Ala Gln Ala Gly Gly
1               5                   10                  15

Ser Leu Arg Leu Thr Cys Val Ala Ser Gly Asn Thr Ser Gly Ile Asn
            20                  25                  30

Ile Met Ala Trp Tyr Arg Gln Thr Ser Gly Lys Gln Arg Glu Leu Val
                35                  40                  45

Ala Asn Lys Ala Arg Gly Gly Leu Pro Lys Tyr Ala Asp Ser Ala Lys
50                  55                  60

Gly Arg Phe Thr Ile Ser Arg Asp Asn Ala Lys Asn Thr Leu Tyr Leu
65                  70                  75                  80

Gln Met Asn Ser Leu Lys Pro Glu Asp Thr Gly Val Tyr Tyr Cys Asn
                85                  90                  95

Ala Leu Trp Asp Trp Ala Leu Gly Glu Tyr Trp Gly Gln Gly Ile Gln
                100                 105                 110

Val Thr Val Ser Ser
            115

<210> SEQ ID NO 94
<211> LENGTH: 117
<212> TYPE: PRT
<213> ORGANISM: Unknown
<220> FEATURE:
<223> OTHER INFORMATION: Camelidae

<400> SEQUENCE: 94

Gln Val Gln Leu Val Glu Ser Gly Gly Gly Leu Val Gln Ala Gly Gly
1               5                   10                  15

Ser Leu Thr Leu Ser Cys Ala Ala Ser Gly Asn Thr Ser Gly Ile Asn
            20                  25                  30

Ile Met Ala Trp Tyr Arg Gln Val Pro Gly Lys Gln Arg Glu Leu Val
                35                  40                  45

Ala Asn Lys Ala Arg Gly Gly Leu Pro Lys Tyr Ala Asp Phe Ala Lys
50                  55                  60
```

```
Gly Arg Phe Thr Ile Ser Arg Asp Asn Ala Lys Asn Thr Ile Tyr Leu
 65                  70                  75                  80

Gln Met Asn Ser Leu Lys Pro Glu Asp Thr Ala Val Tyr Tyr Cys Asn
                 85                  90                  95

Ala Val Trp Asp Trp Arg Leu Gly Glu Tyr Trp Gly Gln Gly Thr Gln
            100                 105                 110

Val Thr Val Ser Ser
        115

<210> SEQ ID NO 95
<211> LENGTH: 117
<212> TYPE: PRT
<213> ORGANISM: Unknown
<220> FEATURE:
<223> OTHER INFORMATION: Camelidae

<400> SEQUENCE: 95

Gln Leu Gln Leu Val Glu Ser Gly Gly Gly Leu Val Gln Ala Gly Gly
1               5                   10                  15

Ser Leu Arg Leu Ser Cys Ala Ala Ser Gly Asn Thr Ser Gly Ile Asn
            20                  25                  30

Leu Met Ala Trp Tyr Arg Gln Ala Ser Gly Lys Gln Arg Glu Phe Val
        35                  40                  45

Ala Asn Ile Ala Arg Gly Gly Leu Pro Lys Tyr Ala Asp Ser Ala Lys
    50                  55                  60

Gly Arg Phe Thr Ile Ser Arg Asn Asn Ala Lys Asn Thr Ile Tyr Leu
 65                  70                  75                  80

Gln Met Asn Ser Leu Lys Pro Glu Asp Thr Ala Val Tyr Tyr Cys Asn
                 85                  90                  95

Ala Val Trp Asp Trp Arg Leu Gly Glu Tyr Trp Gly Gln Gly Thr Gln
            100                 105                 110

Val Thr Val Ser Ser
        115

<210> SEQ ID NO 96
<211> LENGTH: 117
<212> TYPE: PRT
<213> ORGANISM: Unknown
<220> FEATURE:
<223> OTHER INFORMATION: Camelidae

<400> SEQUENCE: 96

Gln Val Gln Leu Val Glu Ser Gly Gly Gly Leu Val Gln Ala Gly Glu
1               5                   10                  15

Ser Leu Thr Leu Ser Cys Ala Ala Ser Gly Asn Thr Ser Gly Ile Asn
            20                  25                  30

Val Met Gly Trp Tyr Arg Gln Thr Ser Gly Lys Gln Arg Glu Leu Val
        35                  40                  45

Ala Asn Lys Ala Arg Gly Gly Leu Pro Lys Tyr Ala Asp Phe Ala Lys
    50                  55                  60

Gly Arg Phe Thr Ile Ser Arg Asp Asn Ala Lys Asn Thr Ile Tyr Leu
 65                  70                  75                  80

Gln Met Asn Ser Leu Lys Pro Glu Asp Thr Ala Val Tyr Tyr Cys Asn
                 85                  90                  95

Ala Val Trp Asp Trp Arg Leu Gly Glu Tyr Trp Gly Gln Gly Thr Gln
            100                 105                 110

Val Thr Val Ser Ser
```

<210> SEQ ID NO 97
<211> LENGTH: 117
<212> TYPE: PRT
<213> ORGANISM: Unknown
<220> FEATURE:
<223> OTHER INFORMATION: Camelidae

<400> SEQUENCE: 97

Gln Leu Gln Leu Val Glu Ser Gly Gly Gly Leu Val Gln Ala Gly Gly
1               5                   10                  15

Ser Leu Arg Leu Ser Cys Thr Ala Ser Gly Asn Thr Ser Gly Ile Asn
            20                  25                  30

Ile Met Ala Trp Tyr Arg Gln Thr Ser Gly Lys Gln Arg Glu Phe Leu
        35                  40                  45

Ala Asn Ile Ala Arg Gly Gly Leu Pro Lys Tyr Ser Asp Ser Ala Lys
    50                  55                  60

Gly Arg Phe Thr Ile Ser Arg Asp Asn Ala Lys Asn Thr Val His Leu
65                  70                  75                  80

Gln Met Asn Ser Leu Lys Pro Glu Asp Thr Ala Val Tyr Tyr Cys Asn
                85                  90                  95

Ala Val Trp Asp Trp Arg Leu Gly Glu Tyr Trp Gly Gln Gly Thr Gln
            100                 105                 110

Val Thr Val Ser Ser
        115

<210> SEQ ID NO 98
<211> LENGTH: 117
<212> TYPE: PRT
<213> ORGANISM: Unknown
<220> FEATURE:
<223> OTHER INFORMATION: Camelidae

<400> SEQUENCE: 98

Gln Val Gln Leu Val Glu Ser Gly Gly Gly Leu Val Gln Ala Gly Gly
1               5                   10                  15

Ser Leu Arg Leu Ser Cys Ile Ala Ser Gly Ser Thr Asp Ile Asn
            20                  25                  30

Val Met Ala Trp Tyr Arg Gln Ala Ser Gly Lys Gln Arg Glu Leu Val
        35                  40                  45

Ala Asn Lys Ala Arg Gly Gly Leu Pro Lys Tyr Gly Asp Phe Ala Lys
    50                  55                  60

Gly Arg Phe Thr Ile Ser Arg Asp Asn Ala Lys Asn Thr Ile Tyr Leu
65                  70                  75                  80

Gln Met Asn Asp Leu Lys Pro Glu Asp Thr Ala Val Tyr Tyr Cys Asn
                85                  90                  95

Ala Val Leu Asp Trp Arg Leu Gly Asp Tyr Trp Gly Gln Gly Thr Gln
            100                 105                 110

Val Thr Val Ser Ser
        115

<210> SEQ ID NO 99
<211> LENGTH: 117
<212> TYPE: PRT
<213> ORGANISM: Unknown
<220> FEATURE:
<223> OTHER INFORMATION: Camelidae

<400> SEQUENCE: 99

```
Gln Val Gln Leu Val Glu Ser Gly Gly Leu Val Gln Ala Gly Gly
1               5                   10                  15

Ser Leu Arg Leu Ser Cys Val Ala Ser Gly Ser Thr Ser Asp Ile Asn
            20                  25                  30

Ile Met Ala Trp Tyr Arg Gln Ala Ser Gly Lys Gln Arg Glu Leu Val
        35                  40                  45

Ala Asn Met Ala Arg Gly Gly Leu Pro Lys Tyr Ala Asp Ser Ala Lys
    50                  55                  60

Gly Arg Phe Thr Ile Ser Arg Asp Asn Ala Lys Ser Thr Ile Asn Leu
65                  70                  75                  80

Gln Met Asn Asp Leu Lys Pro Glu Asp Thr Ala Val Tyr Tyr Cys Asn
                85                  90                  95

Ala Leu Leu Asp Trp Arg Leu Gly Glu Tyr Trp Gly Gln Gly Ile Gln
            100                 105                 110

Val Thr Val Ser Ser
            115

<210> SEQ ID NO 100
<211> LENGTH: 209
<212> TYPE: PRT
<213> ORGANISM: Homo sapiens

<400> SEQUENCE: 100

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys

<210> SEQ ID NO 101
<211> LENGTH: 219
<212> TYPE: PRT
<213> ORGANISM: Homo sapiens
```

<400> SEQUENCE: 101

Met Ala Ser Met Ser Gly Thr Thr Asn Thr Val Ala Tyr Asn Leu
1               5                   10                  15

Thr Trp Lys Ser Thr Asn Phe Lys Thr Ile Leu Glu Trp Glu Pro Lys
            20                  25                  30

Pro Val Asn Gln Val Tyr Thr Val Gln Ile Ser Thr Lys Ser Gly Asp
                35                  40                  45

Trp Lys Ser Lys Cys Phe Tyr Thr Thr Asp Thr Glu Cys Asp Leu Thr
    50                  55                  60

Asp Glu Ile Val Lys Asp Val Lys Gln Thr Tyr Leu Ala Arg Val Phe
65                  70                  75                  80

Ser Tyr Pro Ala Gly Asn Val Glu Ser Thr Gly Ser Ala Gly Glu Pro
                85                  90                  95

Leu Tyr Glu Asn Ser Pro Glu Phe Thr Pro Tyr Leu Glu Thr Asn Leu
            100                 105                 110

Gly Gln Pro Thr Ile Gln Ser Phe Glu Gln Val Gly Thr Lys Val Asn
                115                 120                 125

Val Thr Val Glu Asp Glu Arg Thr Leu Val Arg Arg Asn Asn Thr Phe
130                 135                 140

Leu Ser Leu Arg Asp Val Phe Gly Lys Asp Leu Ile Tyr Thr Leu Tyr
145                 150                 155                 160

Tyr Trp Lys Ser Ser Ser Ser Gly Lys Lys Thr Ala Lys Thr Asn Thr
                165                 170                 175

Asn Glu Phe Leu Ile Asp Val Asp Lys Gly Glu Asn Tyr Cys Phe Ser
            180                 185                 190

Val Gln Ala Val Ile Pro Ser Arg Thr Val Asn Arg Lys Ser Thr Asp
        195                 200                 205

Ser Pro Val Glu Cys His His His His His His
    210                 215

<210> SEQ ID NO 102
<211> LENGTH: 125
<212> TYPE: PRT
<213> ORGANISM: Unknown
<220> FEATURE:
<223> OTHER INFORMATION: Camelidae

<400> SEQUENCE: 102

Met Ala Gln Val Gln Leu Val Glu Ser Gly Gly Gly Leu Val Gln Pro
1               5                   10                  15

Gly Gly Ser Leu Thr Leu Ser Cys Ala Ala Ser Gly Ser Ile Ala Asn
            20                  25                  30

Ile Gly Gly Met Ala Trp Tyr Arg Arg Leu Pro Gly Asn Lys Arg Ala
        35                  40                  45

Met Val Ala Ser Ile Thr Ser Ala Gly Thr Ala Ser Ser Tyr Ile Asp
    50                  55                  60

Ser Val Lys Gly Arg Phe Thr Ile Ser Arg Asp Asn Ala Lys Asn Thr
65                  70                  75                  80

Val Tyr Leu Gln Met Thr Ser Leu Lys Pro Glu Asp Thr Ala Val Tyr
                85                  90                  95

Leu Cys Lys Ala Trp Asp Arg Asp Leu Val Asp Tyr Trp Gly Gln Gly
            100                 105                 110

Ile Gln Val Thr Val Ser Ser His His His His His
        115                 120                 125

<210> SEQ ID NO 103
<211> LENGTH: 125
<212> TYPE: PRT
<213> ORGANISM: Unknown
<220> FEATURE:
<223> OTHER INFORMATION: Camelidae

<400> SEQUENCE: 103

Met Ala Gln Val Gln Leu Val Glu Ser Gly Gly Gly Leu Val Gln Ala
1               5                   10                  15

Gly Gly Ser Leu Thr Leu Ser Cys Ala Ala Ser Gly Ser Thr Ser Gly
            20                  25                  30

Ile Asn Val Met Ala Trp Tyr Arg Gln Ala Pro Gly Lys Gln Arg Glu
        35                  40                  45

Leu Val Ala Asn Lys Ala Arg Gly Gly Leu Pro Lys Tyr Ala Asp Phe
    50                  55                  60

Ala Lys Gly Arg Phe Thr Ile Ser Arg Asp Asn Thr Lys Asn Thr Ile
65                  70                  75                  80

Ser Leu Gln Met Asn Ser Leu Lys Pro Glu Asp Thr Ala Val Tyr Tyr
                85                  90                  95

Cys Asn Ala Leu Leu Asp Trp Arg Leu Gly Asp Tyr Trp Gly Gln Gly
            100                 105                 110

Thr Gln Val Thr Val Ser Ser His His His His His
        115                 120                 125

<210> SEQ ID NO 104
<211> LENGTH: 368
<212> TYPE: PRT
<213> ORGANISM: Homo sapiens

<400> SEQUENCE: 104

Met Ala Ser Met Ser Gly Thr Thr Asn Thr Val Ala Ala Tyr Asn Leu
1               5                   10                  15

Thr Trp Lys Ser Thr Asn Phe Lys Thr Ile Leu Glu Trp Glu Pro Lys
            20                  25                  30

Pro Val Asn Gln Val Tyr Thr Val Gln Ile Ser Thr Lys Ser Gly Asp
        35                  40                  45

Trp Lys Ser Lys Cys Phe Tyr Thr Thr Asp Thr Glu Cys Asp Leu Thr
    50                  55                  60

Asp Glu Ile Val Lys Asp Val Lys Gln Thr Tyr Leu Ala Arg Val Phe
65                  70                  75                  80

Ser Tyr Pro Ala Gly Asn Val Glu Ser Thr Gly Ser Ala Gly Glu Pro
                85                  90                  95

Leu Tyr Glu Asn Ser Pro Glu Phe Thr Pro Tyr Leu Glu Thr Asn Leu
            100                 105                 110

Gly Gln Pro Thr Ile Gln Ser Phe Glu Gln Val Gly Thr Lys Val Asn
        115                 120                 125

Val Thr Val Glu Asp Glu Arg Thr Leu Val Arg Arg Asn Asn Thr Phe
    130                 135                 140

Leu Ser Leu Arg Asp Val Phe Gly Lys Asp Leu Ile Tyr Thr Leu Tyr
145                 150                 155                 160

Tyr Trp Lys Ser Ser Ser Gly Lys Lys Thr Ala Lys Thr Asn Thr
                165                 170                 175

Asn Glu Phe Leu Ile Asp Val Asp Lys Gly Glu Asn Tyr Cys Phe Ser
            180                 185                 190

Val Gln Ala Val Ile Pro Ser Arg Thr Val Asn Arg Lys Ser Thr Asp

```
            195                 200                 205
Ser Pro Val Glu Cys Gly Ser Gly Gly Thr Gly Gly Ser Gly
210                 215                 220

Gly Ser Gly Gly Gly Thr Gly Gly Ser Gly Ala Ile Glu Pro Arg
225                 230                 235                 240

Ser Phe Ser Gln Asn Gln Val Gln Leu Val Glu Ser Gly Gly Leu
            245                 250                 255

Val Gln Pro Gly Gly Ser Leu Thr Leu Ser Cys Ala Ala Ser Gly Ser
                260                 265                 270

Ile Ala Asn Ile Gly Gly Met Ala Trp Tyr Arg Arg Leu Pro Gly Asn
            275                 280                 285

Lys Arg Ala Met Val Ala Ser Ile Thr Ser Ala Gly Thr Ala Ser Ser
        290                 295                 300

Tyr Ile Asp Ser Val Lys Gly Arg Phe Thr Ile Ser Arg Asp Asn Ala
305                 310                 315                 320

Lys Asn Thr Val Tyr Leu Gln Met Thr Ser Leu Lys Pro Glu Asp Thr
                325                 330                 335

Ala Val Tyr Leu Cys Lys Ala Trp Asp Arg Asp Leu Val Asp Tyr Trp
            340                 345                 350

Gly Gln Gly Ile Gln Val Thr Val Ser Ser His His His His His His
        355                 360                 365

<210> SEQ ID NO 105
<211> LENGTH: 368
<212> TYPE: PRT
<213> ORGANISM: Homo sapiens

<400> SEQUENCE: 105

Met Ala Ser Met Ser Gly Thr Thr Asn Thr Val Ala Ala Tyr Asn Leu
1               5                   10                  15

Thr Trp Lys Ser Thr Asn Phe Lys Thr Ile Leu Glu Trp Glu Pro Lys
            20                  25                  30

Pro Val Asn Gln Val Tyr Thr Val Gln Ile Ser Thr Lys Ser Gly Asp
        35                  40                  45

Trp Lys Ser Lys Cys Phe Tyr Thr Thr Asp Thr Glu Cys Asp Leu Thr
50                  55                  60

Asp Glu Ile Val Lys Asp Val Lys Gln Thr Tyr Leu Ala Arg Val Phe
65                  70                  75                  80

Ser Tyr Pro Ala Gly Asn Val Glu Ser Thr Gly Ser Ala Gly Glu Pro
                85                  90                  95

Leu Tyr Glu Asn Ser Pro Glu Phe Thr Pro Tyr Leu Glu Thr Asn Leu
            100                 105                 110

Gly Gln Pro Thr Ile Gln Ser Phe Glu Gln Val Gly Thr Lys Val Asn
        115                 120                 125

Val Thr Val Glu Asp Glu Arg Thr Leu Val Arg Arg Asn Asn Thr Phe
130                 135                 140

Leu Ser Leu Arg Asp Val Phe Gly Lys Asp Leu Ile Tyr Thr Leu Tyr
145                 150                 155                 160

Tyr Trp Lys Ser Ser Ser Ser Gly Lys Lys Thr Ala Lys Thr Asn Thr
                165                 170                 175

Asn Glu Phe Leu Ile Asp Val Asp Lys Gly Glu Asn Tyr Cys Phe Ser
            180                 185                 190

Val Gln Ala Val Ile Pro Ser Arg Thr Val Asn Arg Lys Ser Thr Asp
        195                 200                 205
```

```
Ser Pro Val Glu Cys Gly Ser Gly Gly Thr Gly Gly Ser Gly
    210                 215                 220

Gly Ser Gly Gly Gly Thr Gly Gly Gly Ser Gly Ala Ile Glu Pro Arg
225                 230                 235                 240

Ser Phe Ser Gln Asn Gln Val Gln Leu Val Glu Ser Gly Gly Leu
                245                 250                 255

Val Gln Ala Gly Gly Ser Leu Thr Leu Ser Cys Ala Ala Ser Gly Ser
                260                 265                 270

Thr Ser Gly Ile Asn Val Met Ala Trp Tyr Arg Gln Ala Pro Gly Lys
                275                 280                 285

Gln Arg Glu Leu Val Ala Asn Lys Ala Arg Gly Gly Leu Pro Lys Tyr
    290                 295                 300

Ala Asp Phe Ala Lys Gly Arg Phe Thr Ile Ser Arg Asp Asn Thr Lys
305                 310                 315                 320

Asn Thr Ile Ser Leu Gln Met Asn Ser Leu Lys Pro Glu Asp Thr Ala
                325                 330                 335

Val Tyr Tyr Cys Asn Ala Leu Leu Asp Trp Arg Leu Gly Asp Tyr Trp
                340                 345                 350

Gly Gln Gly Thr Gln Val Thr Val Ser Ser His His His His His His
                355                 360                 365

<210> SEQ ID NO 106
<211> LENGTH: 358
<212> TYPE: PRT
<213> ORGANISM: Homo sapiens

<400> SEQUENCE: 106

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
                20                  25                  30

Val Tyr Thr Val Gln Ile Ser Thr Lys Ser Gly Asp Trp Lys Ser Lys
            35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
                100                 105                 110

Ile Gln Ser Phe Glu Gln Val Gly Thr Lys Val Asn Val Thr Val Glu
            115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
                180                 185                 190

Ile Pro Ser Arg Thr Val Asn Arg Lys Ser Thr Asp Ser Pro Val Glu
            195                 200                 205

Cys Gly Ser Gly Gly Gly Thr Gly Gly Gly Ser Gly Gly Ser Gly Gly
    210                 215                 220
```

```
Gly Thr Gly Gly Gly Ser Gly Ala Ile Glu Pro Arg Ser Phe Ser Gln
225                 230                 235                 240

Asn Gln Val Gln Leu Val Glu Ser Gly Gly Leu Val Gln Pro Gly
            245                 250                 255

Gly Ser Leu Thr Leu Ser Cys Ala Ala Ser Gly Ser Ile Ala Asn Ile
            260                 265                 270

Gly Gly Met Ala Trp Tyr Arg Arg Leu Pro Gly Asn Lys Arg Ala Met
            275                 280                 285

Val Ala Ser Ile Thr Ser Ala Gly Thr Ala Ser Ser Tyr Ile Asp Ser
290                 295                 300

Val Lys Gly Arg Phe Thr Ile Ser Arg Asp Asn Ala Lys Asn Thr Val
305                 310                 315                 320

Tyr Leu Gln Met Thr Ser Leu Lys Pro Glu Asp Thr Ala Val Tyr Leu
            325                 330                 335

Cys Lys Ala Trp Asp Arg Asp Leu Val Asp Tyr Trp Gly Gln Gly Ile
            340                 345                 350

Gln Val Thr Val Ser Ser
            355

<210> SEQ ID NO 107
<211> LENGTH: 358
<212> TYPE: PRT
<213> ORGANISM: Homo sapiens

<400> SEQUENCE: 107

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Gly Ser Gly Gly Gly Thr Gly Gly Gly Ser Gly Gly Ser Gly Gly
    210                 215                 220

Gly Thr Gly Gly Gly Ser Gly Ala Ile Glu Pro Arg Ser Phe Ser Gln
```

```
225                 230                 235                 240

Asn Gln Val Gln Leu Val Glu Ser Gly Gly Gly Leu Val Gln Ala Gly
                245                 250                 255

Gly Ser Leu Thr Leu Ser Cys Ala Ala Ser Gly Ser Thr Ser Gly Ile
            260                 265                 270

Asn Val Met Ala Trp Tyr Arg Gln Ala Pro Gly Lys Gln Arg Glu Leu
        275                 280                 285

Val Ala Asn Lys Ala Arg Gly Gly Leu Pro Lys Tyr Ala Asp Phe Ala
    290                 295                 300

Lys Gly Arg Phe Thr Ile Ser Arg Asp Asn Thr Lys Asn Thr Ile Ser
305                 310                 315                 320

Leu Gln Met Asn Ser Leu Lys Pro Glu Asp Thr Ala Val Tyr Tyr Cys
                325                 330                 335

Asn Ala Leu Leu Asp Trp Arg Leu Gly Asp Tyr Trp Gly Gln Gly Thr
            340                 345                 350

Gln Val Thr Val Ser Ser
        355

<210> SEQ ID NO 108
<211> LENGTH: 348
<212> TYPE: PRT
<213> ORGANISM: Homo sapiens

<400> SEQUENCE: 108

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Gly Ser Gly Gly Thr Gly Gly Gly Ser Gly Gly Ser Gly Gly
    210                 215                 220

Gly Thr Gly Gly Gly Ser Gly Gln Val Gln Leu Val Glu Ser Gly Gly
225                 230                 235                 240
```

Gly Leu Val Gln Pro Gly Gly Ser Leu Thr Leu Ser Cys Ala Ala Ser
                245                 250                 255

Gly Ser Ile Ala Asn Ile Gly Met Ala Trp Tyr Arg Arg Leu Pro
        260                 265                 270

Gly Asn Lys Arg Ala Met Val Ala Ser Ile Thr Ser Ala Gly Thr Ala
        275                 280                 285

Ser Ser Tyr Ile Asp Ser Val Lys Gly Arg Phe Thr Ile Ser Arg Asp
        290                 295                 300

Asn Ala Lys Asn Thr Val Tyr Leu Gln Met Thr Ser Leu Lys Pro Glu
305                 310                 315                 320

Asp Thr Ala Val Tyr Leu Cys Lys Ala Trp Asp Arg Asp Leu Val Asp
                325                 330                 335

Tyr Trp Gly Gln Gly Ile Gln Val Thr Val Ser Ser
                340                 345

<210> SEQ ID NO 109
<211> LENGTH: 348
<212> TYPE: PRT
<213> ORGANISM: Homo sapiens

<400> SEQUENCE: 109

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Gly Ser Gly Gly Thr Gly Gly Gly Gly Ser Gly Gly Ser Gly Gly
    210                 215                 220

Gly Thr Gly Gly Gly Ser Gly Gln Val Gln Leu Val Glu Ser Gly Gly
225                 230                 235                 240

Gly Leu Val Gln Ala Gly Gly Ser Leu Thr Leu Ser Cys Ala Ala Ser
                245                 250                 255

Gly Ser Thr Ser Gly Ile Asn Val Met Ala Trp Tyr Arg Gln Ala Pro
        260                 265                 270

```
Gly Lys Gln Arg Glu Leu Val Ala Asn Lys Ala Arg Gly Gly Leu Pro
            275                 280                 285

Lys Tyr Ala Asp Phe Ala Lys Gly Arg Phe Thr Ile Ser Arg Asp Asn
290                 295                 300

Thr Lys Asn Thr Ile Ser Leu Gln Met Asn Ser Leu Lys Pro Glu Asp
305                 310                 315                 320

Thr Ala Val Tyr Tyr Cys Asn Ala Leu Leu Asp Trp Arg Leu Gly Asp
                325                 330                 335

Tyr Trp Gly Gln Gly Thr Gln Val Thr Val Ser Ser
            340                 345
```

<210> SEQ ID NO 110
<211> LENGTH: 263
<212> TYPE: PRT
<213> ORGANISM: Homo sapiens

<400> SEQUENCE: 110

```
Ser Gly Thr Thr Asn Thr Val Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Met Gly Gln Glu Lys Gly Glu Phe Arg Glu Ile Phe Tyr Ile Ile
    210                 215                 220

Gly Ala Val Val Phe Val Val Ile Ile Leu Val Ile Ile Leu Ala Ile
225                 230                 235                 240

Ser Leu His Lys Cys Arg Lys Ala Gly Val Gly Gln Ser Trp Lys Glu
                245                 250                 255

Asn Ser Pro Leu Asn Val Ser
            260
```

<210> SEQ ID NO 111
<211> LENGTH: 360
<212> TYPE: PRT

<213> ORGANISM: Homo sapiens

<400> SEQUENCE: 111

```
Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
    130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Gly Ser Gly Gly Thr Gly Gly Ser Gly Gly Ser Gly Gly
    210                 215                 220

Gly Thr Gly Gly Gly Ser Gly Leu Glu Ser Tyr Ile Asp Gly Arg Ile
225                 230                 235                 240

Val Glu Gly Gln Val Gln Leu Val Glu Ser Gly Gly Gly Leu Val Gln
            245                 250                 255

Pro Gly Gly Ser Leu Thr Leu Ser Cys Ala Ala Ser Gly Ser Ile Ala
        260                 265                 270

Asn Ile Gly Gly Met Ala Trp Tyr Arg Arg Leu Pro Gly Asn Lys Arg
    275                 280                 285

Ala Met Val Ala Ser Ile Thr Ser Ala Gly Thr Ala Ser Ser Tyr Ile
290                 295                 300

Asp Ser Val Lys Gly Arg Phe Thr Ile Ser Arg Asp Asn Ala Lys Asn
305                 310                 315                 320

Thr Val Tyr Leu Gln Met Thr Ser Leu Lys Pro Glu Asp Thr Ala Val
            325                 330                 335

Tyr Leu Cys Lys Ala Trp Asp Arg Asp Leu Val Asp Tyr Trp Gly Gln
        340                 345                 350

Gly Ile Gln Val Thr Val Ser Ser
    355                 360
```

<210> SEQ ID NO 112
<211> LENGTH: 360
<212> TYPE: PRT
<213> ORGANISM: Homo sapiens

<400> SEQUENCE: 112

Ser Gly Thr Thr Asn Thr Val Ala Ala Tyr Asn Leu Thr Trp Lys Ser
1               5                   10                  15

Thr Asn Phe Lys Thr Ile Leu Glu Trp Glu Pro Lys Pro Val Asn Gln
            20                  25                  30

Val Tyr Thr Val Gln Ile Ser Thr Lys Ser Gly Asp Trp Lys Ser Lys
        35                  40                  45

Cys Phe Tyr Thr Thr Asp Thr Glu Cys Asp Leu Thr Asp Glu Ile Val
    50                  55                  60

Lys Asp Val Lys Gln Thr Tyr Leu Ala Arg Val Phe Ser Tyr Pro Ala
65                  70                  75                  80

Gly Asn Val Glu Ser Thr Gly Ser Ala Gly Glu Pro Leu Tyr Glu Asn
                85                  90                  95

Ser Pro Glu Phe Thr Pro Tyr Leu Glu Thr Asn Leu Gly Gln Pro Thr
            100                 105                 110

Ile Gln Ser Phe Glu Gln Val Gly Thr Lys Val Asn Val Thr Val Glu
        115                 120                 125

Asp Glu Arg Thr Leu Val Arg Arg Asn Asn Thr Phe Leu Ser Leu Arg
130                 135                 140

Asp Val Phe Gly Lys Asp Leu Ile Tyr Thr Leu Tyr Tyr Trp Lys Ser
145                 150                 155                 160

Ser Ser Ser Gly Lys Lys Thr Ala Lys Thr Asn Thr Asn Glu Phe Leu
                165                 170                 175

Ile Asp Val Asp Lys Gly Glu Asn Tyr Cys Phe Ser Val Gln Ala Val
            180                 185                 190

Ile Pro Ser Arg Thr Val Asn Arg Lys Ser Thr Asp Ser Pro Val Glu
        195                 200                 205

Cys Gly Ser Gly Gly Thr Gly Gly Ser Gly Ser Gly Gly
210                 215                 220

Gly Thr Gly Gly Ser Gly Leu Glu Ser Tyr Ile Asp Gly Arg Ile
225                 230                 235                 240

Val Glu Gly Gln Val Gln Leu Val Glu Ser Gly Gly Gly Leu Val Gln
            245                 250                 255

Ala Gly Gly Ser Leu Thr Leu Ser Cys Ala Ala Ser Gly Ser Thr Ser
        260                 265                 270

Gly Ile Asn Val Met Ala Trp Tyr Arg Gln Ala Pro Gly Lys Gln Arg
    275                 280                 285

Glu Leu Val Ala Asn Lys Ala Arg Gly Gly Leu Pro Lys Tyr Ala Asp
290                 295                 300

Phe Ala Lys Gly Arg Phe Thr Ile Ser Arg Asp Asn Thr Lys Asn Thr
305                 310                 315                 320

Ile Ser Leu Gln Met Asn Ser Leu Lys Pro Glu Asp Thr Ala Val Tyr
                325                 330                 335

Tyr Cys Asn Ala Leu Leu Asp Trp Arg Leu Gly Asp Tyr Trp Gly Gln
            340                 345                 350

Gly Thr Gln Val Thr Val Ser Ser
        355                 360

<210> SEQ ID NO 113
<211> LENGTH: 22
<212> TYPE: PRT
<213> ORGANISM: Artificial Sequence
<220> FEATURE:
<223> OTHER INFORMATION: synthetic -continued

```
<400> SEQUENCE: 113

Gly Ser Gly Gly Gly Thr Gly Gly Ser Gly Gly Ser Gly Gly
1               5                   10                  15

Thr Gly Gly Gly Ser Gly
            20

<210> SEQ ID NO 114
<211> LENGTH: 15
<212> TYPE: PRT
<213> ORGANISM: Artificial Sequence
<220> FEATURE:
<223> OTHER INFORMATION: synthetic

<400> SEQUENCE: 114

Gly Gly Gly Gly Ser Gly Gly Gly Ser Gly Gly Gly Ser
1               5                   10                  15

<210> SEQ ID NO 115
<211> LENGTH: 10
<212> TYPE: PRT
<213> ORGANISM: Artificial Sequence
<220> FEATURE:
<223> OTHER INFORMATION: synthetic

<400> SEQUENCE: 115

Ala Ile Glu Pro Arg Ser Phe Ser Gln Asn
1               5                   10

<210> SEQ ID NO 116
<211> LENGTH: 12
<212> TYPE: PRT
<213> ORGANISM: Artificial Sequence
<220> FEATURE:
<223> OTHER INFORMATION: synthetic

<400> SEQUENCE: 116

Leu Glu Ser Tyr Ile Asp Gly Arg Ile Val Glu Gly
1               5                   10

<210> SEQ ID NO 117
<211> LENGTH: 12
<212> TYPE: PRT
<213> ORGANISM: Artificial Sequence
<220> FEATURE:
<223> OTHER INFORMATION: synthetic

<400> SEQUENCE: 117

Ser Asp Arg Ala Ile Glu Gly Arg Thr Ala Thr Ser
1               5                   10

<210> SEQ ID NO 118
<211> LENGTH: 311
<212> TYPE: PRT
<213> ORGANISM: Homo sapiens

<400> SEQUENCE: 118

Met Gly Leu Thr Leu Leu Leu Leu Leu Leu Gly Leu Glu Gly Gln
1               5                   10                  15

Gly Ile Val Gly Ser Leu Pro Glu Val Leu Gln Ala Pro Val Gly Ser
            20                  25                  30

Ser Ile Leu Val Gln Cys His Tyr Arg Leu Gln Asp Val Lys Ala Gln
        35                  40                  45

Lys Val Trp Cys Arg Phe Leu Pro Glu Gly Cys Gln Pro Leu Val Ser
    50                  55                  60
```

```
Ser Ala Val Asp Arg Arg Ala Pro Ala Gly Arg Arg Thr Phe Leu Thr
65                  70                  75                  80

Asp Leu Gly Gly Gly Leu Leu Gln Val Glu Met Val Thr Leu Gln Glu
                85                  90                  95

Glu Asp Ala Gly Glu Tyr Gly Cys Met Val Asp Gly Ala Arg Gly Pro
            100                 105                 110

Gln Ile Leu His Arg Val Ser Leu Asn Ile Leu Pro Pro Glu Glu Glu
            115                 120                 125

Glu Glu Thr His Lys Ile Gly Ser Leu Ala Glu Asn Ala Phe Ser Asp
130             135                 140

Pro Ala Gly Ser Ala Asn Pro Leu Glu Pro Ser Gln Asp Glu Lys Ser
145             150                 155                 160

Ile Pro Leu Ile Trp Gly Ala Val Leu Leu Val Gly Leu Leu Val Ala
                165                 170                 175

Ala Val Val Leu Phe Ala Val Met Ala Lys Arg Lys Gln Gly Asn Arg
            180                 185                 190

Leu Gly Val Cys Gly Arg Phe Leu Ser Ser Arg Val Ser Gly Met Asn
        195                 200                 205

Pro Ser Ser Val Val His His Val Ser Asp Ser Gly Pro Ala Ala Glu
        210                 215                 220

Leu Pro Leu Asp Val Pro His Ile Arg Leu Asp Ser Pro Pro Ser Phe
225             230                 235                 240

Asp Asn Thr Thr Tyr Thr Ser Leu Pro Leu Asp Ser Pro Ser Gly Lys
                245                 250                 255

Pro Ser Leu Pro Ala Pro Ser Ser Leu Pro Pro Leu Pro Pro Lys Val
            260                 265                 270

Leu Val Cys Ser Lys Pro Val Thr Tyr Ala Thr Val Ile Phe Pro Gly
        275                 280                 285

Gly Asn Lys Gly Gly Gly Thr Ser Cys Gly Pro Ala Gln Asn Pro Pro
    290                 295                 300

Asn Asn Gln Thr Pro Ser Ser
305             310
```